US012733918B2

(12) United States Patent
Kwon et al.

(10) Patent No.: US 12,733,918 B2
(45) Date of Patent: Sep. 15, 2026

(54) STIFFNESS-REINFORCED SURGICAL SYSTEM AND CONTROL METHOD THEREOF

(71) Applicants: ROEN Surgical, Inc., Daejeon (KR); KOREA ADVANCED INSTITUTE OF SCIENCE AND TECHNOLOGY, Daejeon (KR)

(72) Inventors: Dong Soo Kwon, Daejeon (KR); Han Soul Kim, Daejeon (KR); Jae Min You, Daejeon (KR); Duk Yoo Kong, Daejeon (KR)

(73) Assignees: ROEN Surgical, Inc., Daejeon (KR); KOREA ADVANCED INSTITUTE OF SCIENCE AND TECHNOLOGY, Daejeon (KR)

( * ) Notice: Subject to any disclaimer, the term of this patent is extended or adjusted under 35 U.S.C. 154(b) by 714 days.

(21) Appl. No.: 17/900,058

(22) Filed: Aug. 31, 2022

(65) Prior Publication Data

US 2023/0085601 A1 Mar. 16, 2023

Related U.S. Application Data

(60) Provisional application No. 63/342,955, filed on May 17, 2022.

(30) Foreign Application Priority Data

Sep. 1, 2021 (KR) ........................ 10-2021-0116224
Jun. 15, 2022 (KR) ........................ 10-2022-0072628
(Continued)

(51) Int. Cl.
*A61B 17/00* (2006.01)
*A61B 34/00* (2016.01)
*A61B 34/30* (2016.01)

(52) U.S. Cl.
CPC ........ *A61B 17/00234* (2013.01); *A61B 34/30* (2016.02); *A61B 34/71* (2016.02);
(Continued)

(58) Field of Classification Search
CPC ........ A61B 17/00234; A61B 2034/301; A61B 2017/00398; A61B 34/30;
(Continued)

(56) References Cited

U.S. PATENT DOCUMENTS 6,610,007 B2 * 8/2003 Belson .................. A61B 1/008
604/95.01
2003/0045778 A1 * 3/2003 Ohline ................ A61B 1/0057
600/114
(Continued)

FOREIGN PATENT DOCUMENTS

CN 104755041 A 7/2015
EP 2446803 A1 * 5/2012 ............ A61B 34/30
(Continued)

OTHER PUBLICATIONS

Extended European Search Report issued by the European Patent Office on Feb. 3, 2023 for the corresponding EP Patent Application No. 22193356.7.

*Primary Examiner* — John R Downey
*Assistant Examiner* — Karmel J Webster
(74) *Attorney, Agent, or Firm* — Stein IP, LLC

(57) ABSTRACT

Provided is a stiffness-reinforced surgical system. A stiffness-reinforced surgical system includes a plurality of links provided rotatably with each other to form a joint device, a main tendon configured to form a traction force for driving the links, an auxiliary tendon configured to form a traction force to resist rotation of the links, and a controller configured to control the traction forces of the main tendon and the auxiliary tendon. According to example embodiment, it is
(Continued)

possible to provide a stiffness-reinforced surgical system configured such that an overtube forms sufficient flexibility while being inserted into the lumen and forms high stiffness during lesion removal, and a control method thereof.

15 Claims, 38 Drawing Sheets

(30) Foreign Application Priority Data

Jun. 15, 2022 (KR) ........................ 10-2022-0072632
Aug. 11, 2022 (KR) ........................ 10-2022-0100796

(52) U.S. Cl.
CPC ............... *A61B 2017/00269* (2013.01); *A61B 2017/00314* (2013.01); *A61B 2017/00323* (2013.01); *A61B 2017/00398* (2013.01); *A61B 2017/00743* (2013.01); *A61B 2034/301* (2016.02)

(58) Field of Classification Search
CPC ........... A61B 2017/00269; A61B 2017/00323; A61B 2017/00743; A61B 34/71; A61B 34/70
See application file for complete search history.

(56) References Cited

U.S. PATENT DOCUMENTS

2007/0043338 A1* 2/2007 Moll ...................... A61B 34/30 606/1
2007/0135803 A1* 6/2007 Belson ............... A61B 1/00154 606/1
2008/0287963 A1* 11/2008 Rogers ................... A61B 1/008 606/130
2010/0160929 A1* 6/2010 Rogers ................... A61B 34/30 606/130
2012/0123200 A1* 5/2012 Rogers ................... A61B 34/30 29/592
2022/0387757 A1* 12/2022 Wang ................ A61M 25/0662

FOREIGN PATENT DOCUMENTS

EP 3248534 A1 11/2017
EP 3791822 A1 * 3/2021 ............. A61B 34/71
JP 2013-244595 A 12/2013
KR 10-2013-0132233 A 12/2013
KR 10-1654031 B1 9/2016
KR 10-2234974 B1 3/2021
KR 10-2021-0115195 A 9/2021
KR 10-2349030 B1 1/2022
WO WO 2007/033379 A2 3/2007
WO WO 2014/046618 A1 3/2014
WO WO 2021/120853 A1 6/2021

* cited by examiner 1000
1
2
272
270
600
240
230
220
230
240
340
312
313
321
322
320
330
311
260
600A
200
250
600B
300

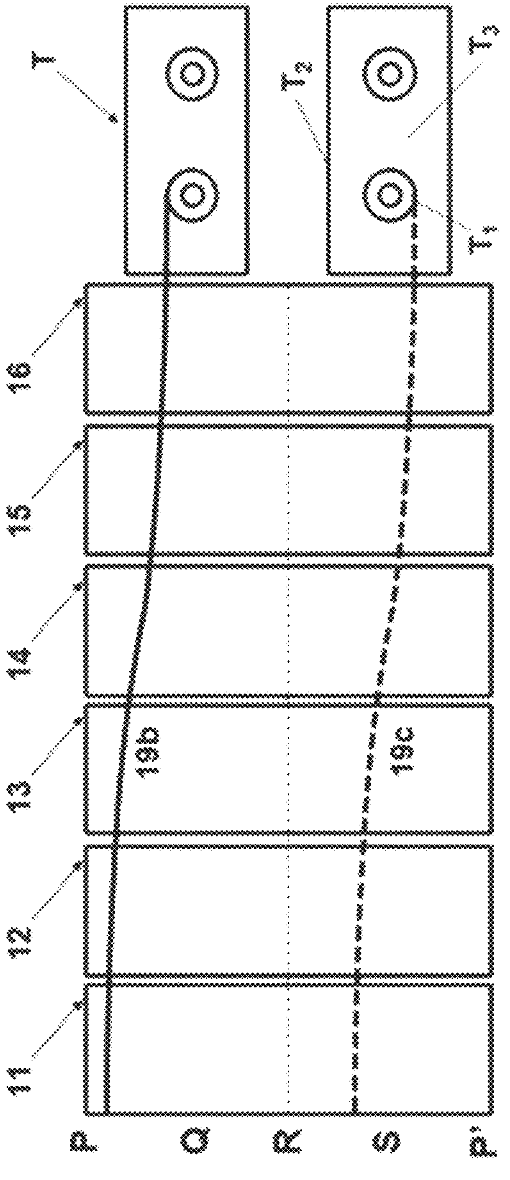
FIG. 23
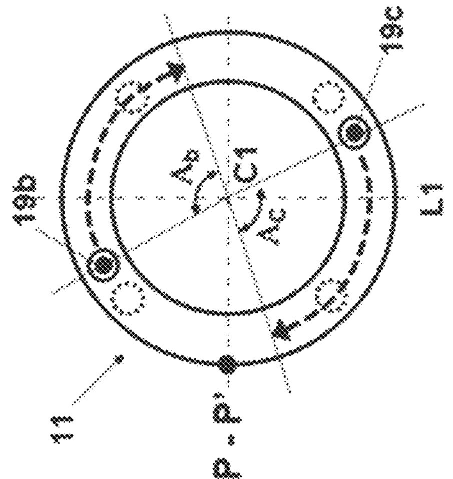

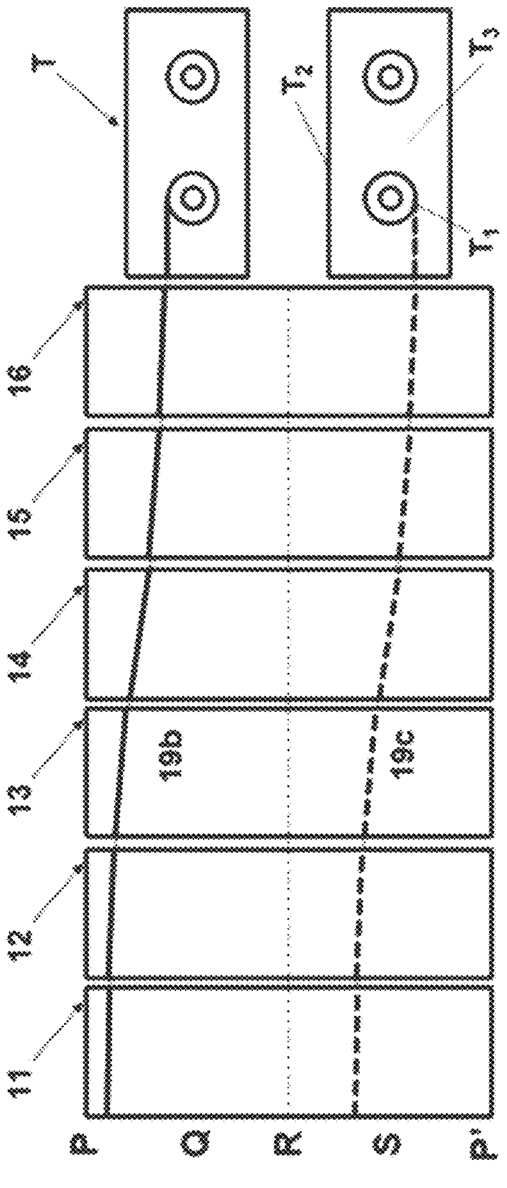
FIG. 24
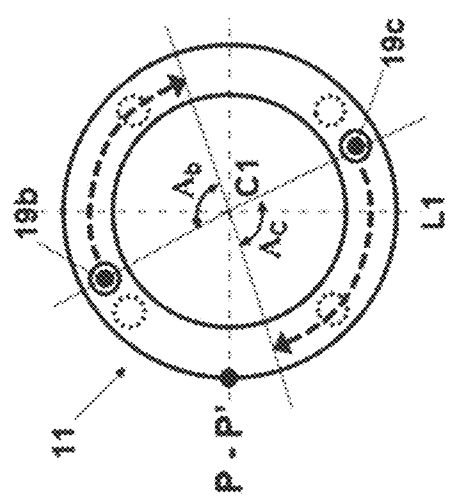

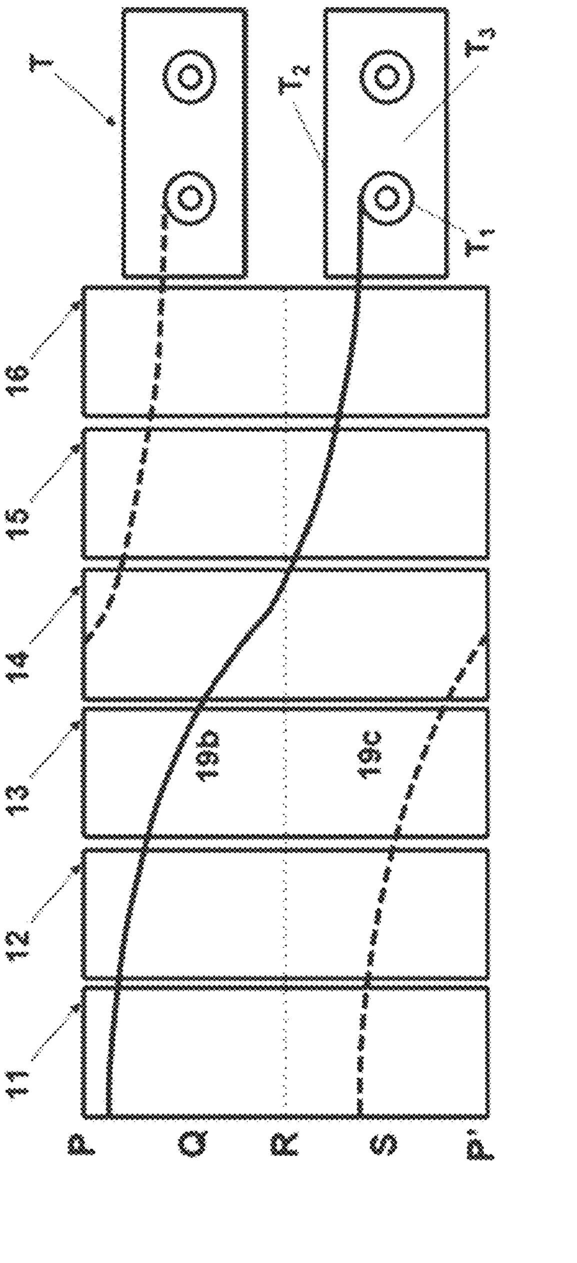
FIG. 25
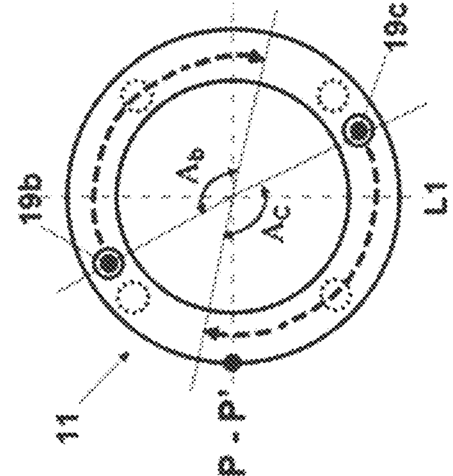

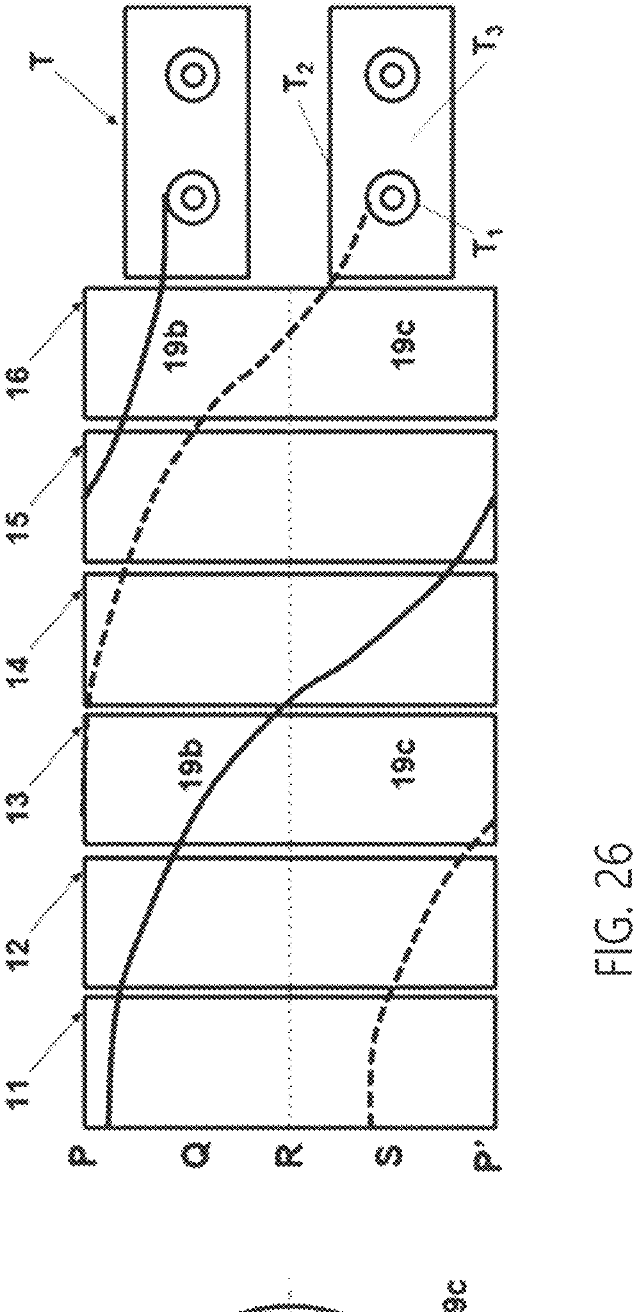
FIG. 26
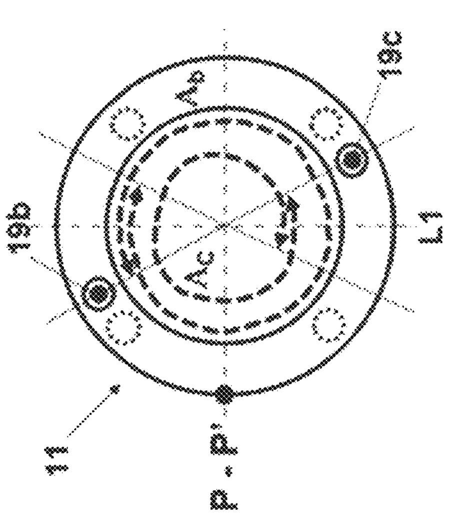

STIFFNESS-REINFORCED SURGICAL SYSTEM AND CONTROL METHOD THEREOF

CROSS-REFERENCE TO RELATED APPLICATION

This application claims the benefit of Korean Patent Application No. 10-2021-0116224 filed on Sep. 1, 2021, and Korean Patent Application No. 10-2022-0072628 filed on Jun. 15, 2022, and Korean Patent Application No. 10-2022-0072632 filed on Jun. 15, 2022, and Korean Patent Application No. 10-2022-0100796 filed on Aug. 11, 2022, in the Korean Intellectual Property Office. This application also claims the benefit of U.S. Provisional Application No. 63/342,955 filed on May 17, 2022, in the U.S. Patent and Trademark Office. The entire disclosures of which are incorporated herein by reference for all purposes.

BACKGROUND

1. Field of the Invention

One or more example embodiments relate to a stiffness-reinforced surgical system and a control method thereof, and more particularly, to a stiffness-reinforced surgical system configured to increase stiffness of an overtube during lesion treatment and a control method thereof.

2. Description of the Related Art

In early detection of gastrointestinal cancer, an importance of endoscopic resection to remove an affected area with an endoscope equipped with a surgical knife is emerging. Endoscopic resection includes endoscopic mucosal resection and endoscopic submucosal dissection.

Early gastrointestinal cancer and gastrointestinal polyps that can develop into cancer can be treated with endoscopic resection, and the 5-year survival rate is nearly 100% when diagnosed and treated early. Endoscopic resection has the advantage of shortening the recovery period by reducing the strain on the patient's body compared to the existing surgical method that approaches the affected area by incising the skin.

Removal of large, flat polyps is a difficult and time-consuming task. There are results of pre-clinical studies that show that when tension is applied to lesion tissue through a surgical tool during endoscopic resection, the polyp can be removed quickly and safely. Based on these research results, various endoscopic surgical robot devices equipped with surgical tools are being developed.

An overtube should be sufficiently flexible during insertion into the lumen, but is required to have high stiffness so that the surgical tool may apply sufficient tension to the tissue after reaching a target lesion. Therefore, studies are being actively conducted on a device in which an overtube forms sufficient flexibility while being inserted into the lumen and forms high stiffness during lesion removal, and a control method thereof.

SUMMARY

Example embodiments provide a stiffness-reinforced surgical system configured such that an overtube forms sufficient flexibility while being inserted into the lumen and forms high stiffness during lesion removal, and a control method thereof.

According to an aspect, there is provided a stiffness-reinforced surgical system including a plurality of links provided rotatably with each other to form a joint device, a main tendon configured to form a traction force for driving the links, an auxiliary tendon configured to form a traction force to resist rotation of the links, and a controller configured to control the traction forces of the main tendon and the auxiliary tendon.

The controller may include a slider to which the main tendon is coupled, the slider being movably coupled to a rail, a first driver configured to move the slider along the rail, a first capstan on which the auxiliary tendon is wound, and a second driver configured to rotate the first capstan.

The controller may include a second capstan coupled to the same axis as the first capstan and on which a second wire is wound, and a second balance spring configured to pull the second wire so that the auxiliary tendon forms tension.

The second driver may include a motor, and an electronic clutch configured to selectively connect a shaft of the motor and a shaft of the first capstan.

The controller may include a first balance spring configured to pull a first wire connected to the slider so that the main tendon forms tension.

The first driver may include a linear actuator.

The controller may include a first body to which the rail is fixed and to which a shaft of the first capstan is rotatably coupled, and a second body to which the first driver and the second driver are coupled, the second body being detachably coupled to the first body, and when the first body and the second body are coupled, the slider and the first driver may be coupled by a first coupler, and the shaft of the first capstan and a shaft of the second driver may be coupled by a second coupler.

The main tendon and the auxiliary tendon may be configured to pass through the inside of the links, and a path of the auxiliary tendon may incline in an 'S' shape.

The main tendon and the auxiliary tendon may be configured to pass through the inside of the links, and some of paths of the auxiliary tendon may incline.

A plurality of the auxiliary tendons may be provided, and a path of one of the auxiliary tendons and a path of another auxiliary tendons of the auxiliary tendons may be symmetrical to each other with respect to a centerline of the links.

According to another aspect, there is provided a control method of the stiffness-reinforced surgical system including pulling the main tendon to move the joint device to a lesion in a human body, and pulling the auxiliary tendon to increase stiffness of the joint device.

The auxiliary tendon may include a first auxiliary tendon and a second auxiliary tendon, and the pulling of the auxiliary tendon may include pulling the first auxiliary tendon to prevent deflection of the joint device, and pulling the second auxiliary tendon so as to prevent torsion of the joint device due to the pulling of the first auxiliary tendon.

The control method may further include maintaining a traction force of the auxiliary tendon, treating the lesion by driving a surgical robot provided in a lumen of the joint device, releasing the traction force of the auxiliary tendon, and pulling the main tendon so that the joint device is retracted from the lesion.

The treating of the lesion may include changing a traction force applied to the main tendon so that a position of the joint device is controlled in a state where a predetermined traction force is maintained on the auxiliary tendon.

The releasing of the traction force of the auxiliary tendon may include releasing the traction force of the second auxiliary tendon, and releasing the traction force of the first auxiliary tendon.

Additional aspects of example embodiments will be set forth in part in the description which follows and, in part, will be apparent from the description, or may be learned by practice of the disclosure.

According to example embodiments, it is possible to provide a stiffness-reinforced surgical system configured such that a controller controls traction forces of the main tendon and the auxiliary tendon, so that the overtube forms sufficient flexibility while being inserted into the lumen and forms high stiffness during lesion removal.

In addition, according to example embodiments, it is possible to provide a control method of a stiffness-reinforced surgical system configured such that the overtube forms sufficient flexibility while being inserted into the lumen and forms high stiffness during lesion removal, by including pulling the main tendon to move a joint device to the lesion in the human body and pulling the auxiliary tendon to increase the stiffness of the joint device.

BRIEF DESCRIPTION OF THE DRAWINGS

These and/or other aspects, features, and advantages of the invention will become apparent and more readily appreciated from the following description of example embodiments, taken in conjunction with the accompanying drawings of which:

FIG. 23 is a virtual development view in which a virtual outer surface of the device of FIG. 22 in which a curved auxiliary tendon hole is installed is cut;

FIG. 24 is a virtual development view in which a virtual outer surface of the device of FIG. 22 in which a diagonal auxiliary tendon hole is installed is cut;

FIG. 25 is a diagram illustrating a case in which auxiliary tendons are located on both upper and lower portions of the virtual outer surface in FIG. 23 and FIG. 24;

FIG. 26 illustrates an example of a case in which an “S” angle of each auxiliary tendon is greater than 360°;

DETAILED DESCRIPTION

Hereinafter, preferred example embodiments will be described in detail with reference to the accompanying drawings. However, in describing example embodiments, descriptions of already-known functions or configurations will be omitted in order to clarify the present disclosure.

A stiffness-reinforced surgical system and a control method thereof according to example embodiments are configured such that an overtube forms sufficient flexibility while being inserted into a lumen and forms high stiffness during lesion removal.

Figure 1:
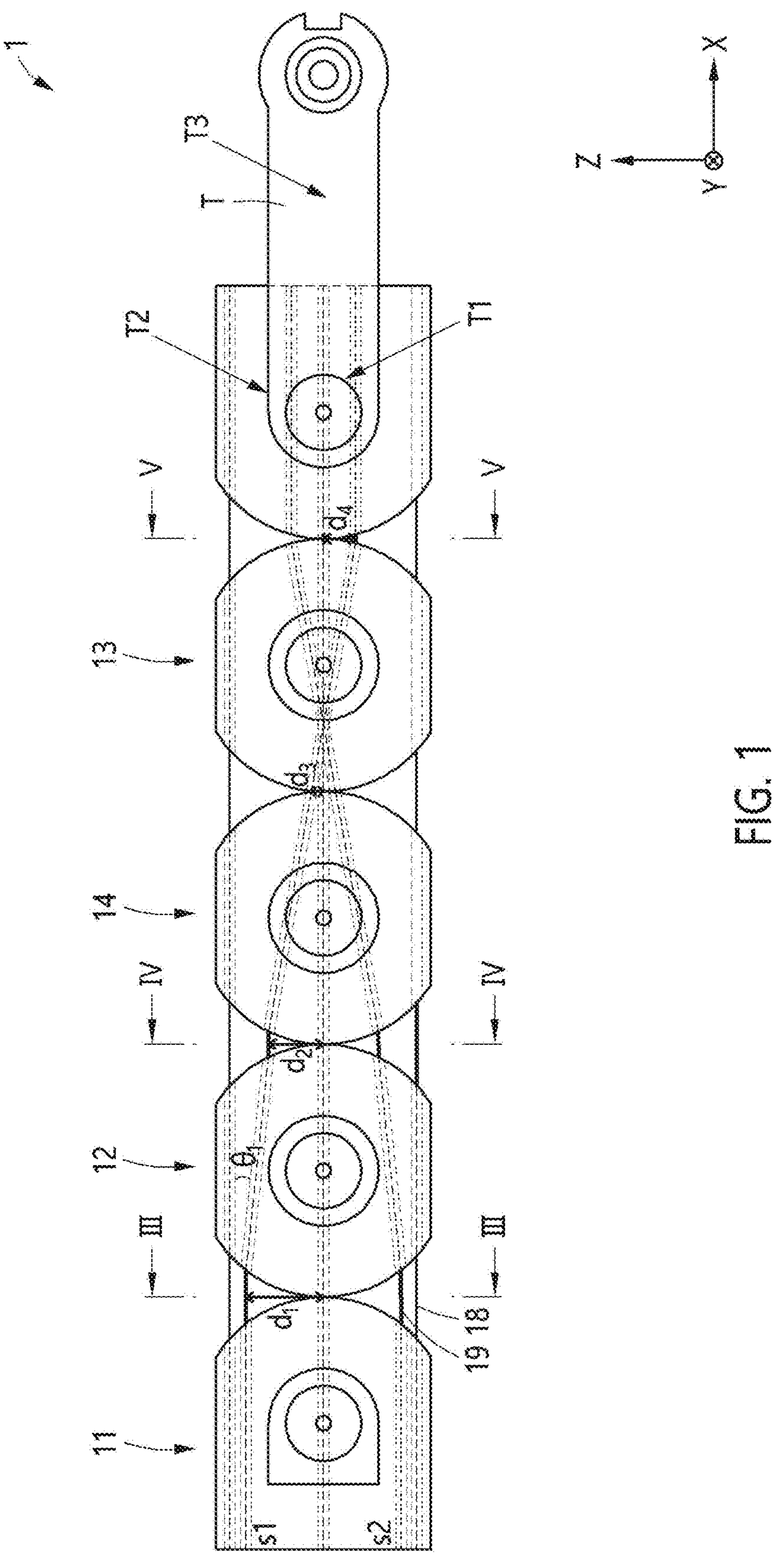
FIG. 1 is a side view illustrating a surgical device having an auxiliary tendon according to an example embodiment.
Figure 2:
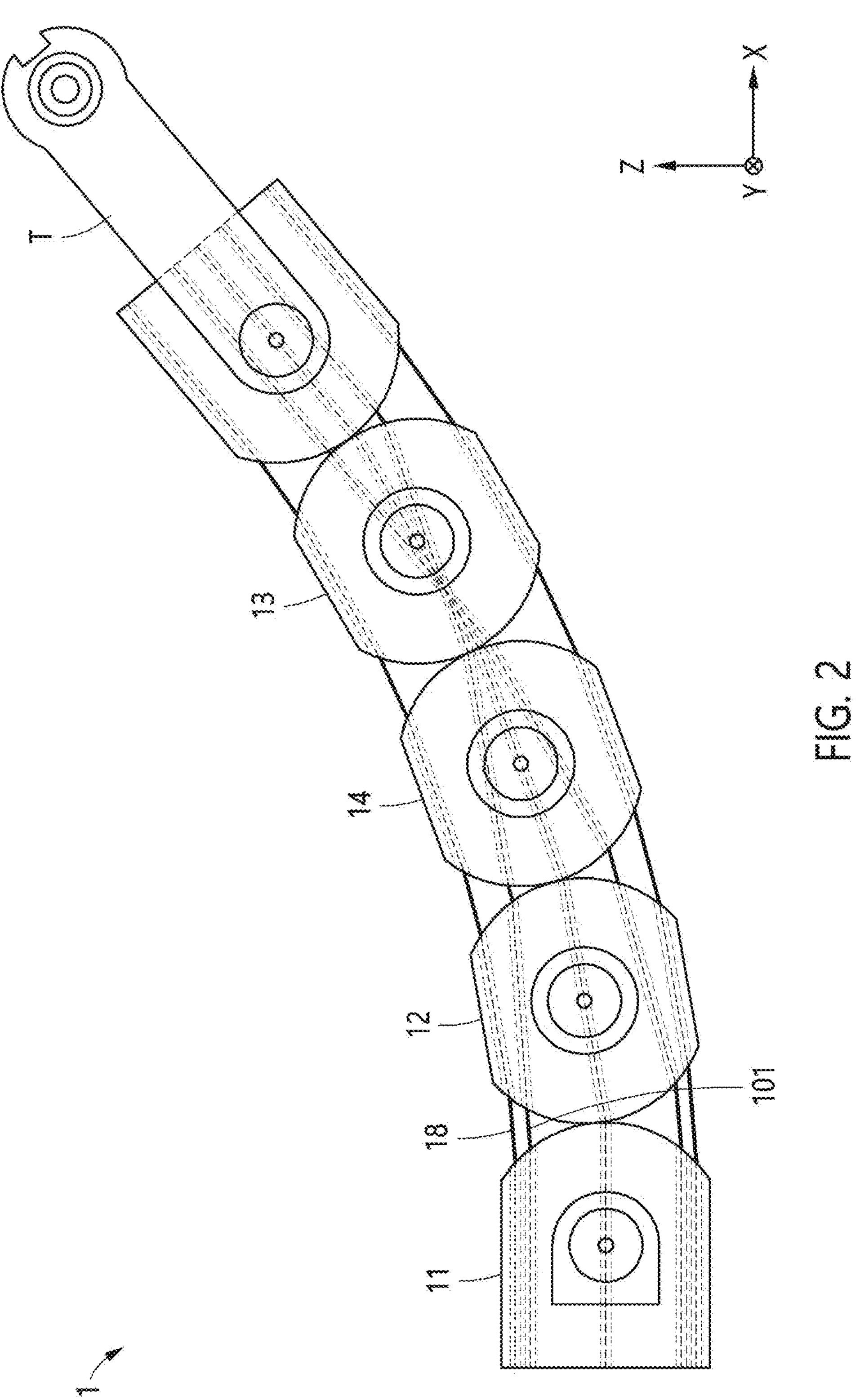
FIG. 2 is a side view illustrating a deformed state of the surgical device of FIG. 1.

FIG. 1 is a side view of a surgical device having an auxiliary tendon according to an example embodiment, and FIG. 2 is a side view showing a deformed state of the surgical device of FIG. 1.

Figure 3:
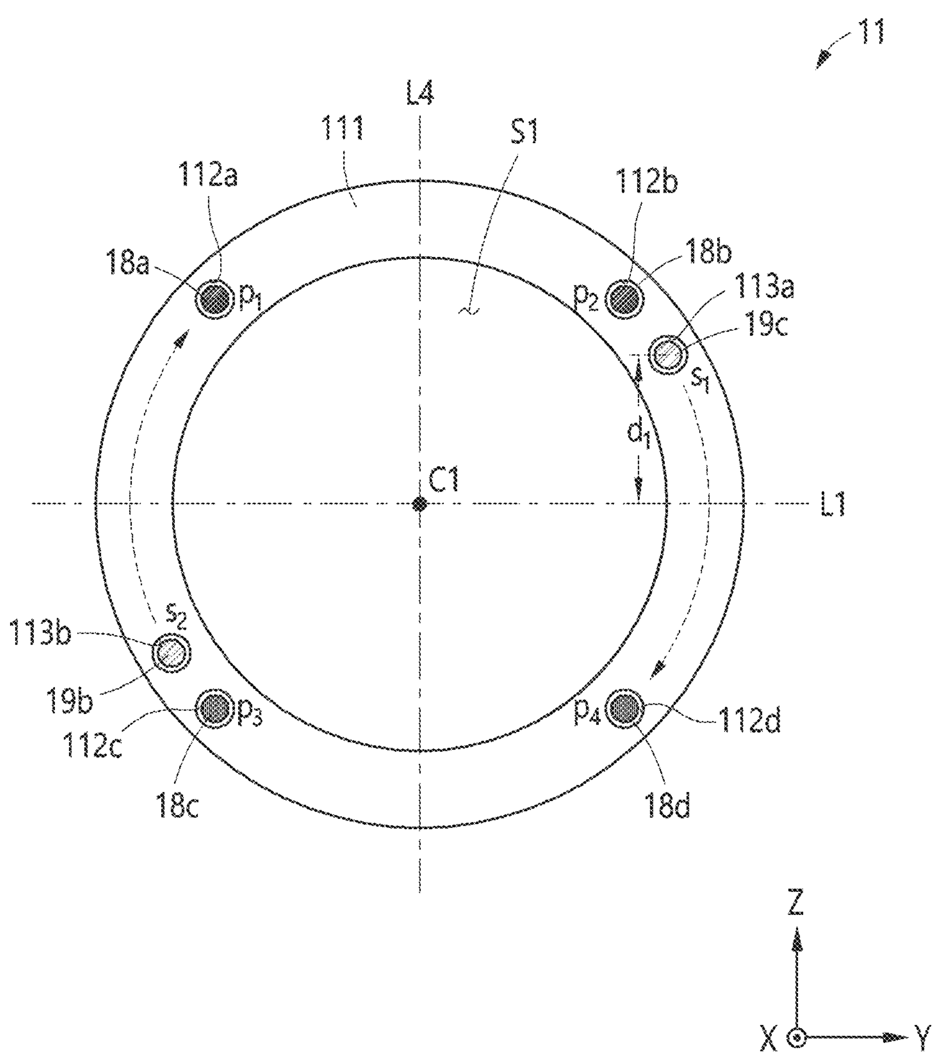
FIG. 3 is a cross-sectional view taken along the cut line of FIG. 1.
Figure 4:
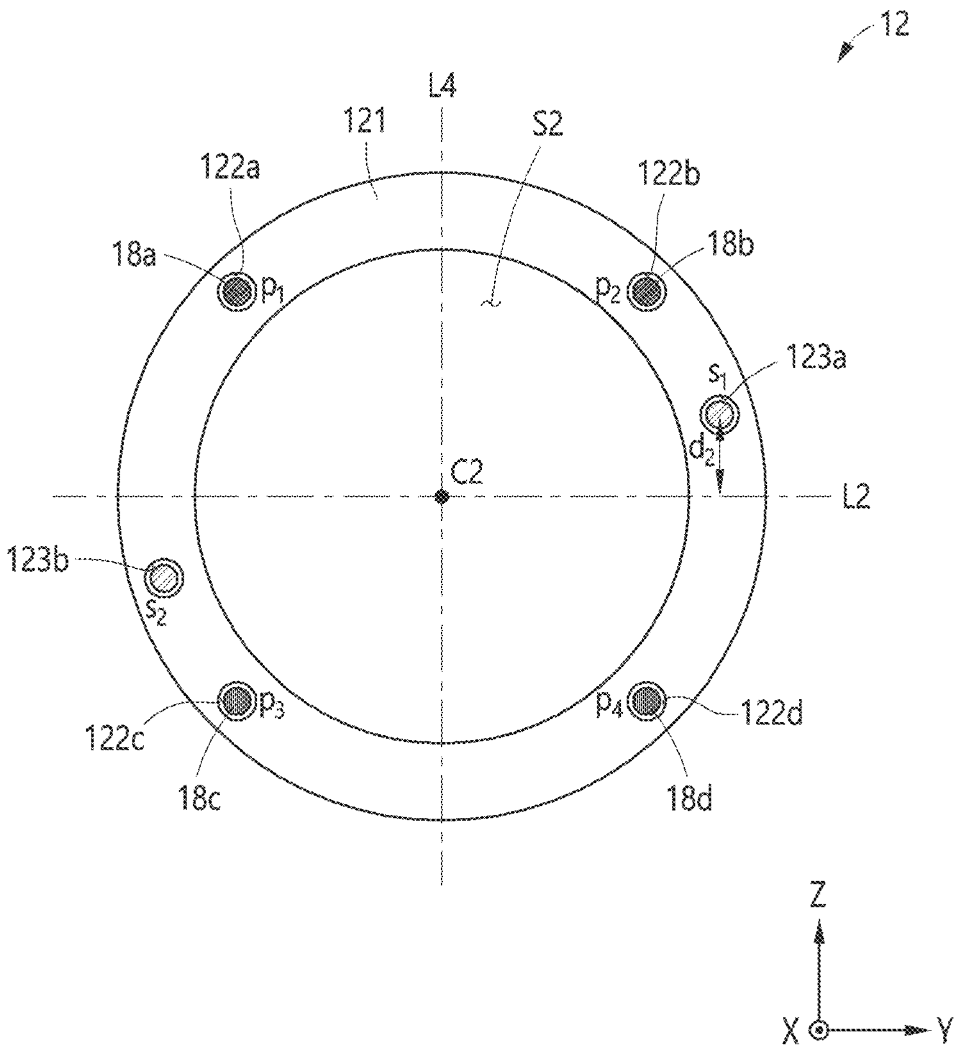
FIG. 4 is a cross-sectional view taken along the cut line IV-IV of FIG. 1.
Figure 5:
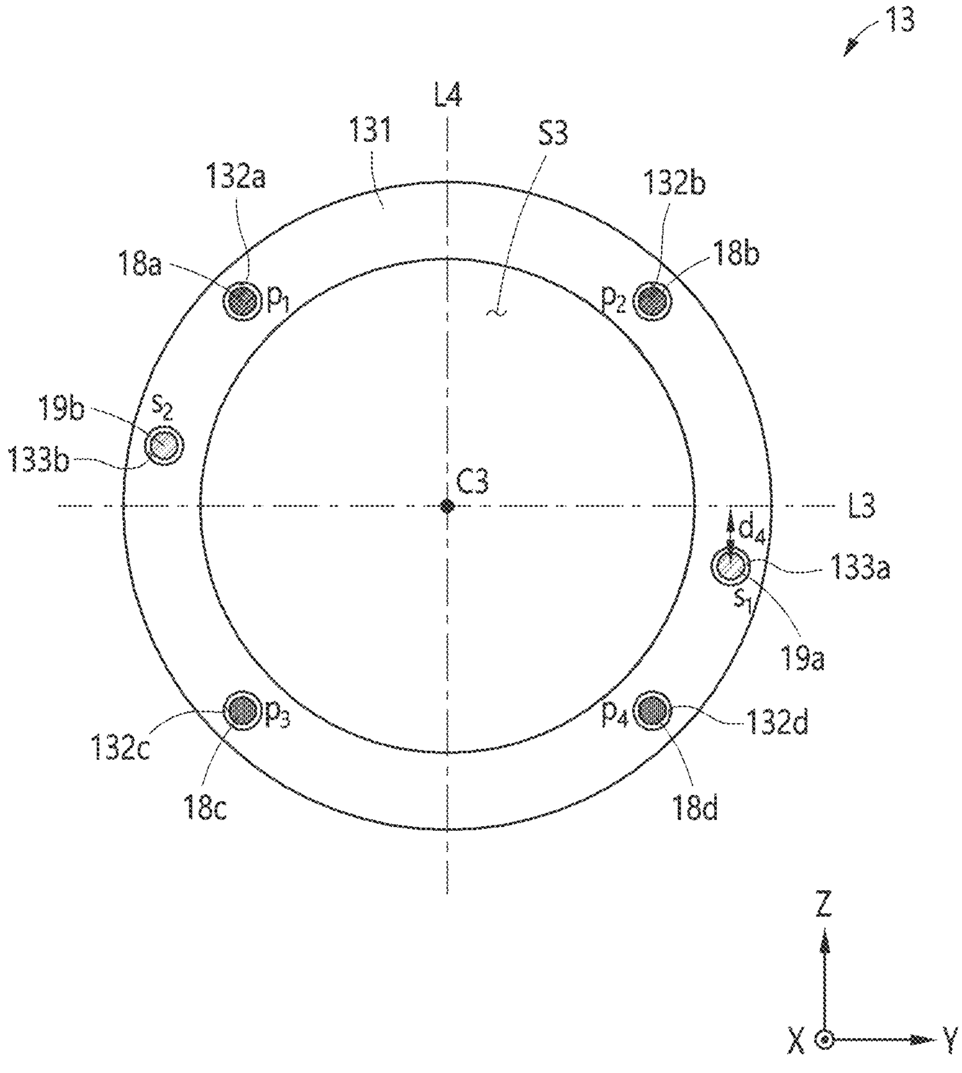
FIG. 5 is a cross-sectional view taken along the cut line V-V of FIG. 1.

FIG. 3 is a cross-sectional view taken along the cut line of FIG. 1, FIG. 4 is a cross-sectional view taken along the cut line IV-IV of FIG. 1, and FIG. 5 is a cross-sectional view taken along the cut line V-V of FIG. 1.

Referring to FIG. 1 and FIG. 2, a surgical device 1 having an auxiliary tendon (hereinafter, referred to as a "surgical device") may include a plurality of links rotatably connected to each other.

The surgical device 1 may include a first (joint) link 11 and a second (joint) link 12 rotatably connected to the first link 11, and at least one connecting link 14 rotatably connected to the second link 12, and a third (joint) link 13 rotatably connected to the connecting link 14.

In the drawings, one connection link 14 is shown, but the number is not limited thereto. In addition, the connection link 14 may be the same as the first link 11, the second link 12, and the third link 13 only expressed as a connection link in expression.

However, the plurality of links may each have the same size or shape. However, the size or shape of one or more links may be different from the size or shape of the other links. For example, two or more links may have the same thickness or height, but may have different lengths or shapes.

The surgical device 1 may include a tip T capable of working a target site. The surgical device 1, the longitudinal direction may be provided in the x-axis direction. However, the size or shape of the tip T may be different depending on the target site, the type of surgery, and the like. However, in general, the thickness of the tip is the same as the thickness of the link or smaller than the thickness of the link, so that the overtube may be smoothly inserted into the lumen.

The surgical device 1 may include (mainly) one or more main tendons 18 for rotating the plurality of links, and one or more auxiliary tendons 19 for (mainly) improving stiffness.

As will be described below, the user may improve the stiffness of one or more links by manipulating only the main tendon according to the installation position, angle, etc. of the main tendon. Alternatively, the user may rotate one or more links by manipulating only the auxiliary tendons.

Auxiliary tendons may have one or more auxiliary tendons and one or more roll-minimizing auxiliary tendons. The main tendon 18 and the auxiliary tendon 19, which are tendons having a material or structure capable of transmitting tensile or compressive force, may have a wire shape, for example. Accordingly, the direction and position of the surgical device or tip may be changed according to the traction of the wire.

FIG. 3 to FIG. 5, the main tendon 18 is 4 and the auxiliary tendon 19 is 2, but the number is not limited thereto.

For example, when the tension of the main tendons 18*a* and 18*b* located in the +z direction is increased, the shape of the surgical device 1 may be changed so that the tip T is directed in the +z direction. When the tension of the main tendons 18*c* and 18*d* located in the −z direction increases, the shape of the surgical device 1 may be changed so that the tip T is directed in the −z direction.

As described above, the auxiliary tendon 19 may have a material or structure capable of transmitting a tensile force or a compressive force, if necessary, may include a material having elasticity or may be manufactured in a structure having elasticity. The auxiliary tendon 19 may assist so that the shape of the surgical device 1 does not change unintentionally while an external force is applied to the tip T.

FIG. 3 to FIG. 5, the first link 11 includes a first link body 111, first main tendon holes 112*a*, 112*b*, 112*c*, and 112*d* penetratingly formed in the first link body 111, and first auxiliary tendon holes 113*a* and 113*b* formed through the first link body 111 and spaced apart from the first main tendon holes 112*a*, 112*b*, 112*c*, and 112*d*.

The first link body 111 may include a first hollow S1 therein. The first hollow S1 may guide various surgical powers and/or cameras. For example, the first link body 111 may have a hollow pillar shape. The first link body 111 may form a symmetrical shape about a central axis C1.

The first main tendon holes 112*a*, 112*b*, 112*c*, and 112*d* may be formed through the first link body 111 in the longitudinal direction (x-axis direction) of the first link body 111. A total of four first main tendon holes 112*a*, 112*b*, 112*c*, and 112*d* may be provided and may be spaced apart from each other in the circumferential direction. In addition, the first main tendon holes 112*a*-112*d* may be symmetrically or asymmetrically spaced apart from each other by 90 degrees or different angles in the circumferential direction with respect to the central axis C1. Also, the number of the first main tendon holes is not limited thereto.

The first auxiliary tendon holes 113*a* and 113*b* may be formed through the first link body 111 in the longitudinal direction (x-axis direction) of the first link body 111. A total of two first auxiliary tendon holes 113*a* and 113*b* may be provided and may be spaced apart from each other in the circumferential direction.

The number of the first main tendon holes is not limited thereto. The first auxiliary tendon holes 113*a* and 113*b* may be provided at positions spaced apart from the first main tendon holes 112*a*, 112*b*, 112*c*, and 112*d*. However, the first auxiliary tendon holes 113*a* and 113*b* may be symmetrically or asymmetrically spaced apart by 180° in the circumferential direction with respect to the central axis C1 or according to different angles. In addition, each of the first auxiliary tendon holes 113*a* and 113*b* may be spaced apart from one of the first main tendon holes 112*a*-112*d* closest thereto at the same or different angles in the circumferential direction.

For example, the first auxiliary tendon hole 113*a* may be spaced apart from the auxiliary line L1 perpendicular to the central axis C1 by a first distance d1 or an angle corresponding thereto.

The second link 12 includes a second link body 121, second main tendon holes 122*a*, 122*b*, 122*c*, 122*d* penetratingly formed in the second link body 121, and second auxiliary tendon holes 123*a* and 123*b* penetratingly formed in the second link body 121 and positioned apart from the second main tendon holes 122*a*, 122*b*, 122*c*, and 122*d*.

The second link body 121 may include a second hollow S2 therein. The second hollow S2 may guide various surgical powers and/or cameras. For example, the second link body 121 may have a hollow pillar shape. The second link body 121 may have a symmetrical shape about a central axis C2.

In a state in which the first link body 111 and the second link body 121 are side by side (that is, the central axis C1 and the central axis C2 are the same straight line), the main tendons 18*a*-18*d* are parallel to the first link body 111 and the second link body 121 is installed through it. Accordingly, the first main tendon holes 112*a*, 112*b*, 112*c*, 112*d* and the second main tendon holes 122*a*, 122*b*, 122*c*, 122*d* may overlap each other along the x-axis direction that is the longitudinal direction of the first link body 111.

On the other hand, when the main tendons 18*a*-18*d* are installed to have a slight angle with the central axes C1 and C2, the first main tendon hole and the second main tendon hole may be manufactured to overlap each other in the x-axis direction, or to be spaced apart from each other by a slight angle or a small distance.

Unlike the main tendon 18, the auxiliary tendon 19 is generally installed to be inclined to the central axes C1 and C2. Therefore, in a state in which the first link body 111 and the second link body 121 are parallel to each other, the first auxiliary tendon holes 113*a*, 113*b* and the second auxiliary tendon holes 123*a*, 123*b* may not overlap each other along the x-axis direction, which is the longitudinal direction of the first link body 111.

The second main tendon holes 122*a*, 122*b*, 122*c*, 122*d* may be formed through the second link body 121 in the longitudinal direction (x-axis direction) of the second link body 121. A total of four second main tendon holes 122*a*, 122*b*, 122*c*, 122*d* may be provided and may be spaced apart from each other in the circumferential direction. The number of the second main tendon holes is not limited thereto.

The second auxiliary tendon holes 123*a*, 123*b* may be formed through the second link body 121 in the longitudinal direction (x-axis direction) of the second link body 121. A total of two second auxiliary tendon holes 123*a*, 123*b* are provided, and may be spaced apart from each other in the circumferential direction.

The number of the second main tendon holes is not limited thereto. The second auxiliary tendon holes 123*a*, 123*b* may be provided at positions spaced apart from the second main tendon holes 122*a*, 122*b*, 122*c*, 122*d*.

The second main tendon holes 122*a*, 122*b*, 122*c*, 122*d* may be formed parallel to the longitudinal direction of the second link body 121, and the second auxiliary tendon holes 123*a*, 123*b* may be formed inclined with respect to the longitudinal direction of the second link body 121.

As shown in FIG. 1, the auxiliary tendon hole of each of the second link 12, the connecting link 14, and the third link 13 is provided to be inclined with the longitudinal direction of the surgical device 1, so that the auxiliary tendon 19 may be inclined in an approximately 'S' shape.

In addition, a plurality of the auxiliary tendon 19 is provided, and any one of the auxiliary tendons 19 and the other path may be symmetrical with respect to the center lines C1, C2, C3 of the links 11, 12, 13, 14.

Figure 12:
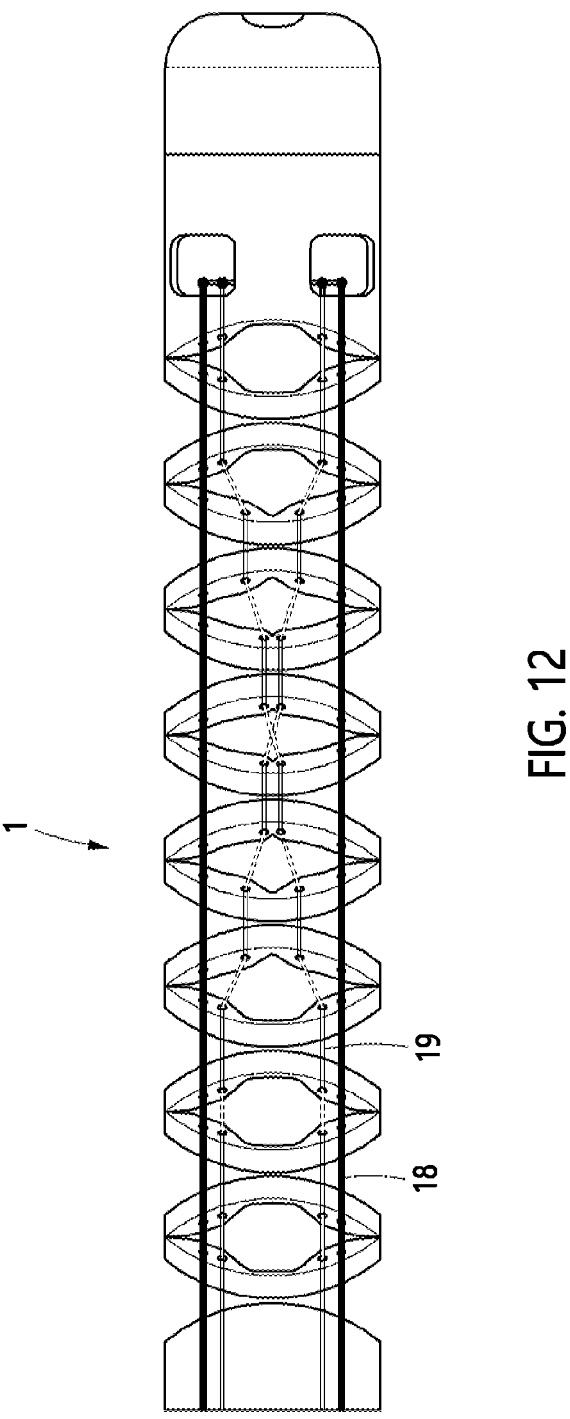
FIG. 12 is a diagram illustrating a stepped ‘S’-shaped path of an auxiliary tendon.

In addition, as another example, as shown in FIG. 12, the auxiliary tendon hole formed in each link is formed parallel to the longitudinal direction of the link body (that is, when passing through the auxiliary tendon holes, the auxiliary tendon passes parallel to the longitudinal direction of the link body), and the auxiliary tendon hole of the adjacent link is disposed at a different distance from the central axis, so that at least portion of the auxiliary tendon 19 may be inclined in an approximately 'S' shape.

The "S" shape may mean various shapes. For example, the "S" shape may refer to a sigmoid shape. Alternatively, the "S" shape may have a shape similar to the letter S, in which at least one of both ends of the sigmoid is curved toward the center of the sigmoid.

Alternatively, the "S" shape may mean a combination of a plurality of short straight lines having a shape similar to the sigmoid or letter S, a combination of a plurality of short curves, or a combination of a plurality of straight lines and curves. In particular, in this case, two straight lines, two curves, or a straight line and a curve adjacent to each other may be connected to each other, may be spaced apart by some distance or angle, or may have a stepped shape.

For convenience of description, in this specification, the "S" shape refers to one or more of the various shapes of the above two paragraphs.

In addition, unless otherwise specified, the "S" shape in the present specification means a shape on the side view as shown in FIG. 1 and FIG. 2. Therefore, the "S" shape on the first link body to the third link body 111-113 and the outer surface of the connecting link 14 in a two-dimensional unfolded view is different from the "S" shape on the side view such as FIG. 1 and FIG. 2.

The second auxiliary tendon hole 123*a* may be spaced apart from the auxiliary line L2 perpendicular to the central axis C2 by a second distance d2. The first distance d1 from the auxiliary line L1 intersecting the central axis C1 of the first link body 111 to the first auxiliary tendon hole 113*a* may be greater than the second distance d2 from the auxiliary line L2 intersecting the central axis C2 of the second link body 121 to the second auxiliary tendon hole 123*a*.

In addition, the second main tendon holes 122*a*-122*d* and the second auxiliary tendon holes 123*a*, 123*b* may have a similar structure or may be installed at a similar angle to the first main tendon holes 112*a*-112*d* and the first auxiliary tendon holes 113*a*, 113*b* as illustrated in FIG. 4.

The third link 13 may include a third link body 131, third main tendon holes 132*a*, 132*b*, 132*c*, 132*d* that are formed through the third link body 131, and third auxiliary tendon holes 133*a* and 133*b* is formed through the third link body and is spaced apart from the third main tendon holes 132*a*, 132*b*, 132*c*, and 132*d*.

The third link body 131 may include a third hollow S3 therein. The third hollow S3 may guide various surgical powers and/or cameras. For example, the third link body 131 may have a hollow pillar shape. The third link body 131 may have a symmetrical shape about the central axis C3.

The third main tendon holes 132*a*, 132*b*, 132*c*, 132*d* may be formed through the third link body 131 in the longitudinal direction (x-axis direction) of the third link body 131. A total of four third main tendon holes 132*a*, 132*b*, 132*c*, 132*d* may be provided and may be spaced apart from each other in the circumferential direction. The number of the third main tendon holes is not limited thereto.

The third auxiliary tendon holes 133*a*, 133*b* may be formed through the third link body 131 in the longitudinal direction (x-axis direction) of the third link body 131. A total of two third auxiliary tendon holes 133*a*, 133*b* may be provided and may be spaced apart from each other in the circumferential direction.

The number of the third main tendon holes is not limited thereto. The third auxiliary tendon holes 133*a*, 133*b* may be provided at positions spaced apart from the third main tendon holes 132*a*, 132*b*, 132*c*, 132*d*.

The third auxiliary tendon hole 133*a* may be spaced apart from the auxiliary line L3 perpendicular to the central axis C3 by a third distance d4. The second distance d2 from the auxiliary line L2 intersecting the central axis C2 of the second link body 121 to the second auxiliary tendon hole 123*a* may be greater than the third distance d4 from the auxiliary line L3 intersecting the center axis C3 of the third link body 131 to the third auxiliary tendon hole 133*a*.

A direction (+z direction) in which the second auxiliary tendon hole 123*a* is spaced apart from the auxiliary line L2 intersecting the central axis C2 of the second link body 121 is opposite to the direction (−z direction) in which the third auxiliary tendon hole 133*a* is spaced apart from the auxiliary line L3 intersecting the axis C3 of the third link body 131.

However, as described above, the auxiliary tendons 19*a*, 19*b* are generally installed to be inclined to the central axis C1-C3. Accordingly, the sizes and directions of the first distance d1, the second distance d2, and the third distance d3 may be different depending on the number of auxiliary tendons 19*a*, 19*b*, installation directions, and the like.

At least one connection link 14 may be provided between the second link body 121 and the third link body 131. The shape of the at least one connecting link 14 may be the same as or different from that of the first link 11, the second link 12, or the third link 13.

The main tendons 18*a*, 18*b*, 18*c*, 18*d* may pass through the first main tendon holes 112*a*, 112*b*, 112*c*, 112*d*, the second main tendon holes 122*a*, 122*b*, 122*c*, 122*d*, and the third main tendon hole 132*a*, 132*b*, 132*c*, 132*d*.

One end of each of the main tendons 18*a*, 18*b*, 18*c*, 18*d* may be fixed to an end to which the tip T is connected. The user may rotate the surgical device 1 by applying an appropriate tension to the main tendons 18*a*, 18*b*, 18*c*, 18*d*.

However, the main tendons 18*a*-18*d* may be fixed to various parts of the tip T according to the shape and size of the tip T. For example, the main tendon 18*a*-18*d* may be fixed to T1 which is a connection portion between the tip and the third link 13, T2 which is the outer surface of the tip, and T3 which is the inner surface of the tip. In addition, as described below, the "S" shape of the auxiliary tendons 19*a*, 19*b* may also be different depending on the position of the portion where the main tendon 18*a*-18*d* is fixed to the tip.

The auxiliary tendons 19*a*, 19*b* may pass through the first auxiliary tendon holes 113*a*, 113*b*, the second auxiliary tendon holes 123*a*, 123*b*, and the third auxiliary tendon holes 133*a*, 133*b*.

When the first link body 111 and the second link body 121 are side by side, the auxiliary tendons 19*a*, 19*b* may be provided to be inclined with respect to the central axis C1 of the first link body between the first auxiliary tendon holes 113*a*, 113*b* and the second auxiliary tendon holes 123*a*, 123*b*. The auxiliary tendons 19*a*, 19*b* may have elasticity, and if desired, may have some degree of elasticity.

Based on the state in which the first link 11, the second link 12, the third link 13, and the connection link 14 are provided side by side, the main tendons 18*a*, 18*b*, 18*c*, 18*d* may be installed in parallel with the length direction of one or more of the first to the third link 11-13, at least a portion of the auxiliary tendons 19*a*, 19*b* may be provided to be inclined with respect to the longitudinal direction of the first to third links 11-13.

Figure 6:
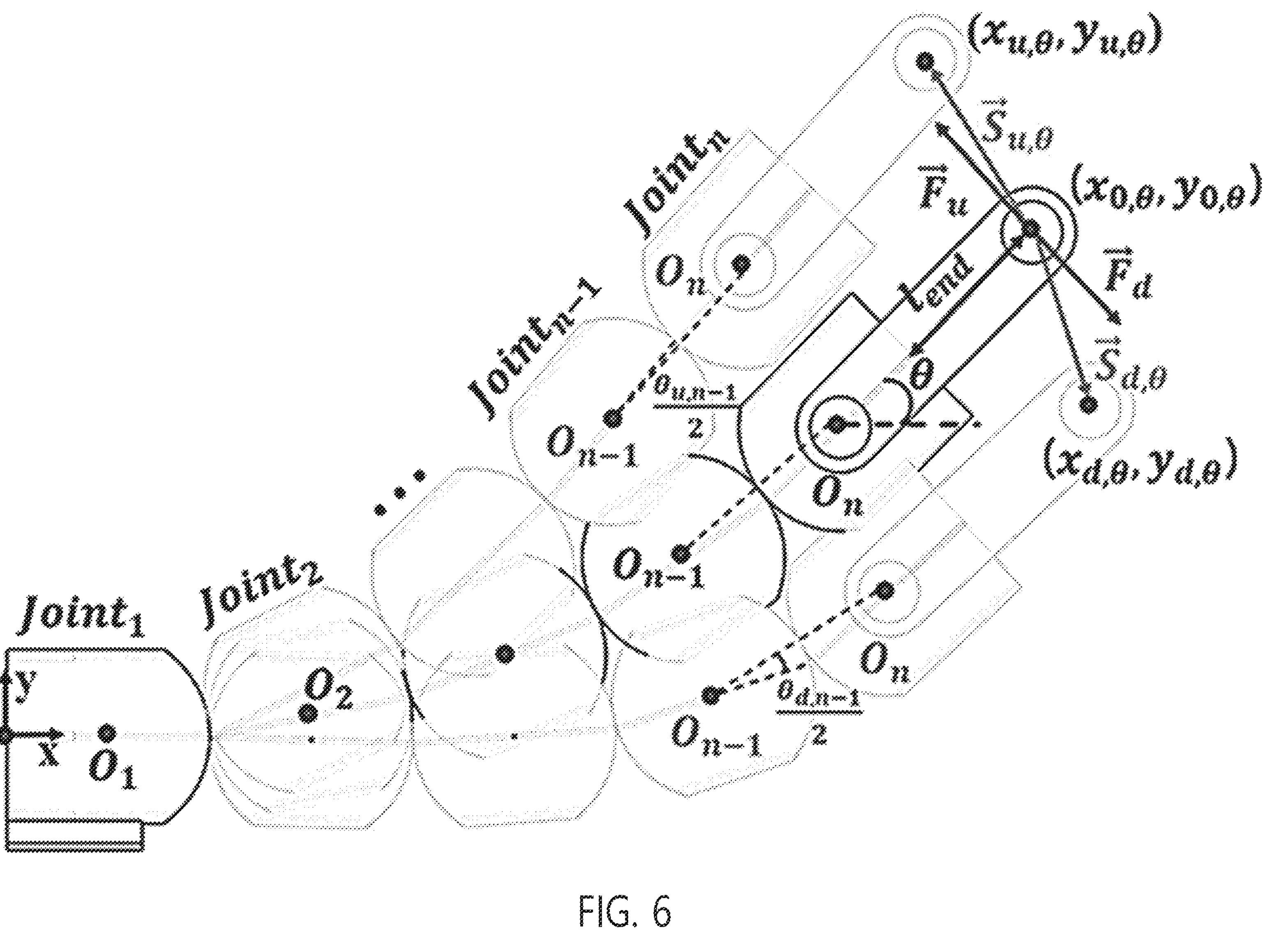
FIG. 6 is a diagram illustrating shape deformation of an overtube having n rolling joints due to an external force.

A path of the auxiliary tendon 19 installed along a plurality of links, for example, the first to third links 11-13 may be optimized as follows. Referring to FIG. 6, the purpose of the optimization is to define the path of the auxiliary tendon 19 to minimize the sum of the position changes $|S_{d,\theta}|$ and $|S_{u,\theta}|$ caused by the downward force $F_d$ and the upward force $F_u$.

FIG. 6 shows that a 1 DOF (single degree of freedom system) overtube composed of n rolling joints is deflected by an external force. $O_i$(i=1, . . . n) is the center of rotation of each joint (link), and $l_{end}$ is defined considering that the surgical tool is not covered from the overtube to perform the operation in the clinical environment.

External forces $F_d$ and $F_u$ are generally defined in consideration of the direction of tension applied to the lesion by the surgical tool mounted on the end tip when counter traction is perpendicular to the end tip, which is the end of the overtube.

$(x_{0,\theta}, y_{0,\theta})$ is the initial position when the end tip has an arbitrary angle θ, $(x_{d,\theta}, y_{d,\theta})$ and $(x_{u,\theta}, y_{u,\theta})$ are the end tip positions deflected by each external force. $\theta_{d,n-1}$ and $\theta_{u,n-1}$ are the relative angles between $\text{Joint}_{n-1}$ and $\text{Joint}_n$ after being deflected by an angular external force.

To perform the optimization, it is necessary to calculate the amount of change in the position of the end tip due to an external force. Considering that the overall structural stiffness of the overtube with rolling joints determines the shape of the internal tendon, and the overtube is deflected by the extension of the tendon, work by external forces is assumed to be stored as the elastic deformation energy of the tendon.

The minimum total potential energy principle was used for the analysis of the entire system. In other words, the overtube will be deflected by an external force in a direction that minimizes the total potential energy. $W_d$ and $W_u$ are work performed by external forces $F_d$ and $F_u$, respectively, and are defined as follows.

$$W_d=\int \vec{F}_d \cdot d\vec{S}_{d,\theta} \quad \text{[Equation 1]}$$

$$W_u=\int \vec{F}_u \cdot d\vec{S}_{u,\theta} \quad \text{[Equation 2]}$$

Herein, $S_{d,\theta}$ and $S_{u,\theta}$ are the path of the end tip due to an external force. Assuming that the tension applied by the surgical tool to the tissue during opposing traction is constant in the direction perpendicular to the end tip, $W_d$ and $W_u$ are calculated as dot products for simplicity.

Figure 7A:
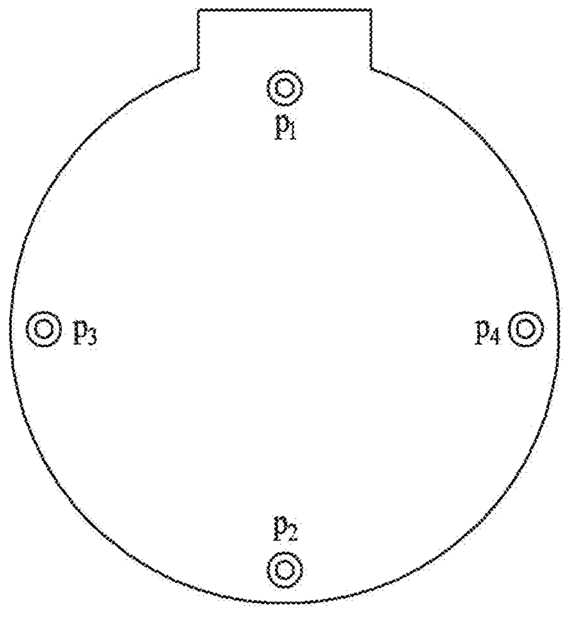
FIG. 7A is a diagram illustrating an arrangement of a main tendon.
Figure 7B:
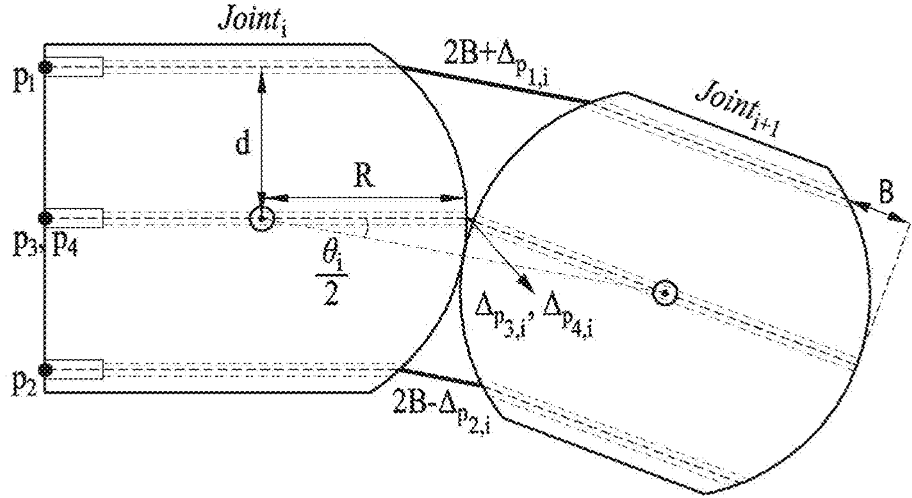
FIG. 7B is a diagram illustrating a change in the shape of the main tendon according to shape deformation of an overtube.

FIG. 7A and FIG. 7B show the arrangement of major tendons and tendon elongation caused by the relative angle θi between Joint and $\text{Joint}_{i+1}$. If the overtube is composed of n rolling joints, the total elongation value of each tendon caused by the relative angle $\theta_i$ is as follows.

$$\Delta_{p1}=\sum_{i=1}^{n-1}\Delta_{p1,i}=\sum_{i=1}^{n-1}2(R-B)\left(1-\cos\left(\frac{\theta_i}{2}\right)\right)+2d\sin\left(\frac{\theta_i}{2}\right) \quad \text{[Equation 3]}$$

$$\Delta_{p2}=\sum_{i=1}^{n-1}\Delta_{p2,i}=\sum_{i=1}^{n-1}2(R-B)\left(1-\cos\left(\frac{\theta_i}{2}\right)\right)-2d\sin\left(\frac{\theta_i}{2}\right) \quad \text{[Equation 4]}$$

$$\Delta_{p3}=\Delta_{p4}=\sum_{i=1}^{n-1}\Delta_{p3,i}=\sum_{i=1}^{n-1}\Delta_{p4,i}=\sum_{i=1}^{n-1}2R\left(1-\cos\left(\frac{\theta_i}{2}\right)\right) \quad \text{[Equation 5]}$$

Herein, R is the radius of the rolling surface, B is the step depth of the tendon hole from the top of the sliding surface, and d is the distance between the tendon and the central axis. These parameters are determined by the desired geometrical properties. The elastic strain energy stored in each tendon may be summarized as follows.

$$U_{p_j}=\int_{\Delta_{p_{j,0}}}^{\Delta_{p_{j,0}}+\Delta_{p_j}} T(x)\cdot dx,\ (j=1,2,3,4) \quad \text{[Equation 6]}$$

A tendon tension model T is expressed as a function of tendon elongation, and may be obtained through a tensile test of each tendon. $\Delta_{pj,0}$ is the elongation of each tendon by the initial tension of the system, which may be calculated from the inverse function of T.

Figure 7C:
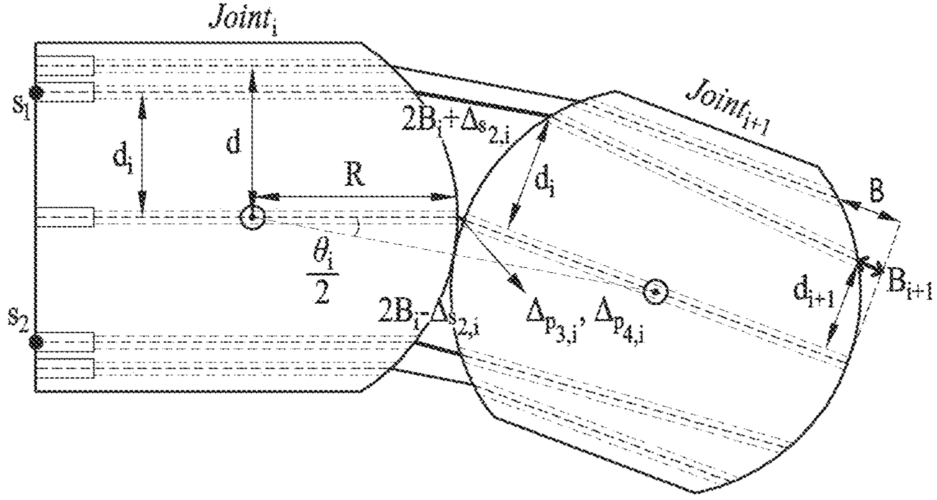
FIG. 7C is a diagram illustrating a change in the shape of an auxiliary tendon according to the shape deformation of the overtube.

FIG. 7C illustrates a case in which two auxiliary tendons $s_1$, $s_2$ are inserted in an arbitrary path to reinforce structural stiffness. Considering stability, $s_1$, $s_2$ are constrained along a central axis symmetry.

Similarly to Equation 3 and Equation 4, the total elongation values $s_1$ and $s_2$ caused by the relative angle $\theta_i$ are as follows.

$$B_i = R\left(1 - \cos\left(a\sin\left(\frac{d_i}{R}\right)\right)\right) \quad \text{[Equation 7]}$$

$$\triangle_{s_1} = \sum_{i=1}^{n-1} \triangle_{s_{1,i}} = \sum_{i=1}^{n-1} 2(R - B_i)\left(1 - \cos\left(\frac{\theta_i}{2}\right)\right) + 2d_i \sin\left(\frac{\theta_i}{2}\right) \quad \text{[Equation 8]}$$

$$\triangle_{s_2} = \sum_{i=1}^{n-1} \triangle_{s_{2,i}} = \sum_{i=1}^{n-1} 2(R - B_i)\left(1 - \cos\left(\frac{\theta_i}{2}\right)\right) - 2d_i \sin\left(\frac{\theta_i}{2}\right) \quad \text{[Equation 9]}$$

The elastic strain energy stored in the whole system is as follows. The elastic deformation energy includes $s_1$ and $s_2$.

$$U_{s_k} = \int_{\triangle_{s_{k,0}}}^{\triangle_{s_{k,0}} + \triangle_{s_k}} T(x) \cdot dx, \ (k = 1, 2) \quad \text{[Equation 10]}$$

$$U_{sum} = U_{p_1} + U_{p_2} + U_{p_3} + U_{p_4} + U_{s_1} + U_{s_2} \quad \text{[Equation 11]}$$

The total potential energy IId and IIu may be expressed as follows.

$$\Pi_d = U_{sum} - W_d \quad \text{[Equation 12]}$$

$$\Pi_u = U_{sum} - W_u \quad \text{[Equation 13]}$$

According to the minimum total potential energy principle, $O_{d,i}$ and $\theta_{u,i}$ that determine the position change of the end tip due to an external force may be obtained from the following equation.

$$\frac{\partial \Pi_d}{\partial \theta_i} = 0 \quad (i = 1, \ldots, n-1) \quad \text{[Equation 14]}$$

$$\frac{\partial \Pi_u}{\partial \theta_i} = 0 \quad (i = 1, \ldots, n-1) \quad \text{[Equation 15]}$$

The deflected positions $(x_{d,\theta}, y_{d,\theta})$ and $(x_{u,\theta}, y_{u,\theta})$ may be calculated using $\theta_{d,i}$ and $\theta_{u,i}$. Considering the purpose of optimization, the objective function $C(B_i, d_i)$ is defined as follows.

$$|\overrightarrow{S_{d,\theta}}| = \sqrt{(x_{d,\theta} - x_{0,\theta})^2 + (y_{d,\theta} - y_{0,\theta})^2} \quad \text{[Equation 16]}$$

$$|\overrightarrow{S_{u,\theta}}| = \sqrt{(x_{u,\theta} - x_{0,\theta})^2 + (y_{u,\theta} - y_{0,\theta})^2} \quad \text{[Equation 17]}$$

$$C(B_i, d_i) = \sum_{\theta=0}^{\theta_{max}} \left(|\overrightarrow{S_{d,\theta}}| + |\overrightarrow{S_{u,\theta}}|\right) \quad \text{[Equation 18]}$$

Herein, $\theta_{max}$ is the defined maximum bending angle of the overtube. The parameters that are changed in the modeled equations along the paths of $s_1$ and $s_2$ for structural stiffness reinforcement are $d_i$ and $B_i$. However, since $B_i$ depends on $d_i$, the paths of $s_1$ and $s_2$ are defined by optimizing $d_i$ in the direction of minimizing $C(d_i)$ as follows.

$$d_i = \text{argmin } C(B_i, d_i) \quad \text{[Equation 19]}$$

The effect of the stiffness-reinforced surgical device 1 according to an example embodiment was verified by the following experiment.

Figure 8A:
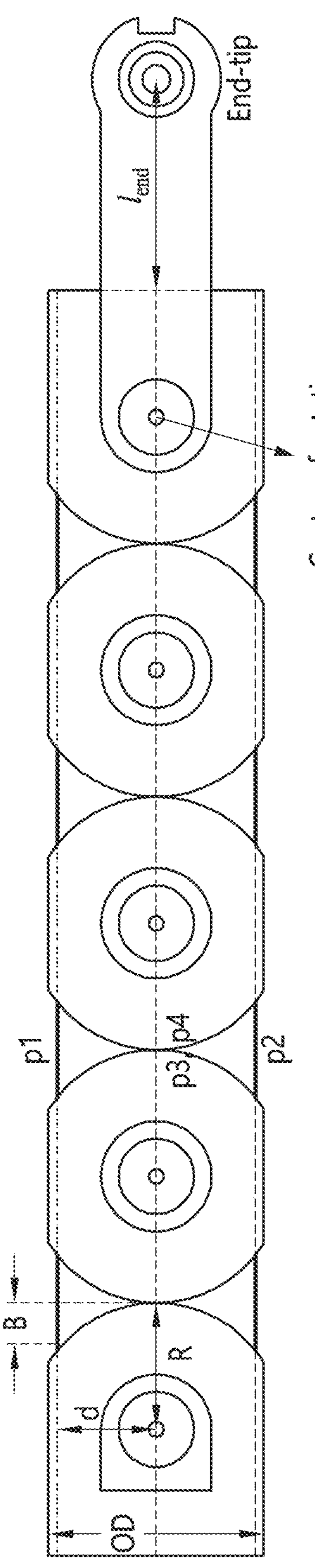
FIG. 8A is a diagram illustrating an overtube having a main tendon.

Two types of 1 DOF (single degree of freedom system) overtube were designed for the experiment. Referring to FIG. 8A, in the first type, only four main tendons were inserted for bending.

Figure 8B:
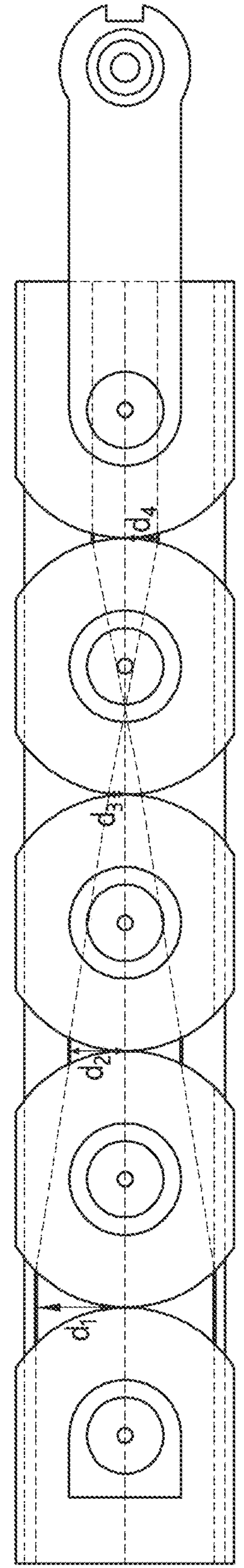
FIG. 8B and FIG. 8C are diagrams illustrating an overtube having a main tendon and an auxiliary tendon.

Referring to FIG. 8B, in the second type, two auxiliary tendons were additionally inserted along an optimized path in addition to the four main tendons used in FIG. 8A to reinforce structural stiffness. At this time, the error between the position change of the end tip due to an external force and the shape estimated from the equation was selected as an evaluation criterion.

The experimental environment is as follows. 6 DOF (six degrees of freedom system) optical tracking device (V120: OptiTrack) was used to measure the shape of the overtube. An optical marker was attached to the joint and the center of rotation of the end tip (see FIG. 9*a*). Both position change and error were calculated as Euclidean distances between marker points.

Overtube joint parameters such as OD=25 mm, R=15 mm, B=4.80 mm, d=11 mm, and $l_{end}$=25 mm for a minimum distance between optical markers measurable with the optical tracking device of 30 mm has been decided. The maximum and minimum values of $d_i$, which determine the paths of auxiliary tendons s1 and s2, were defined in consideration of the actual design issue.

Figure 8C:
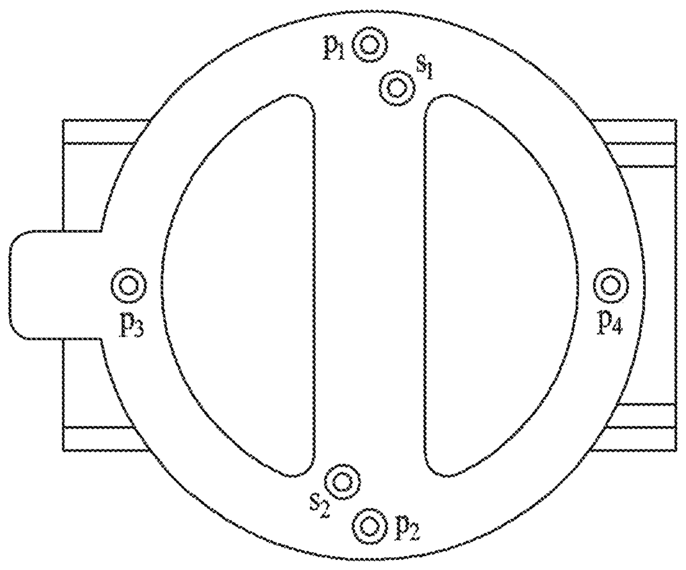

Optimization values obtained using the "fmincon" function in MATLAB Global Optimization Toolbox are [9, 6.35, 1.40, −3.81]. Referring to FIG. 8B, the optimized auxiliary tendon path for structural stiffness reinforcement was observed to be approximately 'S'. As shown in FIG. 8C, six tendons, i.e., four main tendons $p_1$, $p_2$, $p_3$, and $p_4$, and two auxiliary tendons, $s_1$ and $s_2$, were inserted from the proximal joint.

Figure 9A:
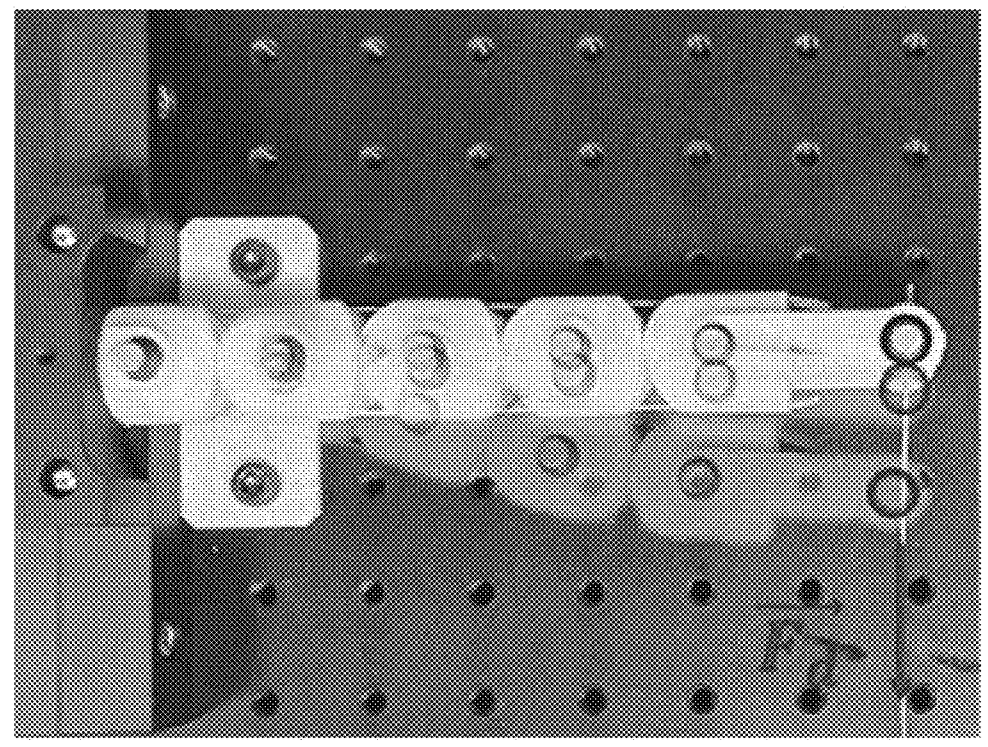
FIG. 9A is a diagram illustrating an experimental result when an initial angle of an end tip is 0°.
Figure 10A:
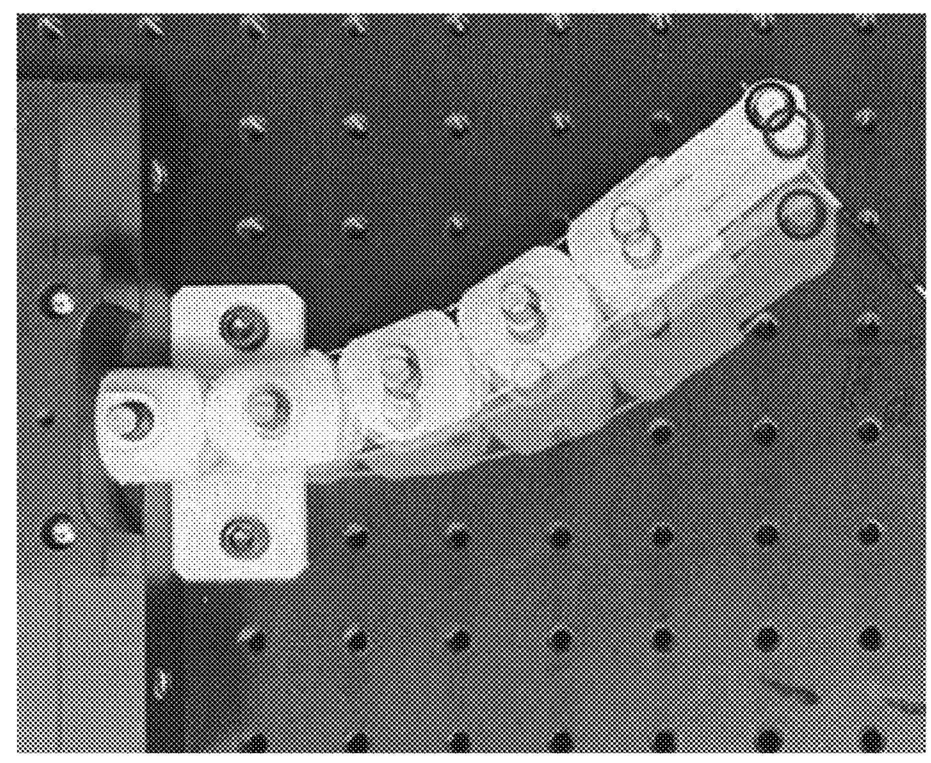
FIG. 10A and FIG. 11A are diagrams illustrating experimental results when the initial angle of the end tip is 45°.
Figure 11A:
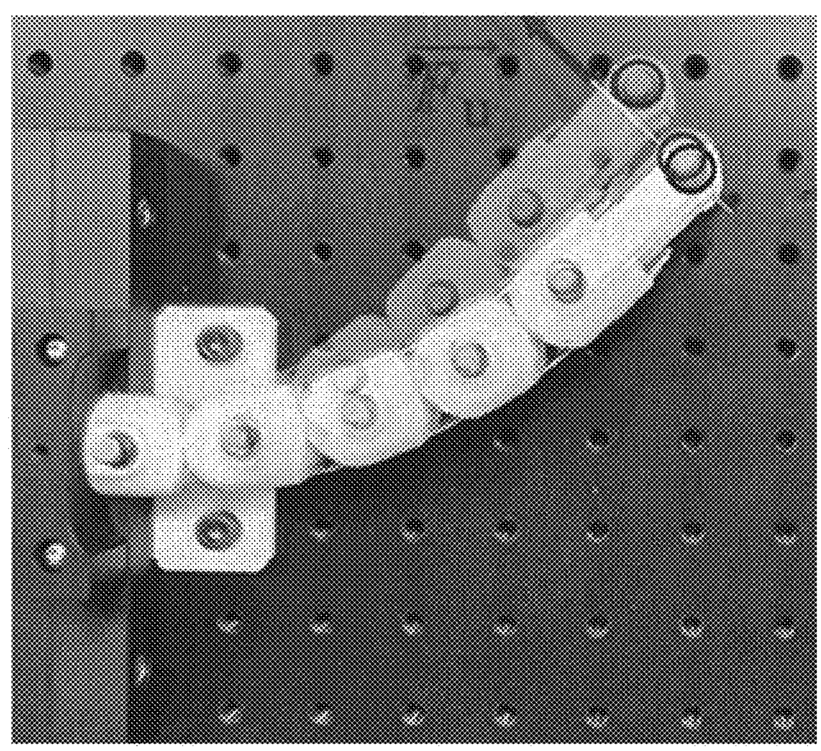

Experiments were performed with respect to the case where the initial angle of the overtube end tip was 0° (see FIG. 9*a*) and 45° (see FIG. 10*a* and FIG. 11*a*).

To eliminate the effect of gravity, an overtube was installed parallel to the ground, and external forces $F_d$ and $F_u$ were applied by connecting a weight of 500 g in a direction perpendicular to the end of the tendon. The initial tension of the six tendons of the overtube was set to 20N using a servo motor (Dynamixel XM-540-W270-R, ROBOTIS) and a load cell (333FDX, KTOYO).

Figure 9B:
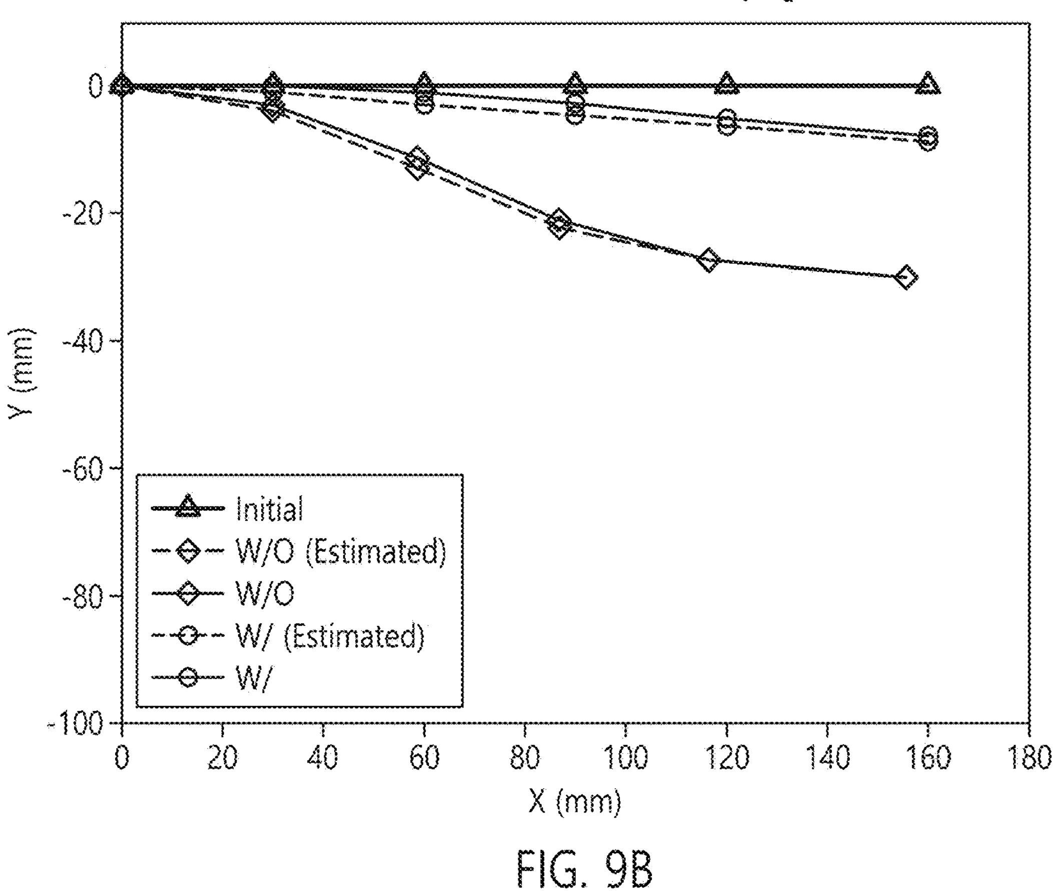
FIG. 9B is a graph illustrating the experimental result of FIG. 9A.

FIG. 9A is a view showing the experimental results when the initial angle of the end tip is 0°. FIG. 9B is a graph showing the experimental results of FIG. 9A.

Figure 10B:
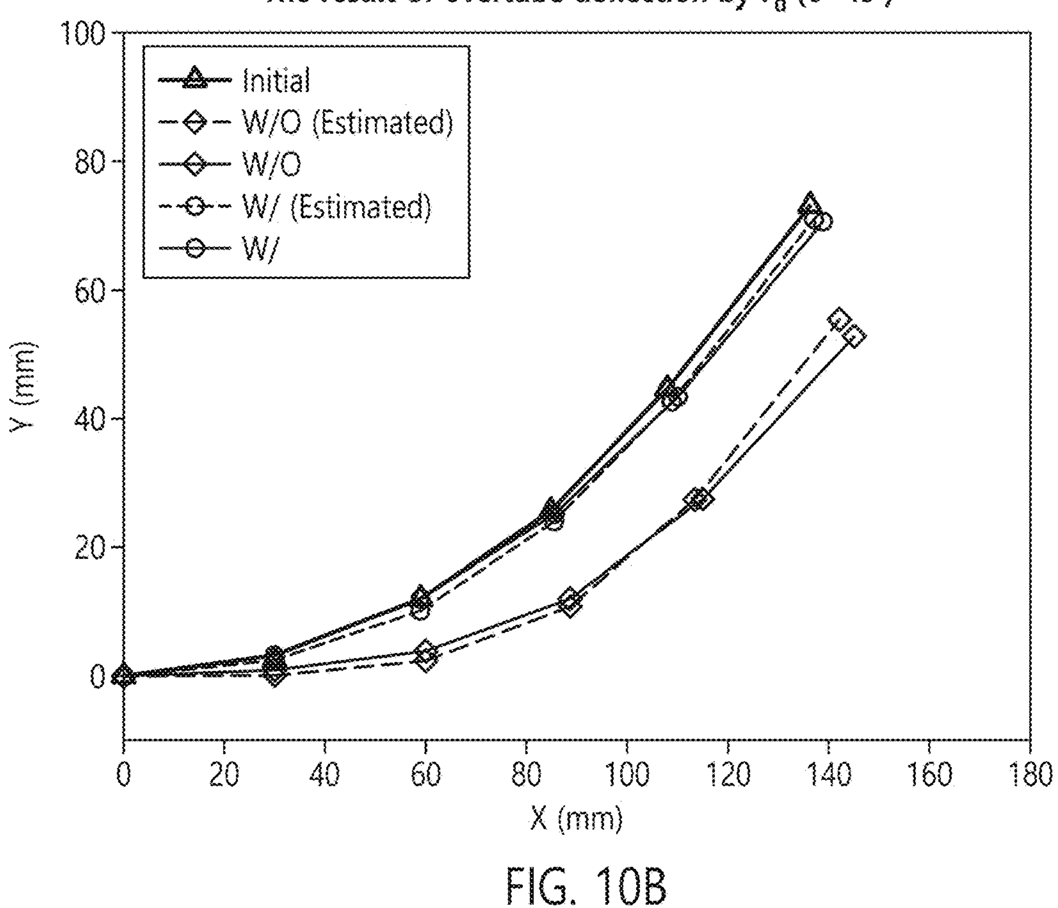
FIG. 10B is a graph illustrating the experimental result of FIG. 10A.
Figure 11B:
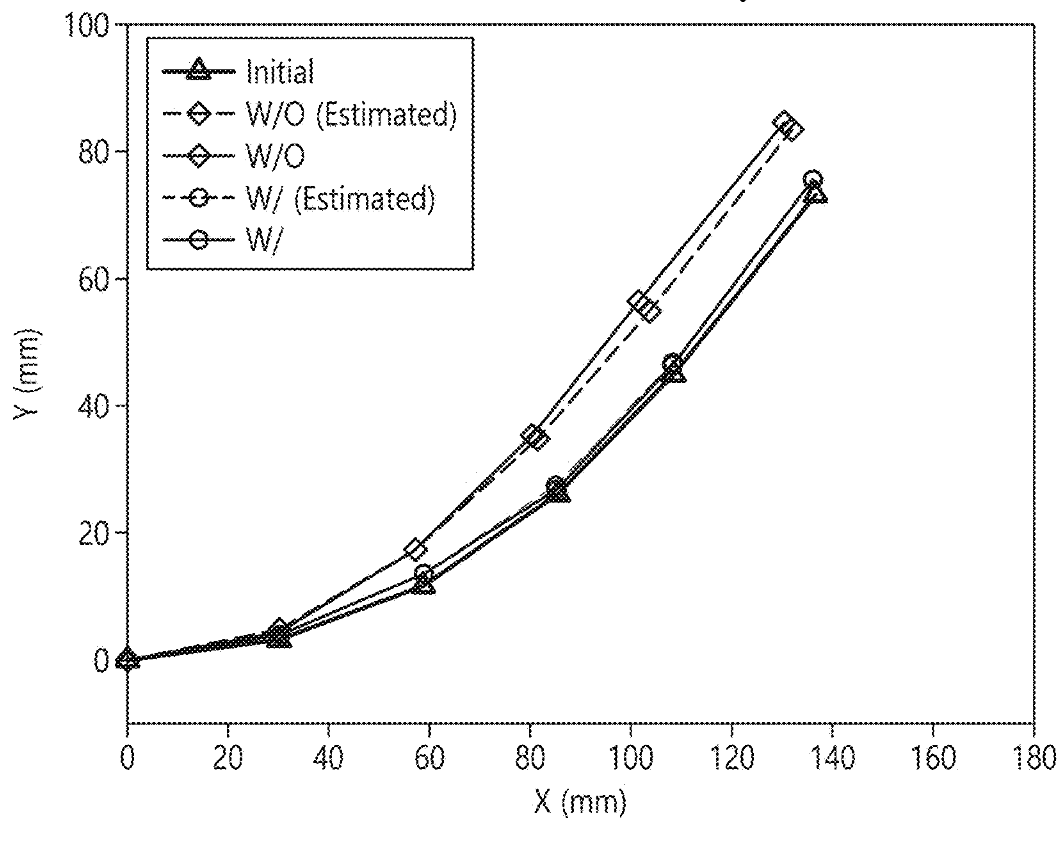
FIG. 11B is a graph illustrating the experimental result of FIG. 11A.

FIG. 10A and FIG. 11A are diagrams showing experimental results when the initial angle of the end tip is 45°. FIG. 10B is a graph showing the experimental results of FIG. 10A. FIG. 11B is a graph showing the experimental results of FIG. 11A.

The shape measured by the optical tracking device in FIG. 9B, FIG. 10B and FIG. 11B is indicated by a solid line, and the shape estimated from the equation is indicated by a dotted line.

In FIG. 9B, FIG. 10B, and FIG. 11B, the type having four main tendons is indicated by a blue line, and the type in which two auxiliary tendons are added to the route optimized for structural stiffness reinforcement is indicated by a red line. Considering that the external force applied to the initial angle 0° is symmetrical, the experiment was performed only on $F_d$. The experimental results are summarized in Table 1 below.

TABLE 1

| | External force $F_d$ | | External Force $F_u$ |
|---|---|---|---|
| Initial angle (°) | 0 | 45 | 45 |
| W/O auxiliary tendon (mm) | 30.42 | 22.10 | 12.98 |
| W/auxiliary tendon (mm) | 7.84 | 3.66 | 2.71 |

Referring to FIG. 9A and FIG. 9B, when the initial angle is 0°, the position change of the two types of overtube end tips due to $F_d$ was measured to be 30.42 mm and 7.84 mm.

Referring to FIG. 10A and FIG. 10B, when the initial angle is 45°, the position change due to $F_d$ was measured to be 22.10 mm and 3.66 mm.

Referring to FIG. 11A and FIG. 11B, when the initial angle is 45°, the position change due to Fu was measured to be 12.98 mm and 2.71 mm, respectively.

When the stiffness-reinforced surgical device 1 according to an example embodiment is used, the position change of the overtube end tip due to external force is reduced by 78.67% compared to when not in use. The average error between the measured value of the optical marker and the estimated position using the above equation was calculated to be 1.39 mm.

Figure 13:
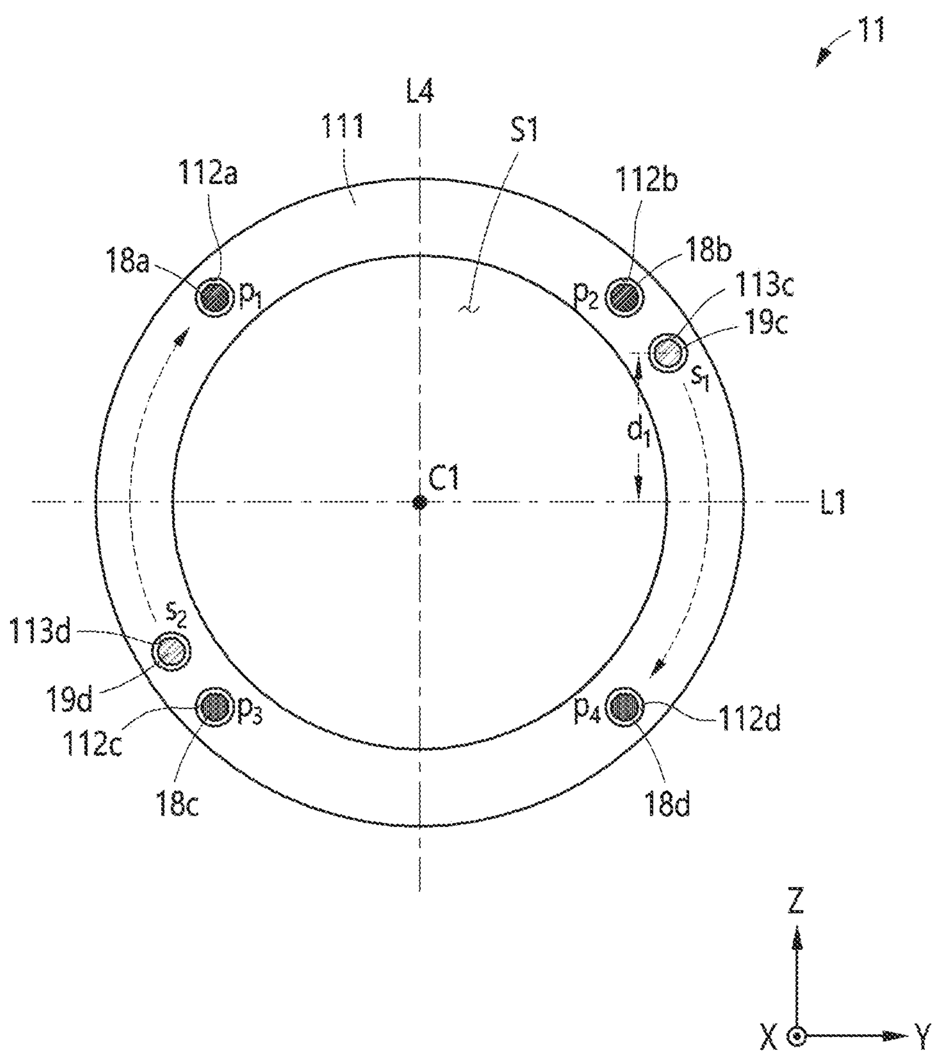
FIG. 13 is a diagram illustrating another example embodiment of the surgical device of FIG. 3.

FIG. 12 shows four main tendons 18 and two auxiliary tendons 19 installed in an overtube including a plurality of rolling joints, and in particular, the auxiliary tendons 19 is disposed along a 'S' shape, for example, 'S'-shaped step-step path. FIG. 13 shows the first auxiliary tendons 19*a*, 19*b* and the first auxiliary tendon holes 113*a*, 113*b* into which the first auxiliary tendons 19*a*, 19*b* are inserted.

The object of the present disclosure may be sufficiently achieved even by applying the auxiliary tendon and the auxiliary tendon hole of any one of FIG. 3 or FIG. 13.

For example, the auxiliary tendons shown in FIG. 3 are first auxiliary tendons 19*a*, 19*b*.

The first auxiliary tendon 19*a* is inserted into the first auxiliary tendon hole 113*a* located on the right side with respect to the central axis C1 of the first joint link 11, the second auxiliary tendon hole 123*a* formed in the second joint link 12 and the third joint link 13, and the third auxiliary tendon hole 133*a*.

The hole passing path of the first auxiliary tendon 19*a* is inclined downward in an approximately 'S' shape. From the first auxiliary tendon hole 113*a* of the first joint link 11 to the second auxiliary tendon hole 123*a* and the third auxiliary tendon hole 133*a*, the auxiliary tendon hole is formed from the upper side to the lower side.

In other words, the first auxiliary tendon hole 113*a* shown in FIG. 3 is formed on the upper right side of the joint link, and the second auxiliary tendon hole 123*a* and the third auxiliary tendon hole 133*a* shown in FIG. 4 and FIG. 5 are relatively gradually formed in the lower right side. Accordingly, while the formation direction of the auxiliary tendon hole is also formed from top to bottom, one or more of the neutral lines L1, L2, L3 of the first, second or third joint links 11, 12, 13 along the clockwise direction (refer to the arrow shown in FIG. 3) formed to cross.

On the other hand, the first auxiliary tendon 19*b* is inserted into the first auxiliary tendon hole 113*b* located on the left side with respect to the central axis C1 of the first joint link 11, the second auxiliary tendon hole 123*b* formed in the second joint link 12 and the joint link 13, and the third auxiliary tendon hole 133*b*.

The hole passing path of the first auxiliary tendon 19*b* is inclined upward in an approximately 'S' shape. From the first auxiliary tendon hole 113*b* of the first joint link 11 to the second auxiliary tendon hole 123*b* and the third auxiliary tendon hole 133*b*, the auxiliary tendon hole is formed from the lower side to the upper side.

In other words, the first auxiliary tendon hole 113*b* shown in FIG. 3 is formed on the lower left side of the joint link, and the second auxiliary tendon hole 123*b* and the third auxiliary tendon hole 133*b* shown in FIG. 4 and FIG. 5 are relatively gradually formed on the upper left side. Therefore, the formation direction of the auxiliary tendon hole is also formed from bottom to top and is formed to cross one or more of the respective neutral lines L1, L2, L3 of the first, second or third joint links 11, 12, 13 along the clockwise direction (refer to the arrow shown in FIG. 3).

On the other hand, the auxiliary tendons shown in FIG. 13 are first auxiliary tendons 19*c*, 19*d* as another example of the auxiliary tendons of FIG. 3.

The first auxiliary tendon 19*c* is inserted into the first auxiliary tendon hole 113*c* located on the right side with respect to the central axis C1 of the first joint link 11 and the third auxiliary tendon hole 133*c* formed in the third joint link 13 through the second joint link 12.

The hole passing path of the first auxiliary tendon 19*c* is inclined upward in an approximately 'S' shape. The auxiliary tendon hole is formed from the lower side to the upper side as it goes from the first auxiliary tendon hole 113*c* of the first joint link 11 to the third auxiliary tendon hole 133*c* of the third joint link 13.

In other words, the first auxiliary tendon hole 113*c* shown in FIG. 13 is formed on the lower right side of the joint link, and the third auxiliary tendon hole 133*c* is relatively gradually formed on the upper right side. Accordingly, the formation direction of the auxiliary tendon hole is also formed from bottom to top and is formed along the counterclockwise direction (refer to the arrow shown in FIG. 13).

On the other hand, the first auxiliary tendon 19*d* is inserted into the first auxiliary tendon hole 113*d* located on the left side with respect to the central axis C1 of the first joint link 11 and the third auxiliary tendon hole 133*d* formed in the third joint link 13 through the second joint link 12.

The hole passing path of the first auxiliary tendon 19*d* is inclined downward in an approximately 'S' shape. The auxiliary tendon hole is formed from the upper side to the lower side as it goes from the first auxiliary tendon hole 113*d* of the first joint link 11 to the third auxiliary tendon hole 133*d* of the third joint link 13.

In other words, the first auxiliary tendon hole 113*d* shown in FIG. 13 is formed in the upper left side of the joint link, and the third auxiliary tendon hole 133*d* is relatively gradually formed in the lower left side. Accordingly, the formation direction of the auxiliary tendon hole is also formed from bottom to top and is formed along the counterclockwise direction (refer to the arrow shown in FIG. 13).

Figure 14:
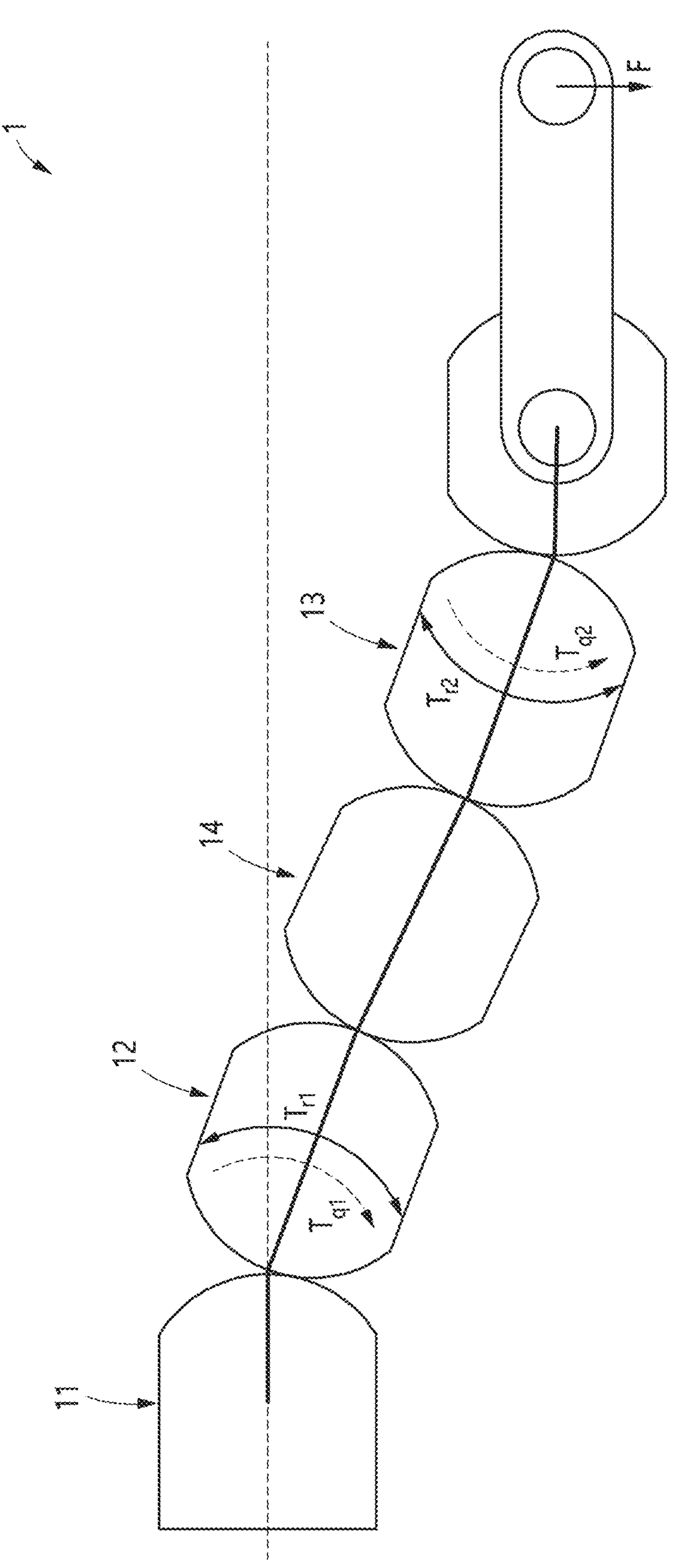
FIG. 14 is a diagram illustrating, when a rolling joint receives a load, rotation directions Tq1 and Tq2 of each joint and moment forces Tr1 and Tr2 to resist rotation of each joint.

As shown in FIG. 14, the rolling joint device 1 is an example, when a load F occurs on the end effector mounted on the end tip, the second joint link 12 according to the direction or angle in which the load occurs rotation or torque Tq1 is generated in a clockwise (or counterclockwise) direction, and the third joint link 13 is generated a rotation or torque Tq2 in a counterclockwise (or clockwise) opposite to the second joint link 12.

Accordingly, in the rolling joint device 1, when a load is applied to the end effector, deflection (refraction) occurs in different directions for each joint link by an external load. In order to prevent the deflection of the rolling joint link, the auxiliary tendon mechanism as described above may be used in example embodiments, but the auxiliary tendon mechanism may unintentionally cause torsion of the rolling joint.

Therefore, a roll-assisted tendon mechanism may be used to prevent such twisting. Hereinafter, a surgical device to which a rolling joint is applied according to an example embodiment will be described with reference to the accompanying drawings.

Figure 15:
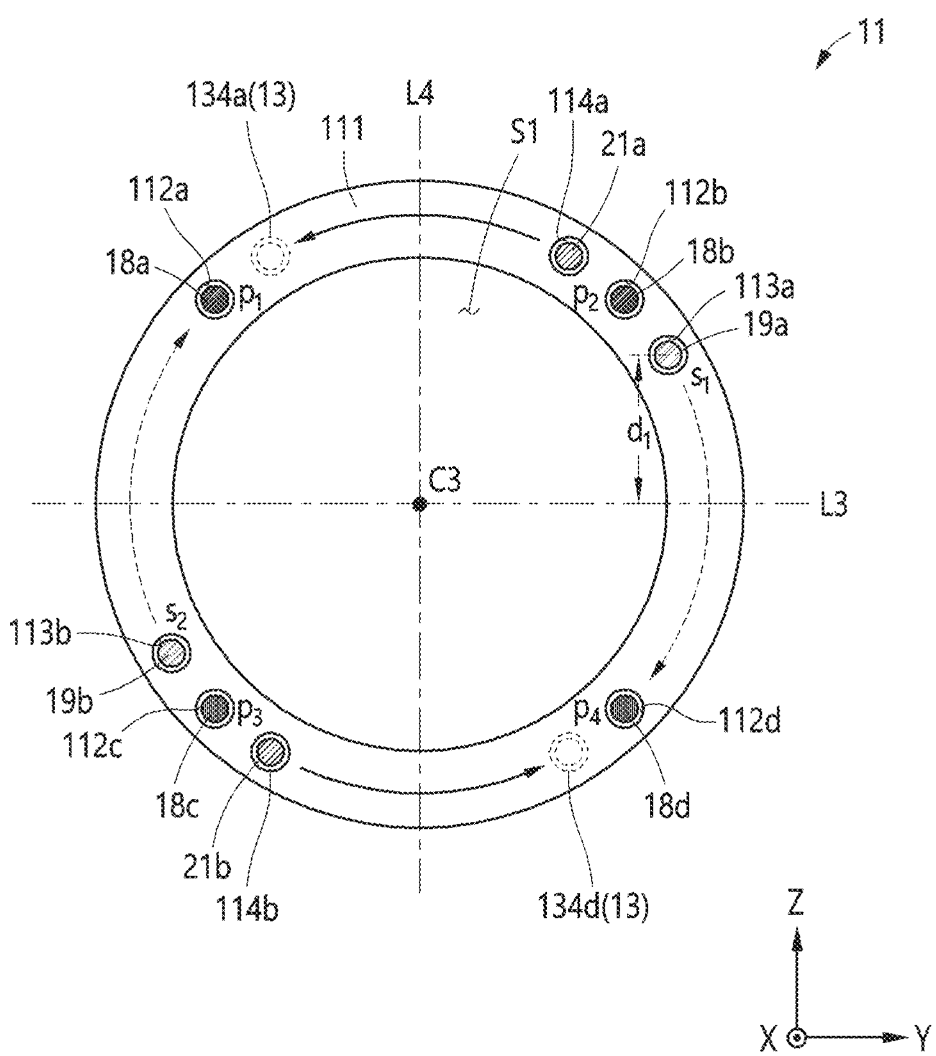
FIG. 15 is a diagram illustrating a second auxiliary tendon and a second auxiliary tendon hole.
Figure 16:
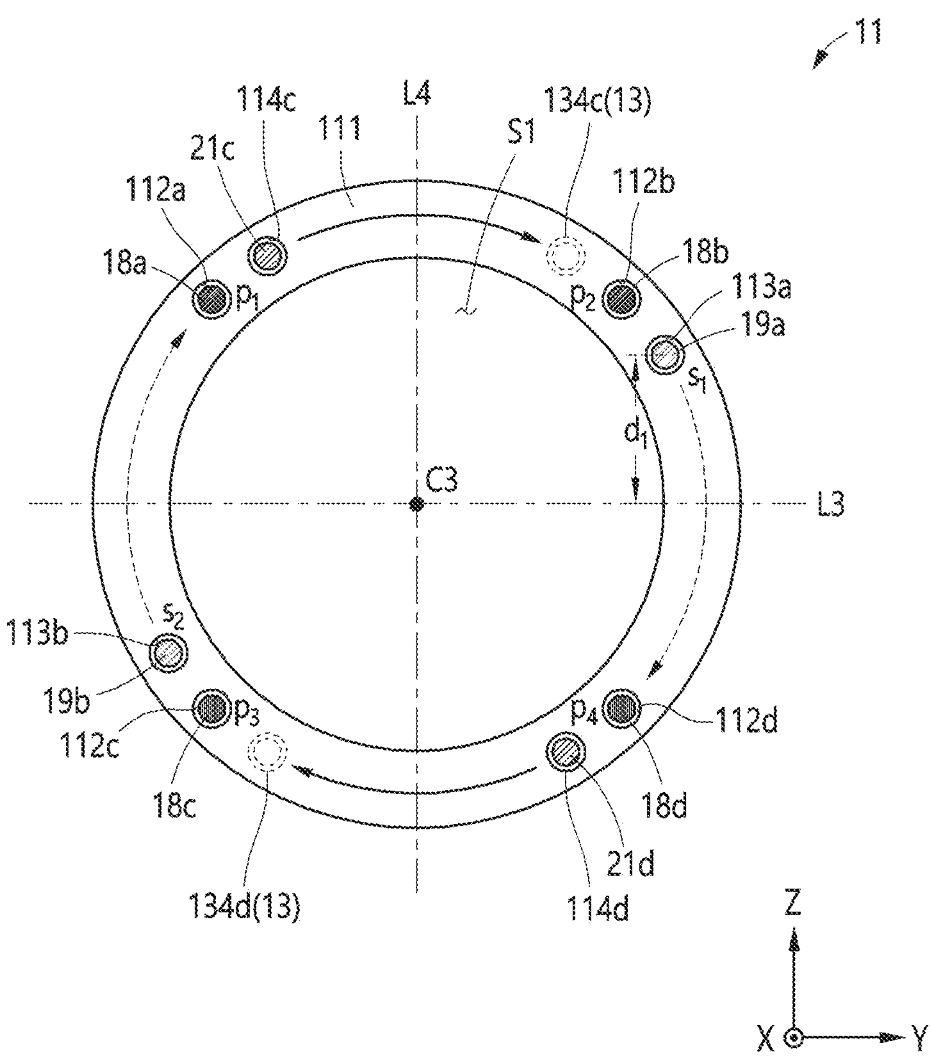
FIG. 16 is a diagram illustrating another example embodiment of the surgical device of FIG. 15.

It is possible to sufficiently achieve the object of the present disclosure by using any one of the first auxiliary tendons 21*a*, 21*b* shown in FIG. 15 and the second auxiliary tendons 21*c*, 21*d* shown in FIG. 16. The first auxiliary tendons 21*a*, 21*b* of FIG. 15 are to prevent torsion of the auxiliary tendons 19*a*, 19*b* of FIG. 3 when the mechanism acts, and the first auxiliary tendons 21*c*, 21*d* of FIG. 16 are to prevent torsion of the auxiliary tendons 19*c*, 19*d* of FIG. 13 when the mechanism acts.

The first auxiliary tendons 21*a*, 21*b* shown in FIG. 15 are inserted into respective auxiliary tendon holes provided in the first link 11, the second link 12, and the third link 13, as an example.

The first auxiliary tendon 21*a* is inserted into the upper auxiliary tendon holes 114*a*, 134*a*. The upper auxiliary tendon holes 114*a*, 134*a* are formed on the upper side of each joint link so that the passage path of the first auxiliary tendon 21*a* becomes the "S" shape in the first direction, for example, an oblique line ('/' as an example).

Therefore, the auxiliary tendon hole formed in each joint link is located in the upper right corner in the first joint link 11, and is gradually located in the upper left corner in the third joint link 13 along the counterclockwise direction.

Meanwhile, the first auxiliary tendon 21*b* is inserted into the auxiliary tendon holes 114*b*, 134*b* on the lower side. The lower auxiliary tendon holes 114*b*, 134*b* are formed on the lower side of each joint link so that the passage path of the first auxiliary tendon 21*b* becomes the "S" shape in the second direction, for example, an oblique line ('/' as an example).

Accordingly, the diagonal line in the first direction and the diagonal line in the second direction viewed from the y direction, that is, the diagonal line in the first direction and the diagonal line in the second direction on the side view viewed from the y direction, cross each other to form the "S" shape or an "X" shape. Accordingly, the auxiliary tendon hole formed in each joint link is located at the lower left side in the first joint link 11 and is gradually located at the lower right side in the third joint link 13 along a counterclockwise direction.

As an example, the second second auxiliary tendons 21*c*, 21*d* shown in FIG. 16 are inserted into the respective second auxiliary tendon holes provided in the first link 11, the second link 12, and the third link 13.

The second auxiliary tendon 21*c* is inserted into the auxiliary tendon holes 114*c*, 134*c* on the upper side. The upper auxiliary tendon holes 114*c*, 134*c* are formed on the upper side of each joint link so that the passage path of the second auxiliary tendon 21*c* is the "S" shape in the first direction, for example, an oblique line ('/' as an example).

Accordingly, the auxiliary tendon hole formed in each joint link is located in the upper left corner in the first joint link 11 and is gradually located in the upper right corner in the third joint link 13 along the clockwise direction.

Meanwhile, the second auxiliary tendon 21*d* is inserted into the auxiliary tendon holes 114*d* and 134*d* on the upper side. The upper auxiliary tendon holes 114*d*, 134*d* are formed on the lower side of each joint link so that the passage path of the second auxiliary tendon 21*d* is an oblique line in the second direction ('\' as an example).

Accordingly, the diagonal line in the first direction and the diagonal line in the second direction viewed from the y direction, that is, the diagonal line in the first direction and the diagonal line in the second direction on the side view viewed from the y direction, cross each other to form the "S" shape or an "X" shape. Accordingly, the auxiliary tendon hole formed in each joint link is located in the lower right corner in the first joint link 11 and is gradually located in the lower left corner in the third joint link 13 along the clockwise direction.

As described above, one set (or a pair), that is, a total of two auxiliary tendons are installed in the rolling joint device of FIG. 3 and FIG. 13. In contrast, in the rolling joint device of FIG. 15 and FIG. 16, two sets (or two pairs), that is, a total of four auxiliary tendons are installed.

Figure 17A:
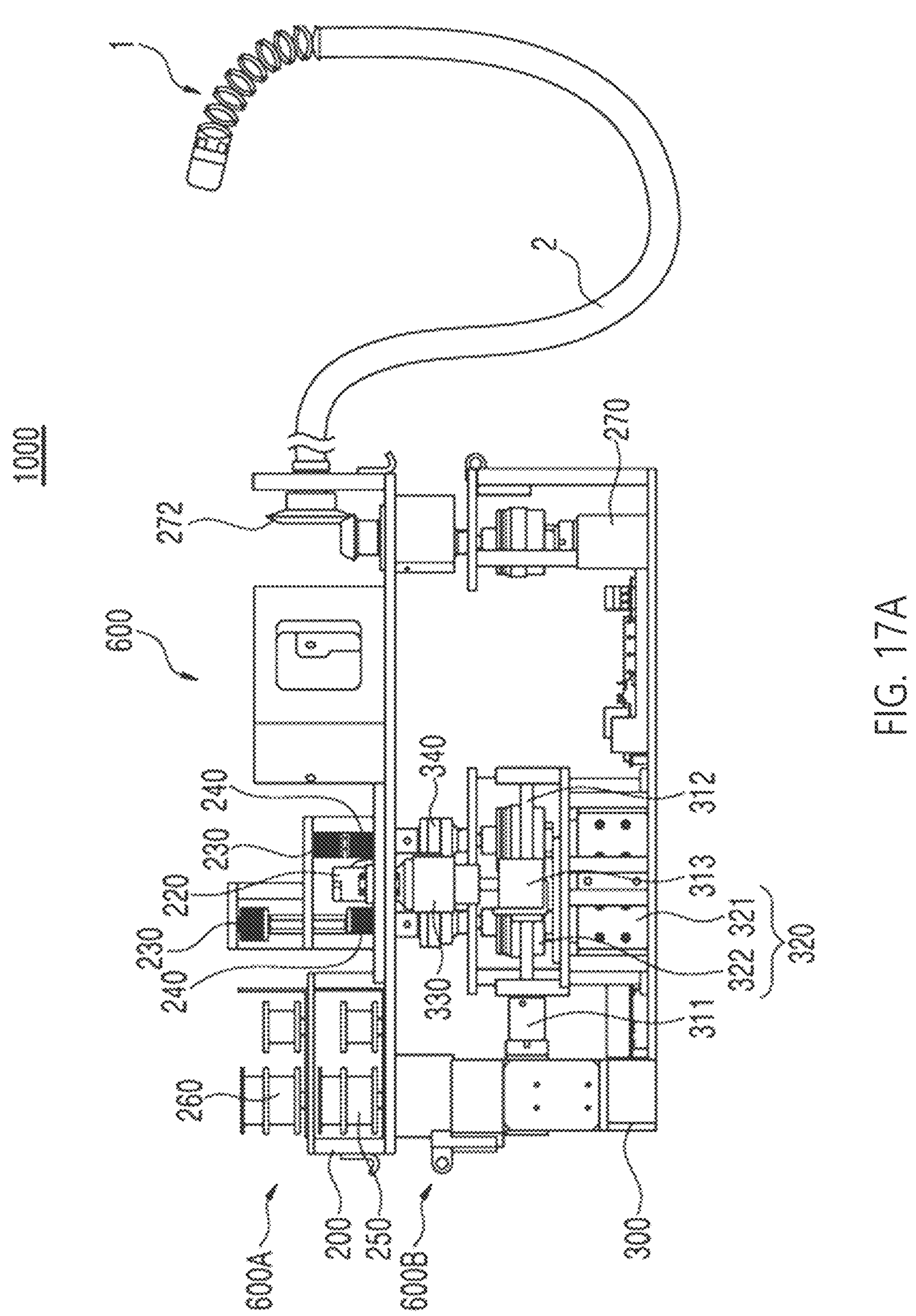
FIG. 17A is a side view illustrating a stiffness-reinforced surgical system according to an example embodiment.
Figure 17B:
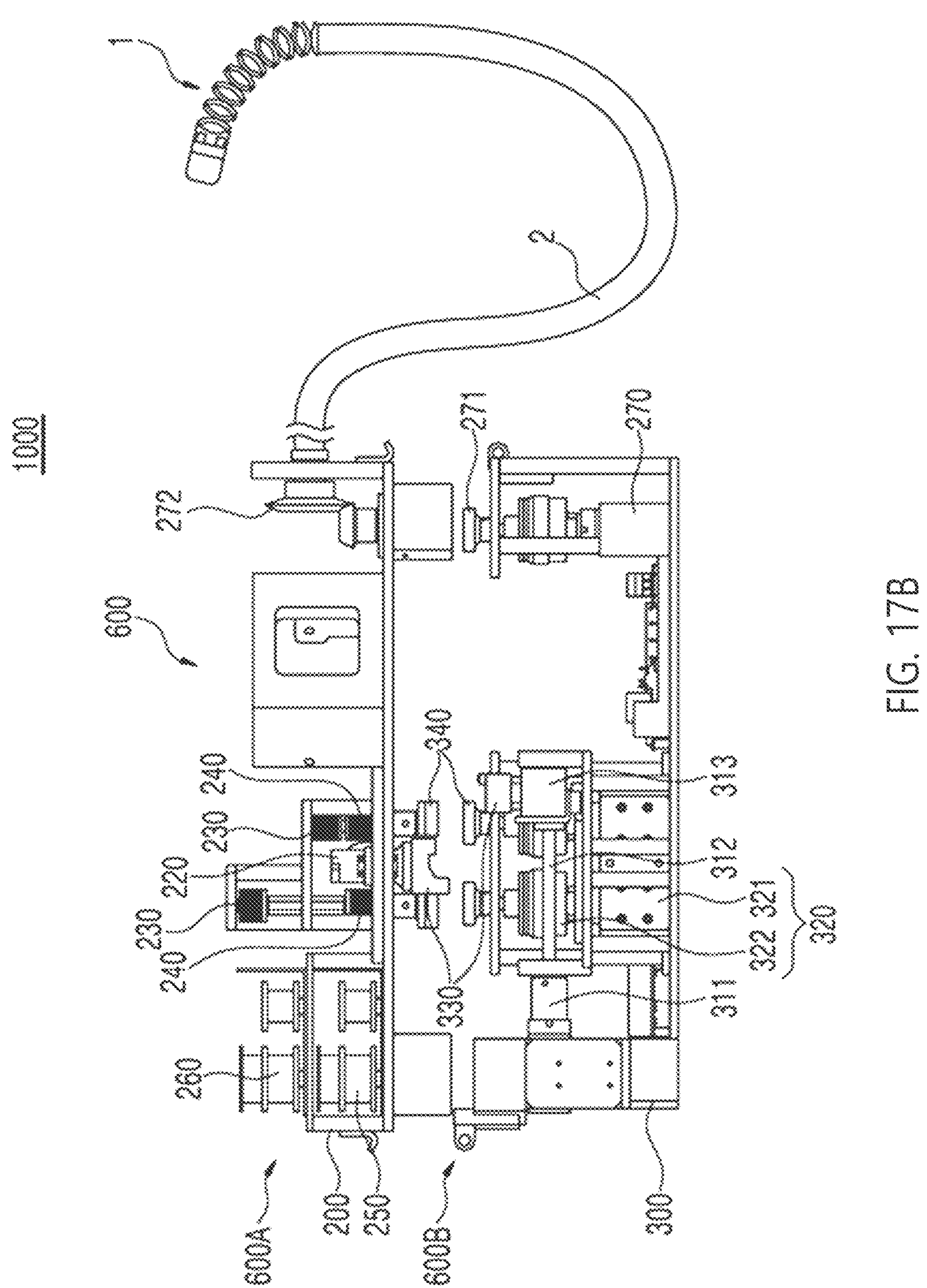
FIG. 17B is a side view illustrating a state in which a first body and a second body of a controller of FIG. 17A are separated.

FIG. 17A is a side view of a stiffness-reinforced surgical system 1000 according to an example embodiment. FIG. 17B is a side view illustrating a state in which the first body 200 and the second body 300 of the controller 600 of FIG. 17A are separated.

Figure 18A:
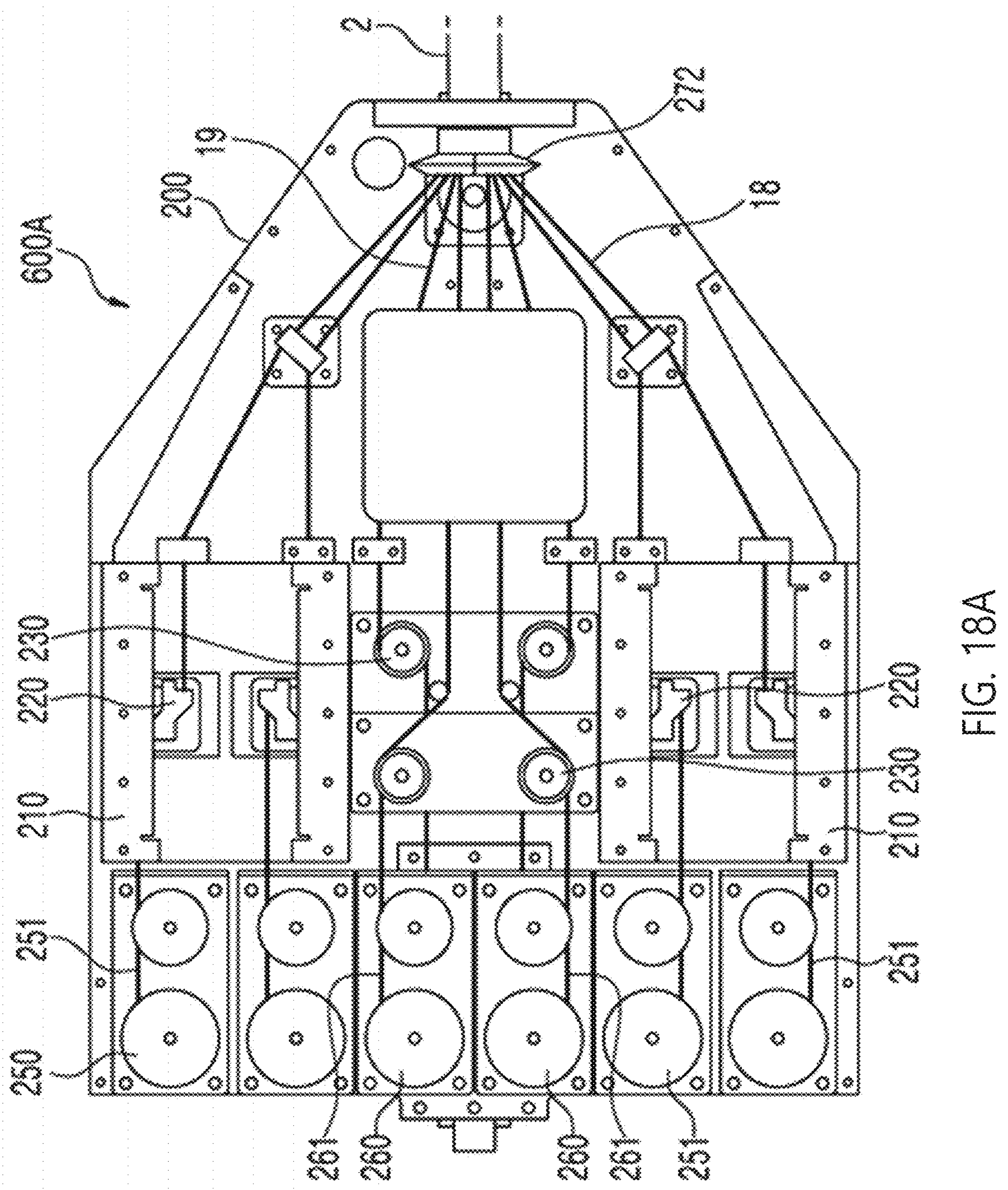
FIG. 18A is a plan view illustrating the first body of FIG. 17B.
Figure 18B:
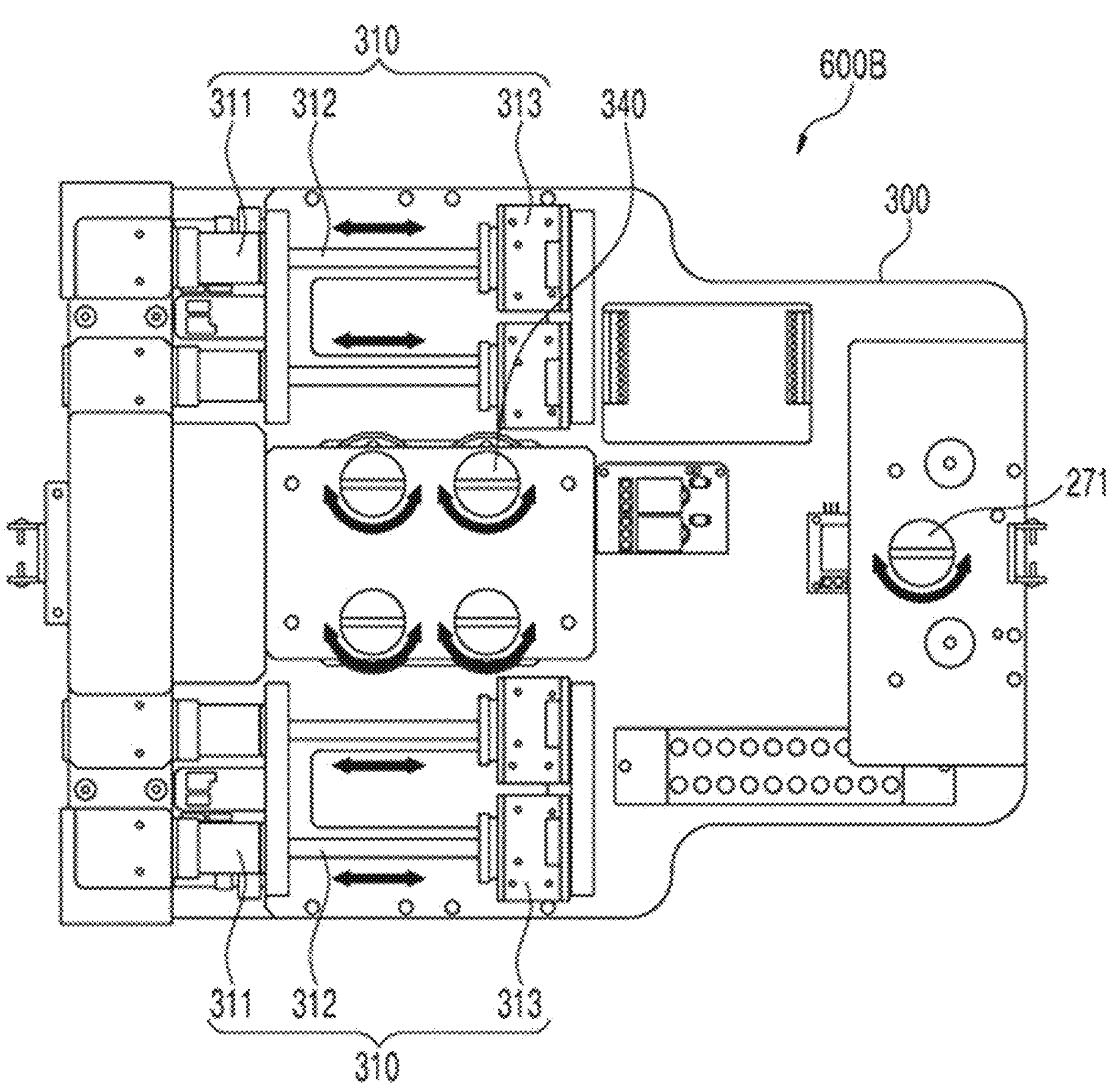
FIG. 18B is a plan view illustrating the second body of FIG. 17B.
Figure 19:
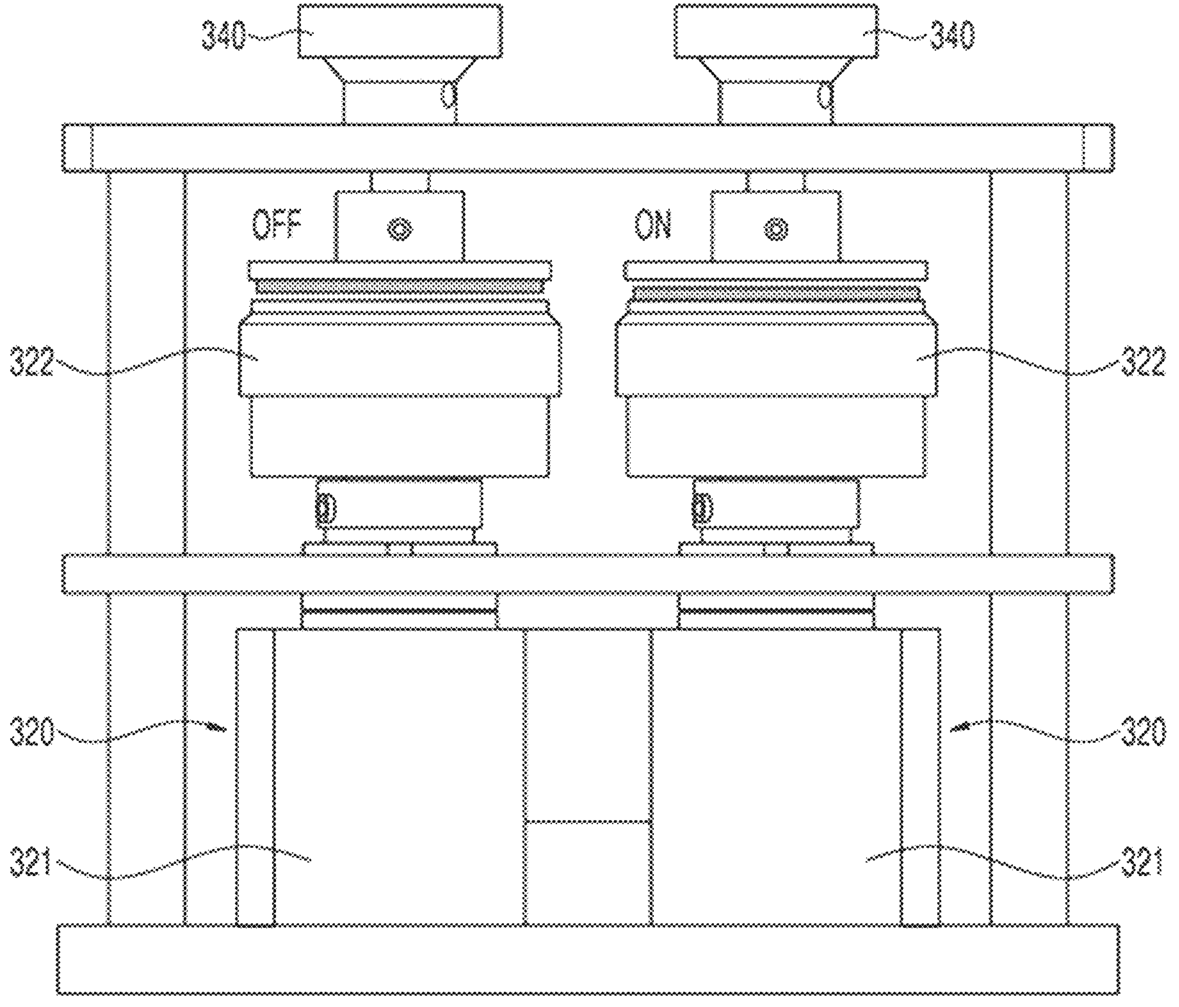
FIG. 19 is a diagram illustrating a second driver of FIG. 18.

FIG. 18A is a plan view illustrating the first body 200 of FIG. 17B. FIG. 18B is a plan view illustrating the second body 300 of FIG. 17B. FIG. 19 is a diagram illustrating the second driver 320 of FIG. 18.

As shown in FIG. 17A, the stiffness-reinforced surgical system 1000 according to an example embodiment includes a plurality of links, a main tendon 18, an auxiliary tendon 19 and a controller 600.

A plurality of links are provided rotatably with each other to form a joint device. The plurality of links means the above-described first link 11, second link 12, third link 13, and connection link 14.

The main tendon 18 and the auxiliary tendon 19 pass through the inside of the links. The main tendon 18 forms a traction force that drives the links, and the auxiliary tendon 19 forms a traction force that resists rotation of the links.

The controller 600 controls the traction force of the main tendon 18 and the auxiliary tendon 19. As shown in FIG. 17A and FIG. 17B, the controller 600 includes a first part 600A and a second part 600B.

The first part 600A includes a first body 200. The second part 600B includes a second body 300. The first body 200 and the second body 300 form a detachably coupled structure. The first body 200 and the second body 300 may be detachably coupled by a bolt or the like.

The first part 600A includes the first body 200, a rail 210, a slider 220, a first balance spring 250, a first wire 251, a first capstan 230, and a second capstan 240, a second balance spring 260, and a second wire 261.

The second part 600B includes the second body 300, a first driver 310, a second driver 320, a first coupler 330, and a second coupler 340.

The first body 200 and the second body 300 form a bracket or a housing shape. The overtube 2 is rotatably coupled to the front of the first body 200. For easy understanding of example embodiments, the right side is referred to as the front side of the controller 600 and the left side is referred to as the rear side of the controller 600 with reference to FIG. 17A and FIG. 18A.

A bevel gear 272 for transmitting a rotational force to the overtube 2 is formed in the first body 200. A motor 270 (hereinafter, 'first motor') for rotating the overtube 2 is provided in the second body 300. When the first body 200 and the second body 300 are coupled, the rotational force of the first motor 270 is transmitted to the bevel gear 272 through the coupler 271. By manipulation of a user input device (not shown), the first motor 270 may be rotated to rotate the overtube 2.

The rail 210 is fixed to the first body 200 and forms a long bar shape in the front and rear directions. The slider 220 is slidably mounted on the rail 210. The main tendon 18 is coupled to the slider 220.

Accordingly, when the slider 220 slides along the rail 210, the traction force of the main tendon 18 is adjusted. The rail 210 and the slider 220 are provided in the same number as the main tendon 18. FIG. 18A shows the overtube 2 having four main tendons 18.

The first driver 310 for moving the slider 220 along the rail 210 is provided on the second body 300. The first driver 310 is provided in the same number as the slider 220. The first driver 310 may be provided as a linear actuator. The linear actuator includes a motor 311 (hereinafter referred to as a 'second motor'), a screw 312, and a sliding member 313.

The screw 312 forms an elongated shape in the front-rear direction. The second motor 311 rotates the screw 312. When the screw 312 rotates, the sliding member 313 moves in the front-rear direction. When the first body 200 and the second body 300 are coupled, the slider 220 and the sliding member 313 are coupled by the first coupler 330.

Therefore, the first driver 310 may be moved the slider 220 along the rail 210. By operation of a user input device (not shown), the first driver 310 is operated to adjust the traction force of the main tendon 18.

The first balance spring 250 is provided at the rear of the first body 200. The first balance spring 250 is configured to form an initial (basic) tension of the main tendon 18. The first balance spring 250 is provided in the same number as the slider 220.

The first wire 251 connects the slider 220 and the first balance spring 250. The first balance spring 250 forms tension pulling the first wire 251 backward. As an example, when the main tendon 18 is stretched according to use, the extension of the main tendon 18 may be prevented to maintain a constant tension.

The shaft of the first capstan 230 is rotatably installed on the first body 200. The auxiliary tendon 19 is wound around the first capstan 230. Accordingly, when the first capstan 230 is rotated, the traction force of the auxiliary tendon 19 is adjusted. The first capstan 230 is provided in the same number as the auxiliary tendons 19. FIG. 18*a* shows an overtube 2 provided with four auxiliary tendons 19.

A second driver 320 for rotating the first capstan 230 is provided on the second body 300. FIG. 17A and FIG. 17B, when the first body 200 and the second body 300 are coupled, the axis of the first capstan 230 and the axis of the second driver 320 are connected to the second coupler 340. The second driver 320 is provided in the same number as the first capstan 230. The second driver 320 includes a motor 321 (hereinafter referred to as a 'third motor') and an electromagnetic clutch 322.

The electromagnetic clutch 322 selectively connects the shaft of the third motor 321 and the shaft of the second coupler 340. Therefore, when the first body 200 and the second body 300 are coupled, the electromagnetic clutch 322 selectively connects the shaft of the third motor 321 and the shaft of the first capstan 230.

When the shaft of the third motor 321 and the shaft of the first capstan 230 are connected, the third motor 321 rotates the first capstan 230. Therefore, by the manipulation of the user input device (not shown), the second driver 320 is operated to adjust the traction force of the auxiliary tendon 19.

The second capstan 240 is coupled to the same axis as the first capstan 230. The second wire 261 is wound around the second capstan 240. A second balance spring 260 is provided at the rear of the first body 200. The second balance spring 260 is configured to form the tension of the auxiliary tendon 19.

The second balance spring 260 is provided in the same number as the first capstan 230. The second balance spring 260 forms tension pulling the second wire 261 backward.

The second balance spring 260 forms the initial (basic) tension of the auxiliary tendon 19. As an example, when the main tendon 18 is stretched according to use, the extension of the main tendon 18 may be prevented to maintain a constant tension. In this case, the electromagnetic clutch 322 does not connect the shaft of the third motor 321 and the shaft of the first capstan 230.

In addition, the second balance spring 260 forms a constant tension when the overtube 2 is bent. In other words, it is possible to maintain a constant tension by preventing the auxiliary tendon 19 from being stretched or reduced when the main tendon 18 is pulled. In this case, the electromagnetic clutch 322 does not connect the shaft of the third motor 321 and the shaft of the first capstan 230.

Therefore, when the surgical device 1 reaches the position of the lesion by the traction of the main tendon 18, a preset traction force is added to the auxiliary tendon 19 so that the shape is fixed and the stiffness is increased at the same time, the position of the surgical robot to treat the lesion without change. At this time, the electromagnetic clutch 322 connects the shaft of the third motor 321 and the shaft of the first capstan 230 so that a preset traction force is added to the auxiliary tendon 19.

Figure 20:
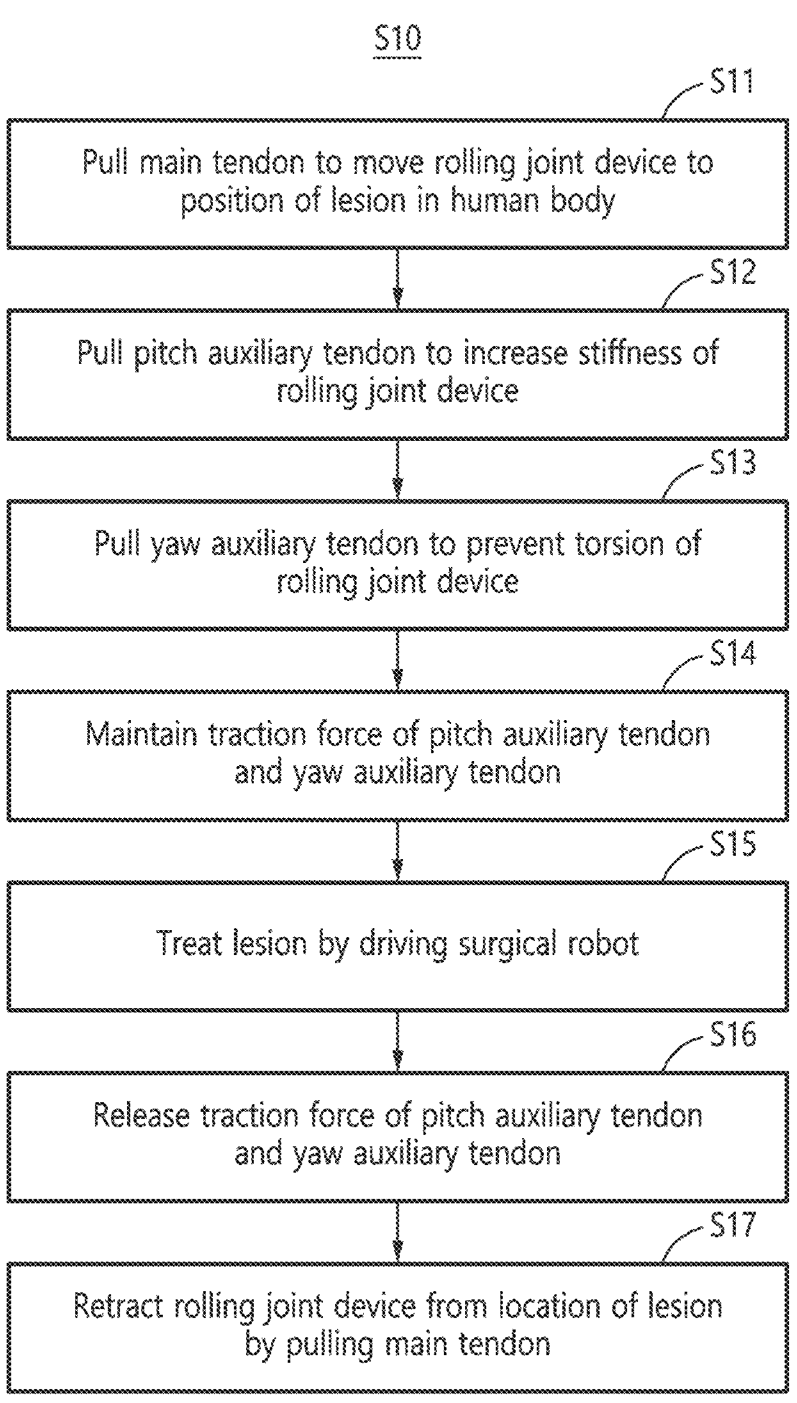
FIG. 20 is a diagram illustrating a control method of a stiffness-reinforced surgical system.
Figure 21:
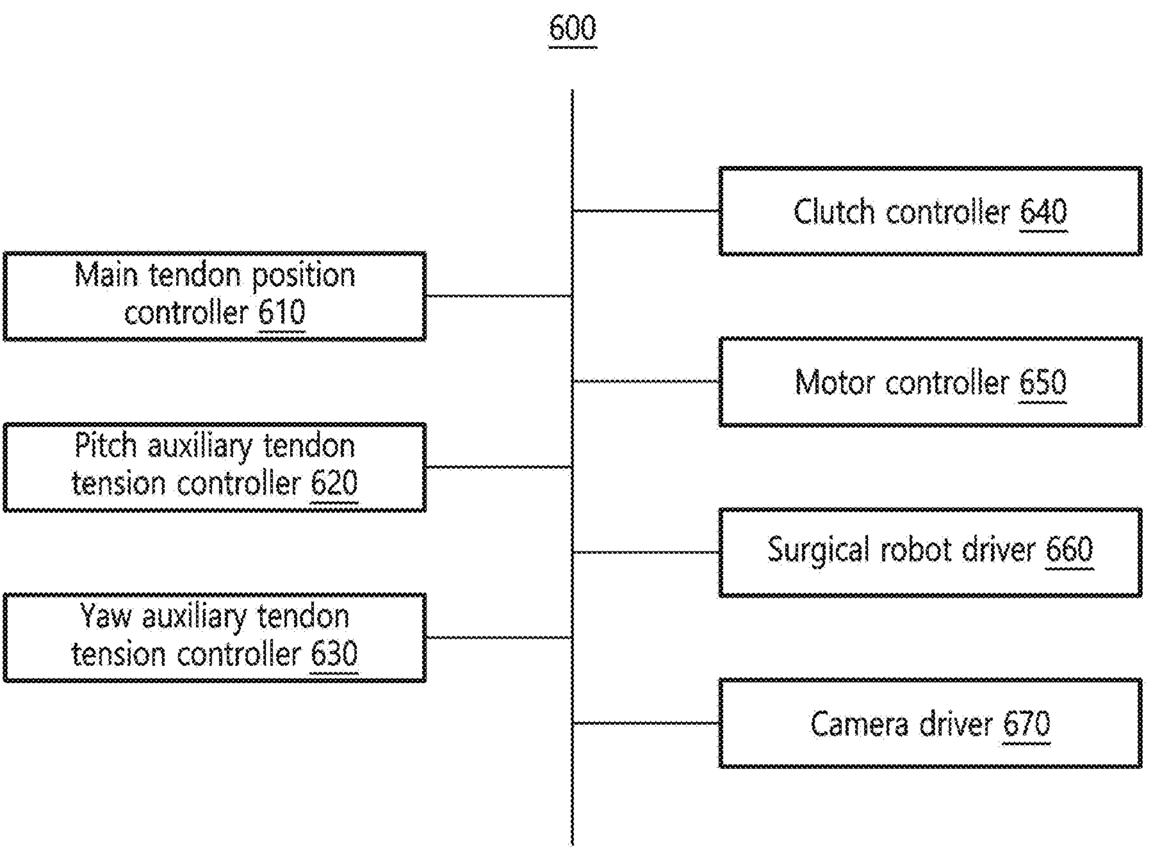
FIG. 21 is a diagram schematically illustrating various controllers and drivers of the controller.

FIG. 20 is a view showing a control method S10 of the stiffness-reinforced surgical system 1000. FIG. 21 is a diagram schematically illustrating various controllers and drivers of the controller 600.

Hereinafter, the control method S10 of the stiffness-reinforced surgical system 1000 according to an example embodiment will be described in detail.

Referring to the accompanying drawings, according to the traction of the main tendon 18, the rolling joint device 1 (surgical device) is moved to the lesion in the human body, so that the rolling joint device 1 may reach the lesion. Therefore, the main tendon position controller 610 controls the position of the main tendon 18, and according to the position control of the main tendon 18, the rolling joint device 1 moves to the lesion in the human body (S11).

Meanwhile, in example embodiments, both the main tendon 18 and the auxiliary tendon 19 are wires, and the main tendon 19 may be a main wire, and the auxiliary tendon 19 may be an auxiliary wire. Each main wire and auxiliary wire are both towed according to the wire pulling mechanism.

At this time, the main tendon 18 is towed to move the rolling joint device 1, so that the position and direction of the rolling joint device 1 is controlled, and the auxiliary tendon 19 is towed to prevent the stiffness increase or torsion of the rolling joint device 1.

Next, the auxiliary tendon 19 is used in example embodiments because the traction force of the main tendon 18 alone is insufficient in stiffness.

First, auxiliary tendons 19*a*, 19*b*, 19*c*, 19*d* are used. In other words, when the rolling joint device 1 reaches the lesion, the rolling joint device needs to maintain a 'cobra shape' shape as an example according to the location of the lesion.

At this time, the rolling joint device 1 cannot maintain the 'cobra shape' only by the traction force of the main tendon 18. Therefore, in example embodiments, by driving the auxiliary tendons 19*a*, 19*b*, 19*c*, 19*d*, the rolling joint device 1 may be maintained in a 'cobra shape'.

Accordingly, the auxiliary tendons 19*a*, 19*b*, 19*c*, 19*d* are pulled under the control of the auxiliary tendon tension controller 620, thereby increasing the stiffness to prevent deflection of the rolling joint device 1 (S12). When the stiffness of the rolling joint device 1 is increased, the 'cobra shape' may be maintained, and on the other hand, the shape locking of the rolling joint device 1 may be possible.

On the other hand, when the auxiliary tendons 19*a*, 19*b*, 19*c*, 19*d* are towed under the control of the auxiliary tendon tension controller 620, torsion occurs in the joint link of the rolling joint device 1. Therefore, the auxiliary tendon is pulled under the control of the auxiliary tendon tension controller 630 to prevent torsion of the rolling joint device 1, thereby preventing the twisting of the rolling joint device 1 (S13).

By driving the clutch controller 640 before or at the same time as driving the auxiliary tendon tension controller 620 and the auxiliary tendon tension controller 630 so that the electronic clutch unit is 'ON', the rotational driving force of the motor unit 520 is to be delivered to the corresponding capstan.

Next, after the torsion is prevented while the stiffness of the rolling joint device 1 is increased according to the traction of the auxiliary tendons 19*a*, 19*b*, 19*c*, 19*d* and the auxiliary tendons 21*a*, 21*b*, 21*c*, 21*d*, an operation of maintaining the traction force of the auxiliary tendons 19*a*, 19*b*, 19*c*, 19*d* and the auxiliary tendons 21*a*, 21*b*, 21*c*, 21*d* is performed according to the control of the controller 620 and the auxiliary tendon tension controller 630 (S14).

Even if a load is applied to the end effector according to the maintenance of the traction force of the auxiliary tendon, deflection of the rolling joint device 1 may be prevented, and further, the position of the end effector may not be changed. Furthermore, according to the maintenance of the traction force of the auxiliary tendons 21*a*, 21*b*, 21*c*, 21*d*, it is possible to simultaneously prevent the torsion of the rolling joint device 1.

If torsion is prevented while stiffness is maintained in the rolling joint device 1, then operation of removing or treating a lesion is performed by driving surgical robot disposed in the lumen of the rolling joint under the control of the surgical robot driver 660 (S15).

A lumen may be formed on the inside of the rolling joint device 1. As an example, an endoscope camera may be disposed in the first lumen, and a surgical robot (eg, Grasper) capable of removing or treating a lesion may be disposed in the second lumen.

The surgical robot is driven by the surgical robot driver 660, and the endoscope camera is driven by the camera driver 670. In FIG. 17A, the controller 600 mainly represents the surgical robot driver 660.

Next, after the treatment of the lesion, operation of releasing the traction force of the auxiliary tendons 19*a*, 19*b*, 19*c*, 19*d* and the auxiliary tendons 21*a*, 21*b*, 21*c*, and 21*d* under the control of the auxiliary tendon tension controller 620 and the auxiliary tendon tension controller 630 is performed (S16). After releasing the traction force of the auxiliary tendons 21*a*, 21*b*, 21*c*, and 21*d*, the traction force of the auxiliary tendons 19*a*, 19*b*, 19*c*, and 19*d* may be released.

When the traction force of the auxiliary tendons 19*a*, 19*b*, 19*c*, 19*d* and the auxiliary tendons 21*a*, 21*b*, 21*c*, 21*d* is released, the stiffness of the rolling joint device 1 is restored to its original state, and accordingly, the main tendon position controller 610, as the main tendon 18 is pulled according to the position control, the rolling joint device 1 retreats from the location of the lesion and exits to the outside of the human body (S17).

According to example embodiments, by controlling the traction forces of the main and auxiliary tendons by the the controller, it is possible to provide a stiffness-reinforced surgical system configured such that the overtube forms sufficient flexibility while being inserted into the lumen and forms high stiffness during lesion removal.

In addition, by including pulling the main tendon to move the joint device to the lesion in the body, and pulling the auxiliary tendon to increase the stiffness of the joint device, it is possible to provide a method for controlling a stiffness-reinforced surgical system in which the overtube forms sufficient flexibility while being inserted into the lumen, and the overtube forms high stiffness when the lesion is remove.

As long as the overtube has sufficient flexibility and high stiffness to minimize pitch rotation, yaw rotation, or roll rotation of at least a portion of the overtube or tip, the above-described surgical device or rolling joint device, various links of the device, overtube, main tendon, main tendon hole, auxiliary tendon, auxiliary tendon hole, etc. may be modified or improved as in various embodiments described below.

The first embodiment of the modification or improvement relates to a rolling joint device in which a pair of auxiliary tendons are installed, and to various structures and methods of auxiliary tendon holes of the device.

Figure 22:
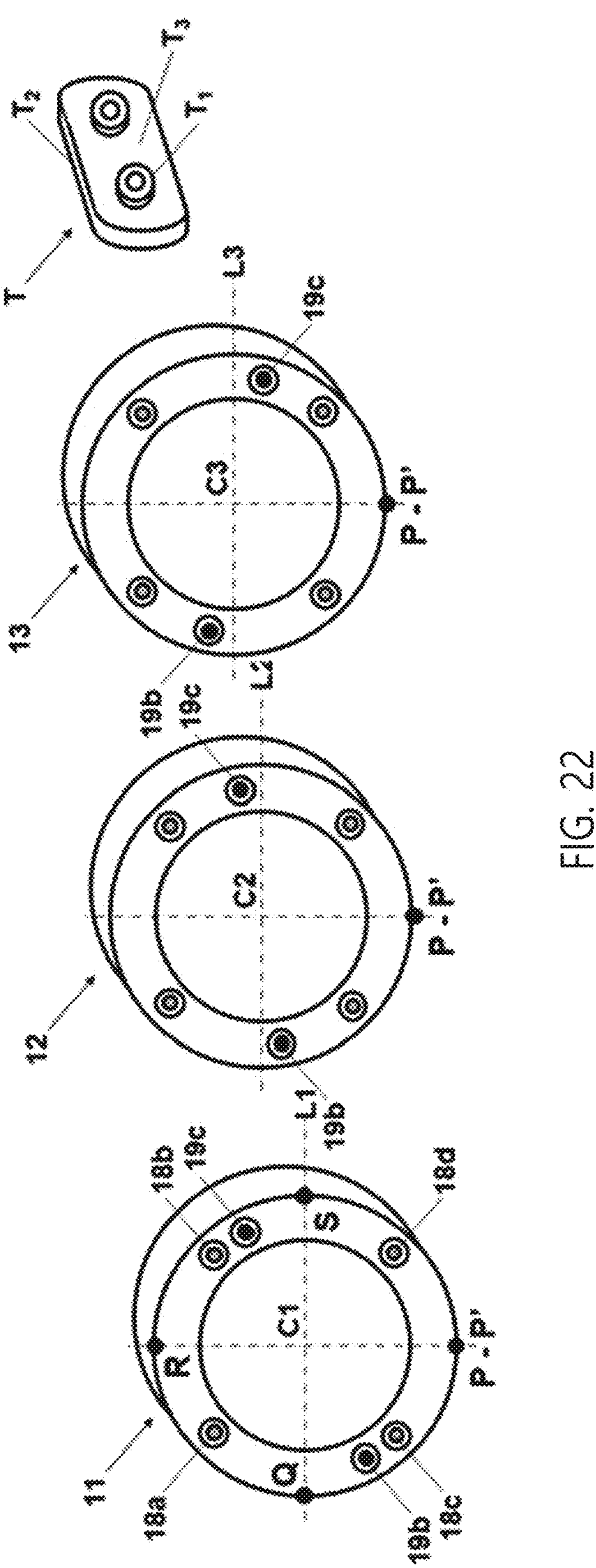
FIG. 22 is a schematic diagram illustrating a rolling joint device including a total of six links and two main tendons.

FIG. 22 is similar to FIG. 3, but the rolling joint device of FIG. 22 has a total of six links (that is, the first link 11, the second link 12, the third link 13, the fourth link 14, a fifth link 15 and a sixth link) and a tip T, the device having two sets (four in total) of main tendons 18*a*, 18*b*, 18*c*, 18*d* along the links 11, 12, 13, 14, 15, 16 and a set (two in total) of auxiliary tendons 19*b*, 19*c* are installed.

However, for convenience of explanation, only the first to third links 11, 12, and 13 and the tip T are shown in FIG. 22. In addition, one or more additional links (eg, seventh link, eighth link, ninth link), one or more connecting links, etc. may be additionally installed between the sixth link 16 and the tip T.

In the first link 11 of FIG. 22, the auxiliary tendon 19*b* is installed inside the hole at the lower left side of the cross-section of the first link 11, while the auxiliary tendon 19*c* is installed inside the hole at the upper right side of the cross-section. In addition, the auxiliary tendon 19*b* is located below the neutral line L1 of the first link 11, and the auxiliary tendon 19*c* is located above the neutral line L1.

In the case of the second link 12, the auxiliary tendon 19*b* is installed in the lower left side of the cross section of the second link 12 and inside a hole located just below the neutral line L2. On the other hand, the auxiliary tendon 19*c* is installed in the upper right side of the cross section and inside the hole located just above the neutral line L1.

In the case of the third link 13, the auxiliary tendon 19*b* is installed in the upper left side of the cross section of the third link 13 and inside the hole located just above the neutral line L3. On the other hand, the auxiliary tendon 19*c* is installed in the lower right side of the cross section and inside the hole located just below the neutral line L3.

The auxiliary tendon 19*c* may be installed in various parts of one surface (eg, the surface shown in FIG. 22) of the tip, for example, T1, T2, T3, and the like. On the other hand, the auxiliary tendon 19*b* may be installed at various positions on the opposite side of the tip (for example, the side not visible in FIG. 22).

FIG. 23 is a virtual development view obtained by cutting an virtual outer surface of a device along P-P' in FIG. 22 or P-P' in the left panel of FIG. 23, in which a rolling joint device manufactured by combining the same six links as the link of FIG. 22 in a line, and combining the tip (T) with the sixth link 16, which is the last link.

However, in the case of the device of FIG. 23, since the diameter of each link 11-16 is larger than the height of the tip T, the outer surface of the tip is divided into two and displayed separately.

The auxiliary tendon 19_b_ is installed in the "S" shape in the direction from the first link 11 to the tip T on the virtual outer surface of the device of FIG. 22, whereas the auxiliary tendon 19_c_ is the virtual It is installed in the "S" shape on the lower part of the outer surface. Therefore, when the virtual development view of FIG. 23 is folded along a straight line passing through R, a set of auxiliary tendons 19_b_ and 19_c_ may be regarded as intersecting in an "X" shape as in the example of FIG. 12.

In particular, the "S" shape of the plurality of links 11~16 and the auxiliary tendons 19_b_ and 19_c_ installed on the tips is greater than 90° as in the cross-section of the first link 11 shown on the left side of FIG. 23 but 180° corresponds to the smaller angles $A_b$ and $A_C$. Hereinafter, the angles $A_b$ and $A_C$ will be referred to as "S"-shaped angles.

The "S" angle $A_b$ affecting the "S" shape of the auxiliary tendon 19_b_ and the "S" shape angle $A_C$ affecting the "S" shape of the auxiliary tendon 19_c_ may be equal to each other. However, the auxiliary tendons 19_b_ and 19_c_ may be installed so that $A_b$ and $A_C$ are different due to design or other factors.

Also, each of the auxiliary tendons 19_b_ and 19_c_ rotates clockwise from the first link 11 to the sixth link 16 as shown in FIG. 23 and is installed in a kind of spiral shape. In this way, the clockwise or counterclockwise direction in which the auxiliary tendon is wound will be referred to as the "S"-shape direction.

The auxiliary tendons 19_b_ and 19_c_ illustrated in FIG. 23 may be installed in various "S" shapes.

A first example of this is to install the auxiliary tendon holes of each link in a sigmoid shape, accordingly, the auxiliary tendons 19_b_ and 19_c_ installed inside the auxiliary tendon holes are also installed in a sigmoid shape. FIG. 23 is an example of this.

However, it may be difficult to install the auxiliary tendon hole in the form of a sigmoid curve. Therefore, the second example of various "S" shapes is to install the auxiliary tendon holes of each link in an oblique shape having a predetermined angle with the center line of the link, and when combining the links, the holes become closer to a sigmoid shape.

FIG. 24 is also a virtual development view in which the virtual outer surface of the rolling joint device of FIG. 22 is cut along P-P', and the auxiliary tendon holes installed in each link 11-16 are installed in an oblique line instead of a curved line. Accordingly, the trajectories of the auxiliary tendon holes may have a stepped shape spaced apart from each other.

However, by manipulating the trajectory of the auxiliary tendon holes of each link, when the links are combined, it is possible to make the auxiliary tendon holes generally resemble a sigmoid. As a result, the auxiliary tendons 19_b_ and 19_c_ installed in the hole may also have the "S" shape similar to a sigmoid. Also, as the number of links included in the rolling joint device increases, the trajectories of the auxiliary tendon holes may also become more similar to the sigmoid.

A second embodiment of the above modification or improvement relates to various structures and methods for installing auxiliary tendons on each link.

As described above, the auxiliary tendons may be installed in such a way that they are movably inserted into the auxiliary tendon holes installed in the wall between the outer and inner surfaces of each link having a cylindrical shape.

Alternatively, after installing one or more guides on each link, auxiliary tendons may be installed inside or around the guides. For example, by installing guides on the inner surface of each link, auxiliary tendons may be installed along the guides. However, in this case, the guide may not protrude from the inner surface to the inner space of the link as much as possible so as not to interfere with the operation and movement of various devices inserted into the empty space inside the link.

As another example, by installing a guide on the outer surface of each link, the auxiliary tendon may be installed along the guide. However, at this time, the guide may not protrude from the outer surface as much as possible, so that the guide does not damage internal organs during various procedures.

The guide may have various structures. For example, the guide may be manufactured in the form of a hole or groove that protrudes on an outer surface, an inner surface, etc. and may receive an auxiliary tendon therein. Alternatively, the guide may be manufactured in a form in which an auxiliary tendon is installed into the groove as a groove in the outer or inner surface.

A third embodiment of the above modification or improvement relates to a structure and method for manipulating the "S" shape of an auxiliary tendon by manipulating the number, shape or structure of the auxiliary tendon hole.

For example, as shown in FIG. 23 and FIG. 24, the auxiliary tendons 19_b_, 19_c_ may be mounted to be positioned on an upper portion and a lower portion of the virtual outer surface of the device, respectively. This corresponds to a case where the angles $A_b$ and $A_C$ shown in FIG. 23 and FIG. 24 are smaller than 180°. Also in this case, $A_b$ and $A_C$ may be greater than, equal to or less than 90°.

Unlike FIG. 23 and FIG. 24, the device may be fabricated such that one or more auxiliary tendons 19_b_, 19_c_ are located both upper and lower portions of the virtual outer surface of the device, and FIG. 25 illustrates a case in which respective auxiliary tendons 19_b_, 19_c_ are located both upper and lower portions of the virtual outer surface.

Of course, each of the auxiliary tendons 19_b_, 19_c_ "S" angles $A_b$ and $A_C$ may be greater or less than 90°, or greater or less than 180°. In other words, according to the position defining the P-P' of the first link 11 in the development view or the position of each auxiliary tendon 19_b_, 19_c_, even when $A_b$ or $A_C$ is 10°, the trajectories of the auxiliary tendons 19_b_, 19_c_ may be located on both upper and lower portions of the virtual outer surface.

As a different example, unlike FIG. 23 and FIG. 24, the "S" angle of the one or more auxiliary tendons 19_b_, 19_c_ may be greater than 180°, and in some cases, greater than 270° or 360°.

FIG. 26 exemplifies a case in which the "S"-shape angle of each auxiliary tendon 19_b_, 19_c_ is greater than 360°. As an example, each of the auxiliary tendons 19_b_, 19_c_ is positioned at both the upper and lower portions in the development view, as well as additionally positioned at one or more of the upper and lower portions.

As illustrated in FIG. 23 to FIG. 26, each auxiliary tendon may be installed to have various "S"-shaped angles. In general, if the "S" angle is very small, such as 10°, 20°, etc., the degree of stiffness reinforcement may be insignificant. Also, when the "S" angle is too large, such as 480° or 720°, user operation may become difficult.

Therefore, in the case of a rolling joint devices equipped with a pair of auxiliary tendons, the auxiliary tendons may be installed such that the "S" angel of each auxiliary tendon is generally 30° to 150°, 40° to 135°, 50° to 120°, 60° to 105°, and 70° to 90°.

However, the "S" angle of each auxiliary tendon may be different depending on the location and characteristics of the target site, the size or shape of the surgical tool, the operating method of the surgical tool, the type or characteristics of the procedure, and the like. Also, the "S" angle of each auxiliary tendon is generally the same, but in some cases, it may be installed with a slight or significant difference.

A fourth embodiment of the modification or improvement relates to a rolling joint device in which two pairs of auxiliary tendons are installed, and to various structures and methods of auxiliary tendon holes of the device.

Figure 27:
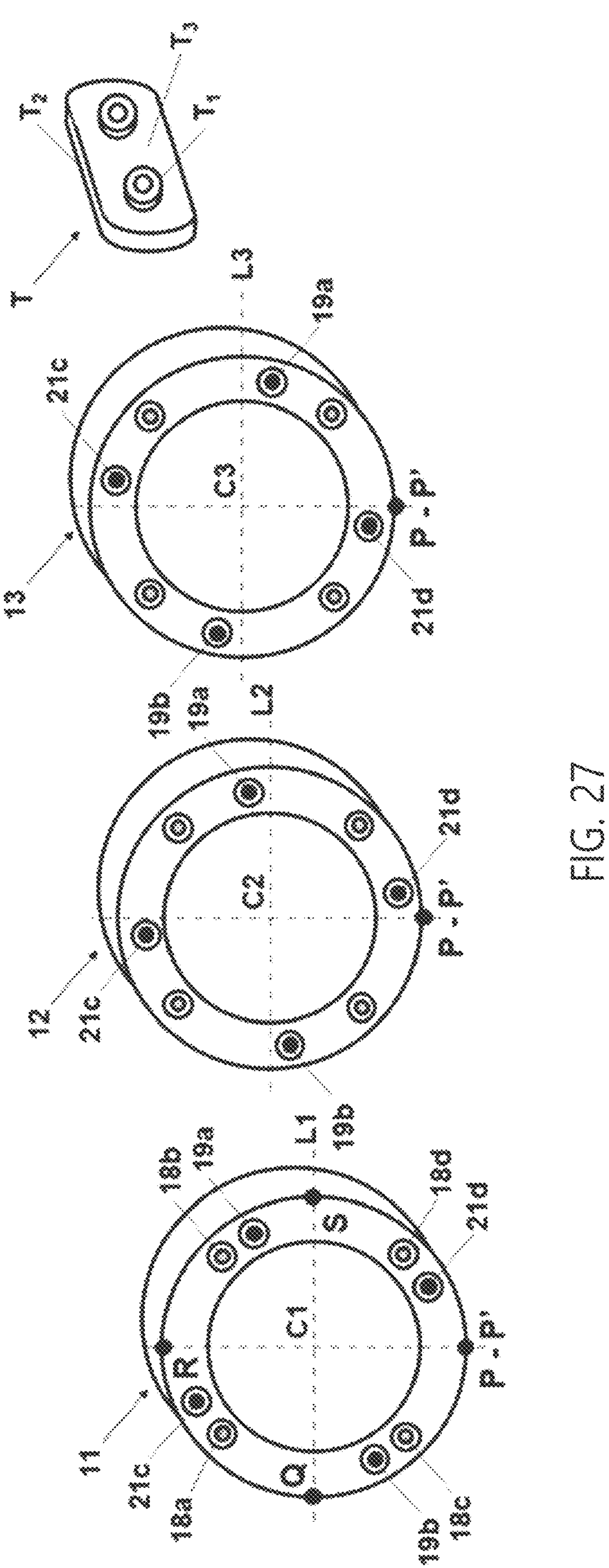
FIG. 27 is a schematic diagram illustrating a rolling joint device including a total of 6 links and 4 main tendons.

FIG. 27 is similar to FIG. 16, but the rolling joint device of FIG. 27 has a total of six links (ie, the first link 11, the second link 12, the third link 13, the fourth link 14, fifth link 15 and sixth link) and a tip T, including two sets of main tendons 18*a*, 18*b*, 18*c*, 18*d* (total of 4) and two sets of auxiliary tendons 19*a*, 19*b*, 21*c*, 21*d* (total of 4) are installed along the links.

However, for convenience of explanation, only the first to third links 11, 12, 13 and the tip T are shown in FIG. 27. In addition, one or more additional links (eg, seventh link, eighth link, ninth link), one or more connecting links, etc. may be added between the sixth link 16 and the tip T.

The auxiliary tendons 19*a* and 19*b* and the tip T of the first link 11, the second link 12 and the third link 13 of FIG. 27 are installed in the same way as the auxiliary tendons 19*c* and 19*b* and the tip of FIG. 22, respectively.

In the first link 11 of FIG. 27, the auxiliary tendon 21*c* is installed inside the hole in the upper left side of the cross section of the first link 11. In addition, the auxiliary tendon 21*d* is installed inside the hole on the lower right side of the cross section. In addition, the auxiliary tendon 21*c* is installed above the neutral line L1 of the first link 11, while the auxiliary tendon 21*d* is located below the neutral line L1.

In the case of the second link 12, the auxiliary tendon 21*c* is installed in the hole located on the left side of the cross section of the second link 12, higher than the position of the first link 11, and also above the neutral line L2. On the other hand, the auxiliary tendon 21*d* is installed in the hole located on the right side of the cross section, lower than the position of the first link 11, and also below the neutral line L1.

In the case of the third link 13, the auxiliary tendon 21*c* is installed inside the hole located on the upper right side of the cross section of the third link 13 and above the neutral line L3, whereas the auxiliary tendon 21*d* is the It is installed inside the hole located at the lower left side of the section, below the neutral line L3.

In the case of the tip T, the auxiliary tendon 21*c* may be installed at various locations on one side of the tip (eg, the surface shown in FIG. 27), for example, $T_1$, $T_2$, $T_3$, and the like. On the other hand, the auxiliary tendon 21*d* may be installed in various portions of the opposite side of the tip (eg, the side not shown in FIG. 27).

In addition, each of the auxiliary tendons 19*a*, 19*b*, 21*c*, 21*d* of FIG. 27 is installed in the "S"-shape direction, which rotates in a clockwise spiral form from the first link 11 to the sixth link 16.

Figure 28:
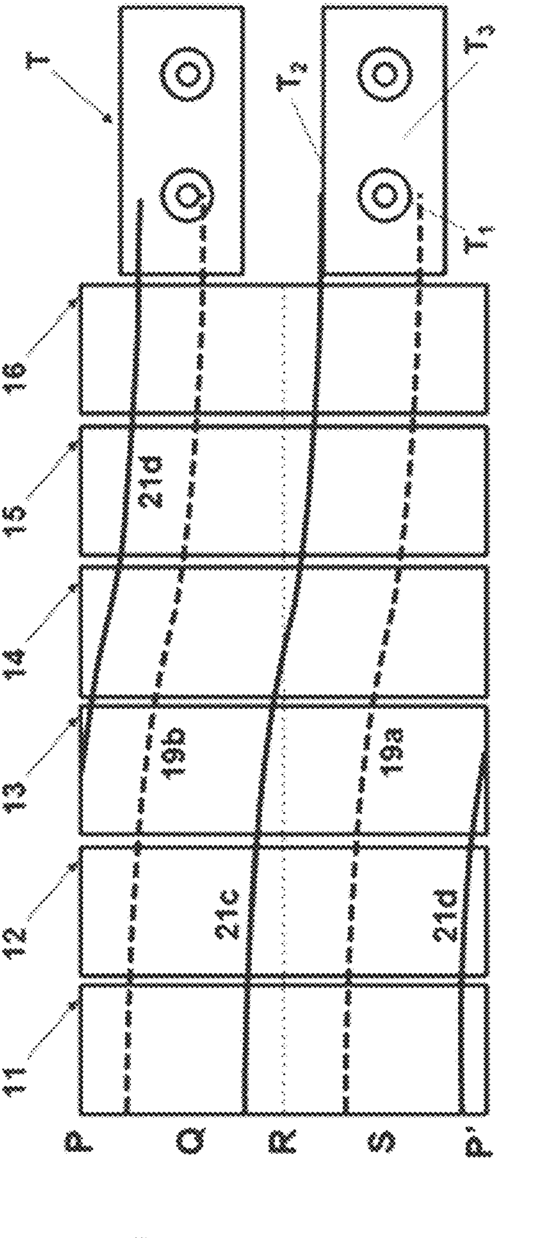
FIG. 28 is a virtual development view in which a virtual outer surface of the device of FIG. 27 is cut.
Figure 28:
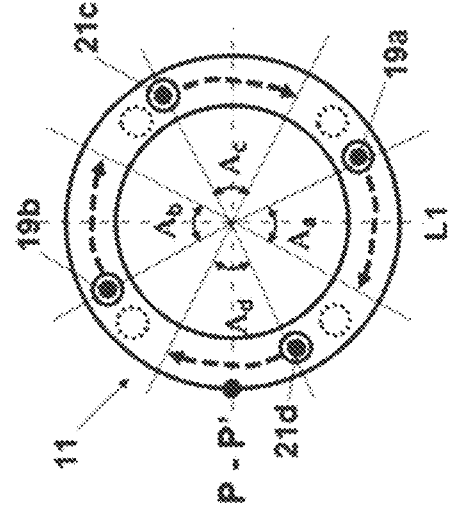

FIG. 28 is a virtual development view in which a virtual outer surface of the device is cut along the P-P' of the left panel of FIG. 27 and FIG. 28 in the rolling joint device manufactured by combining six links (i.e., the first to sixth links 11~16) in a line, and combining the tip T to the sixth link 16. At this time, since the diameter of each link 11~16 is larger than the height of the tip T, the outer surface of the tip is divided into two and marked separately.

As shown in FIG. 28, the auxiliary tendon 19*b* is installed in the "S" shape above the virtual outer surface of the device of FIG. 27, while the auxiliary tendon 19*a* is installed in the "S" shape below the virtual outer surface. Accordingly, when the virtual development view of FIG. 28 is folded along a straight line passing through R, a set of auxiliary tendons 19*a* and 19*b* may be regarded as intersecting in the form of an "X" as in the example of FIG. 12.

On the other hand, the auxiliary tendon 21*c* is installed in the first link 11, starting from the upper portion of the virtual outer surface, in the sixth link 16, below the outer surface, whereas the auxiliary tendon 21*d* is installed in the first link 11, starting from the lower portion of the outer surface, in the sixth link 16, below the outer surface.

Compared to the rolling joint device of FIG. 23 in which a pair of auxiliary tendons 19*b*, 19*c* are installed, in the case of the rolling joint device of FIG. 28 in which two pairs of auxiliary tendons 19*a*, 19*b*, 21*c*, 21*d* are installed, each the "S"-shaped angle of the auxiliary tendons 19*a*, 19*b*, 21*c*, 21*d* may be smaller than the "S"-shaped angle of the auxiliary tendons 19*b*, 19*c* of FIG. 23.

However, when one or more auxiliary tendons of the two pairs of auxiliary tendons 19*a*, 19*b*, 21*c*, 21*d* of the rolling joint device of FIG. 28 have a large "S" angle as in FIG. 26 or FIG. 27, the "S" shape angle may be greater than the "S" shape angle of the auxiliary tendons 19*b*, 19*c* of the rolling joint device of FIG. 23.

Also, the "S"-shape angle of each of the auxiliary tendons 19*a*, 19*b*, 21*c*, 21*d* may be equal to each other. However, the device may be manufactured so that the "S" angles of the two or more auxiliary tendons 19*a*, 19*b*, 21*c*, 21*d* are different due to design or other factors.

The auxiliary tendons 19*a*, 19*b*, 21*c*, 21*d* illustrated in FIG. 28 may be installed in various "S" shapes. In particular, the various structures or methods described with reference to FIG. 23 to FIG. 26 may be equally or similarly applied to the auxiliary tendons 19*a*, 19*b*, 21*c*, 21*d* of FIG. 27 and FIG. 28, respectively.

Figure 29:
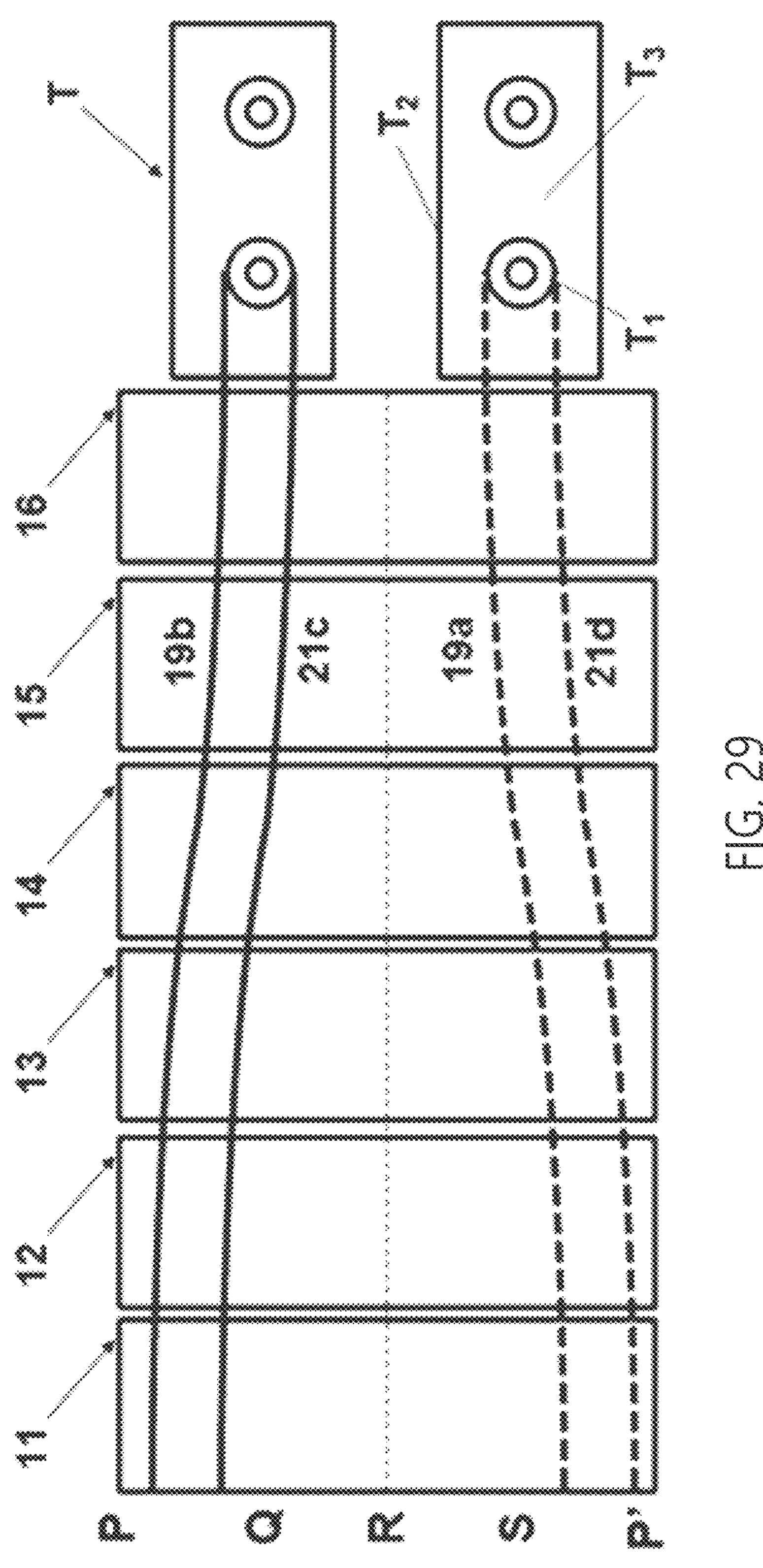
FIG. 29 and FIG. 30 illustrate examples in which two auxiliary tendons are installed in a clockwise direction and the remaining two auxiliary tendons are installed in a counterclockwise direction.
Figure 30:
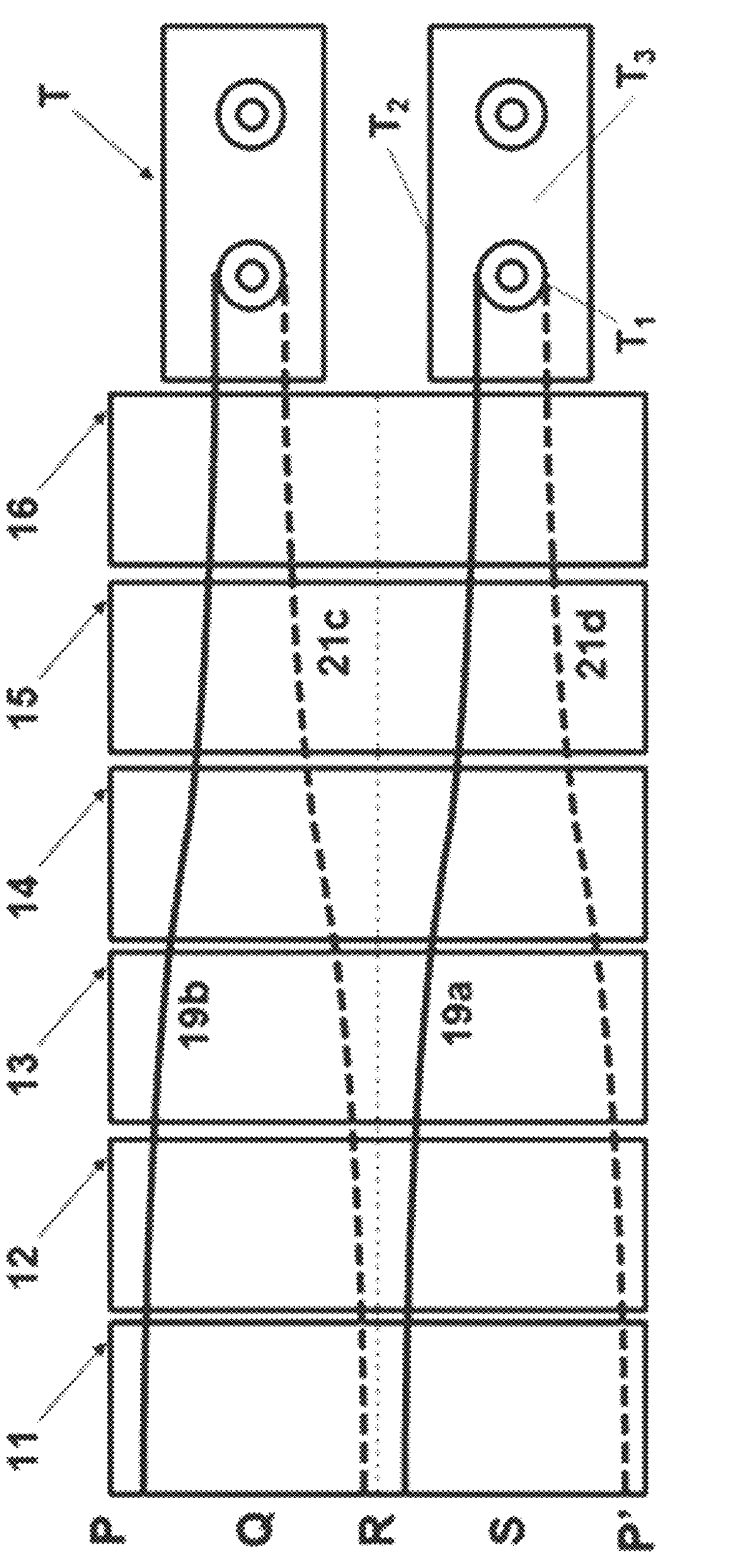

The two pairs of auxiliary tendons illustrated in FIG. 27 and FIG. 28 may be installed in different positions and in different structures. FIG. 29 and FIG. 30 are first examples thereof. For example, the two auxiliary tendons 19*b*, 21*c* of FIG. 29 and the two auxiliary tendons 19*a*, 19*b* of FIG. 30 are installed at the "S"-shape in a clockwise direction, while the two auxiliary tendons 19*a*, 21*d* of FIG. 29 and the auxiliary tendons 21*c*, 21*d* of FIG. 30 are installed at the "S"-shaped angle in the counterclockwise direction.

Compared with FIG. 28, the auxiliary tendons 19*a*, 19*b*, 21*c*, 21*d* of FIG. 29 and FIG. 30 may increase the stiffness of the rolling joint device to a similar degree.

When installing two pairs of auxiliary tendons, that is, a total of four auxiliary tendons in the rolling joint device, each auxiliary tendon is rotated in a clockwise or counter-clockwise "S" direction at various "S" angles so that they do not overlap each other on the virtual development view. Alternatively, they may be installed to overlap (that is, to cross) each other.

Figure 31:
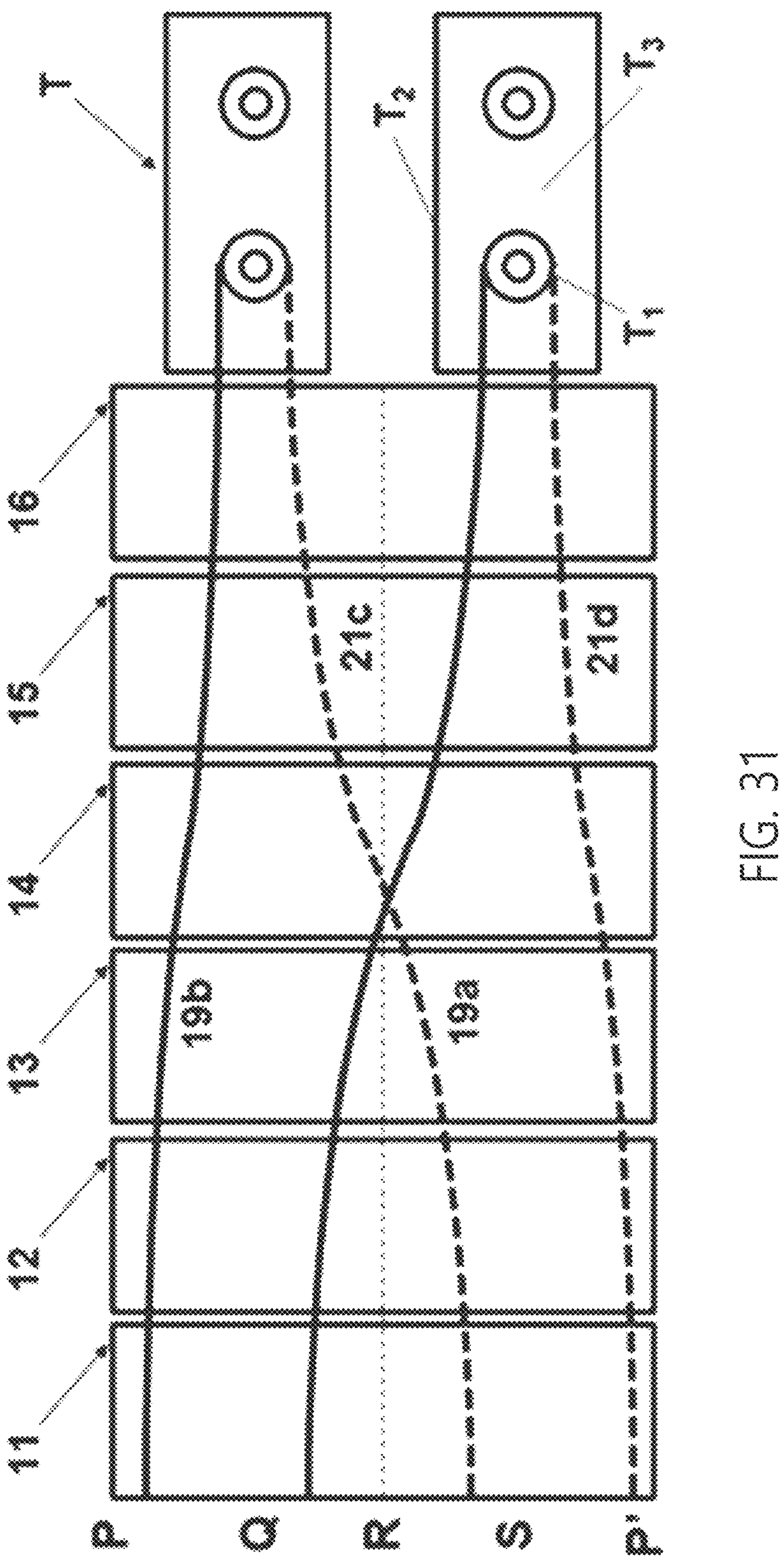
FIG. 31 illustrates a case in which at least two or more auxiliary tendons among four auxiliary tendons are installed to overlap or cross each other.

FIG. 31 is an example of a rolling joint device in which four auxiliary tendons 19*a*, 19*b*, 21*c*, 21*d* are installed. For example, in the case of FIG. 28 to FIG. 30 above, auxiliary tendons are installed in the "S"-shape and the "S"-shape that do not overlap (ie, do not intersect) each other on the virtual development view.

On the other hand, the auxiliary tendons 19*a*, 21*c* of FIG. 31 are installed in the "S" shape and the "S" angle that overlap or intersect each other on the virtual development view, but the auxiliary tendons 19*b* and the auxiliary tendon 21*d* are the virtual development view They are installed in the "S" shape and the "S" angle that do not overlap each other or do not intersect each other.

The auxiliary tendons 19*a*, 21*c* of FIG. 31 have a similar "S"-shaped angle but have different "S"-shaped directions, so they intersect each other. However, even if the "S" direction of the two auxiliary tendons is the same for the moon, the difference in the "S" angle is large, so it is possible to configure them to intersect each other. Also, a configuration in which one auxiliary tendon intersects two or more other auxiliary tendons is also possible.

A fifth embodiment of the modification or improvement relates to various structures and methods for installing at least one of a plurality of auxiliary tendons installed in the rolling joint device to have different physical properties, structures, or shapes from the other auxiliary tendons.

Figure 32:
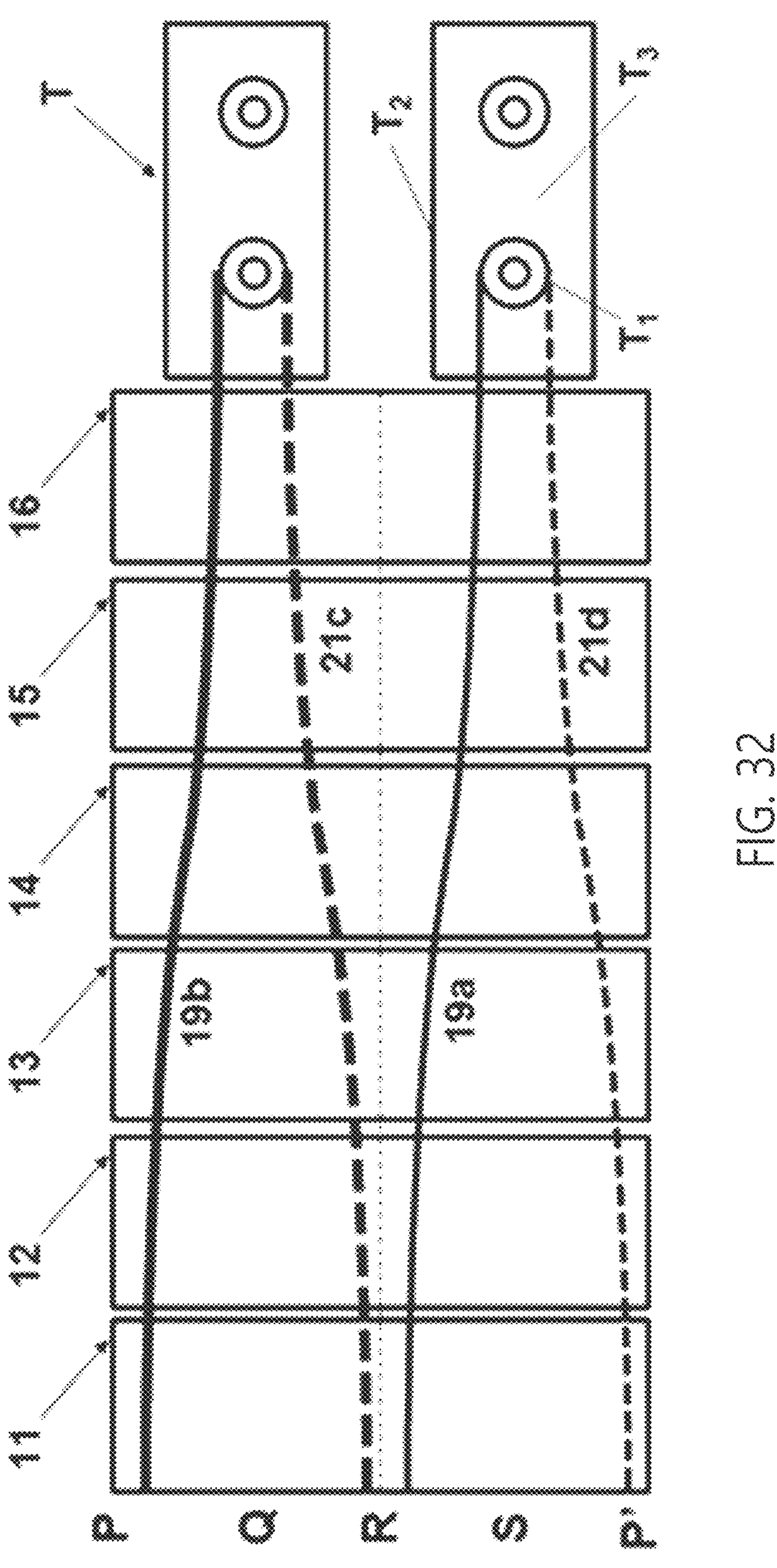
FIG. 32 illustrates an example in which at least one or more auxiliary tendons have different thicknesses, strengths, or elasticity.

FIG. 32 is a case in which a pair of auxiliary tendons 19*a*, 21*c* is thicker than the other pair of auxiliary tendons 19*a*, 21*d*, has higher strength, and has higher elasticity in a rolling joint device including two pairs of auxiliary tendons. Therefore, the user may more effectively minimize the rotation or deflection of a specific link or tip of a specific link or tip of the rolling joint device by manipulating the auxiliary tendons with different properties with different forces or pulling them by different lengths.

A sixth embodiment of the modification or improvement relates to various structures and methods for installing auxiliary tendons installed in the rolling joint device to have the "S" shape only in some links, not all links, of the device.

For example, when a rolling joint device is manufactured by combining six links, the auxiliary tendons described above pass through all six links of the device and are installed to have the "S" shape. However, when using the device, the rotation or deflection of the links (eg, the first or second link) located far from the target site may occur insignificantly.

In this case, the need for the auxiliary tendon to pass through the first or second links while maintaining the "S" shape is reduced. In addition, if the auxiliary tendon maintains the "S" shape in these links, the "S" angle of the "S" shape in the remaining links may also be reduced.

Figure 33:
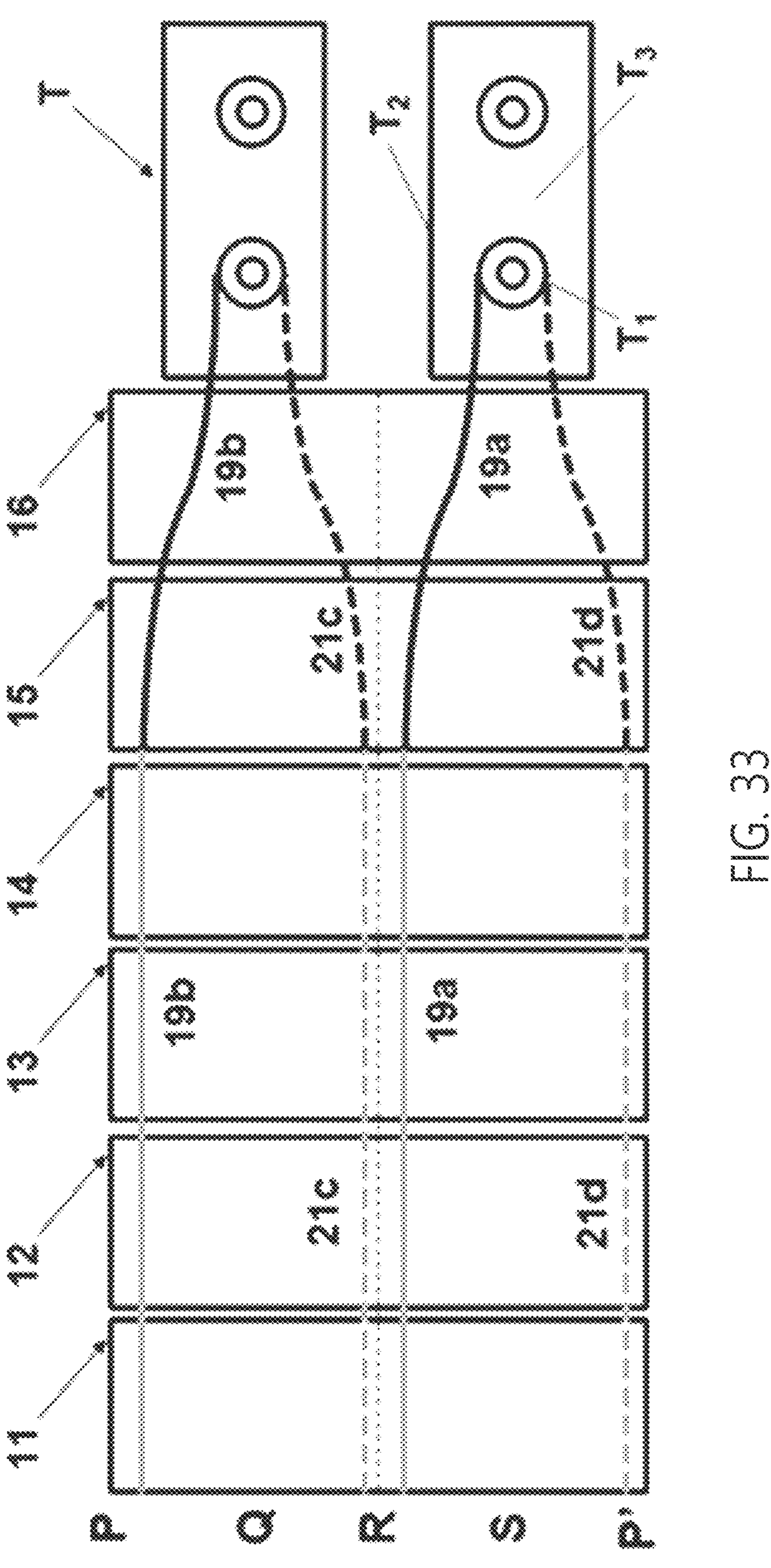
FIG. 33 illustrates an example of a rolling joint device including an auxiliary link installed to have a “S” shape only at a link close to a target site in which rotation or deflection occurs more severely.

FIG. 33 is an example embodiment of a rolling joint device in which an auxiliary tendon is installed to have the "S" shape only at a link close to a target site in which rotation or deflection occurs more severely, as described in the two paragraphs above.

For example, in the first to fourth links 11, 12, 13, 14 of the device, auxiliary tendon holes in a straight line form (almost) parallel to the central axis of each link are installed. Accordingly, the auxiliary tendons 19*a*, 19*b*, 21*c*, 21*d* inserted into the hole are also installed in a (almost) straight line parallel to the central axis of each link. In FIG. 33, the light gray solid line and the dotted line indicate portions installed in a (almost) straight line among the auxiliary tendons 19*a*, 19*b*, 21*c*, 21*d*.

However, in the fifth link 15 and the sixth link 16, an auxiliary tendon hole in the form of an oblique line is installed at a predetermined angle with the central axis of each link. Accordingly, the auxiliary tendons 19*a*, 19*b*, 21*c*, 21*d* inserted into the hole are also installed in the "S" shape inclined at the angle with respect to the central axis of the fifth link 15 and the sixth link 16. In FIG. 33, black solid lines and dotted lines indicate portions installed in an oblique or "S" shape among the auxiliary tendons 19*a*, 19*b*, 21*c*, 21*d*.

By the above configuration, the auxiliary tendons 19*a*, 19*b*, 21*c*, 21*d* are installed in the "S" direction at the "S" angle in the fifth link 15 and the sixth link 16, thus the "S"-shaped angle implemented per unit length in the central axis direction of the fifth to sixth link 15, 16 increases. As a result, the user may more easily minimize the rotation, deflection, etc. of the fifth to sixth link 15, 16 while ignoring the first to fourth links 11, 12, 13, and 15, which rarely rotate or deflect during use.

The auxiliary tendon may be installed differently from FIG. 33. For example, rotation, deflection, etc. of a link located close to the target site (e.g., the fifth or sixth links 15, 16) may be less than those of a link located far from the target site (e.g., the first or second links 11, 12).

In this case, by installing the auxiliary tendon hole in the form of an oblique line at predetermined angle with the central axis of each link in the first link 11 and the second link 12, the auxiliary tendons 19*a*, 19*b*, 21*c*, 21*d* passing through the hole may be installed in a spiral "S" shape inclined at the angle with the central axis of the links 11, 12.

Thereafter, auxiliary tendon holes in the form of a straight line (almost) parallel to the central axis of each link are installed in the third to sixth links 13, 14, 15, 16. Accordingly, the auxiliary tendons 19*a*, 19*b*, 21*c*, 21*d* inserted into the hole are also installed in a (almost) straight line parallel to the central axis of each link.

By the above configuration, the auxiliary tendons 19*a*, 19*b*, 21*c*, 21*d* are installed in the "S" direction at the "S" angle in the first link 11 and the second link 12, and thus the "S"-shaped angle implemented per unit length in the central axis direction of the first to second link 11, 12 increases. As a result, the user may more easily prevent rotation or deflection of the first to second links 11, 12 in the form of pitch, yaw, or roll.

Figure 34:
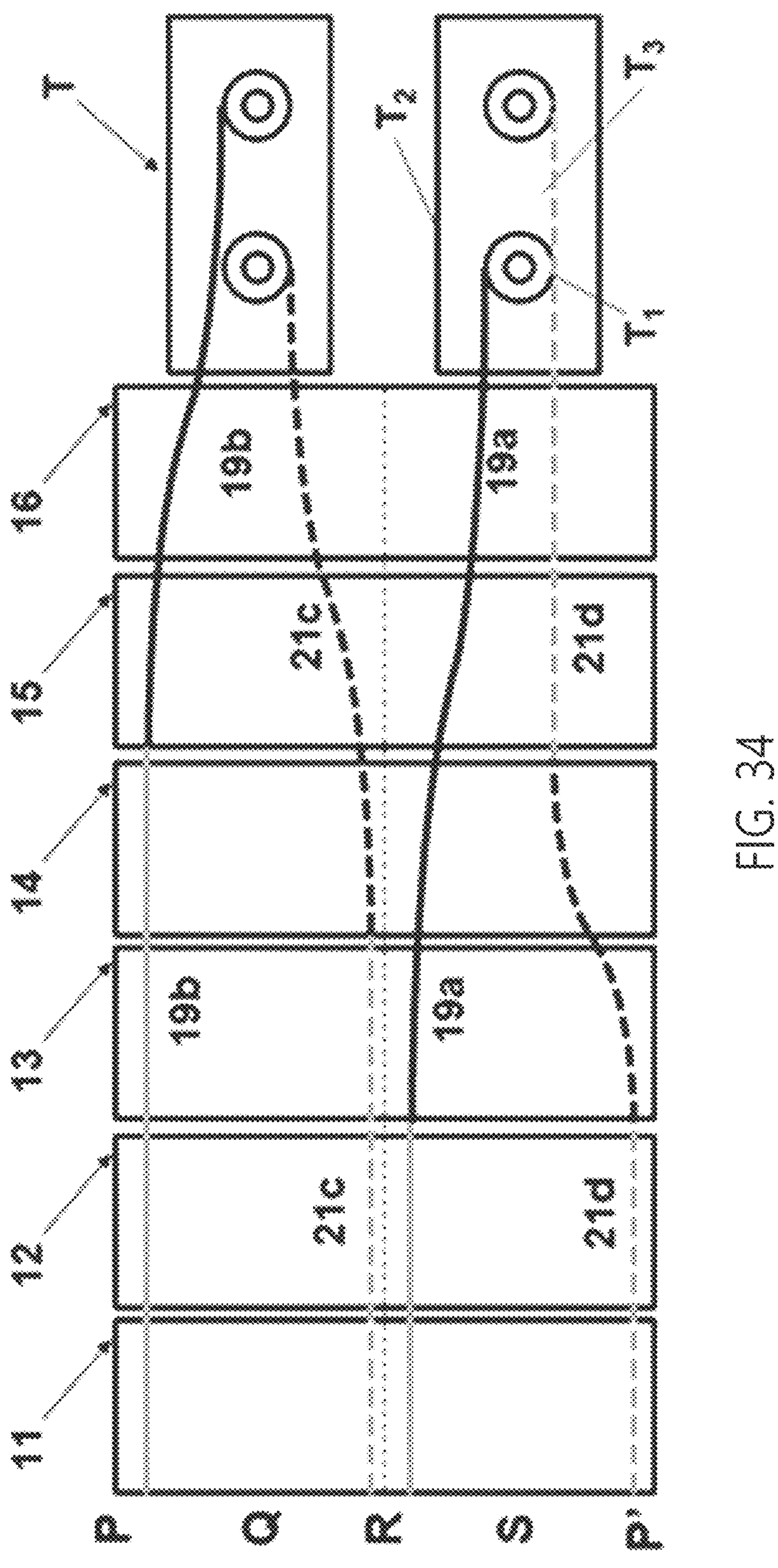
FIG. 34 illustrates a modification of FIG. 33.

FIG. 34 is another example of the sixth embodiment, wherein auxiliary tendons are installed at different positions, in the "S" shape of different lengths, or at the "S" angle.

The auxiliary tendon 19*b* is installed in a straight line parallel to the central axis in the first to fourth links 11, 12, 13, and 14, and is installed in the "S" shape in a clockwise "S" direction spiral up to the right end of the fifth link 15, the sixth link and the tip. On the other hand, the auxiliary tendon 19*a* is installed in a straight line parallel to the central axis in the first and second links 11, 12, and is installed in the "S" shape in a counterclockwise direction spiral in the S" direction in the third to sixth links 13, 14, 15, 16.

The auxiliary tendon 21*c* is installed in a straight line parallel to the central axis in the first to third links 11, 12, 13, and is installed in a "S" shape in a counterclockwise "S" direction spiral in the fourth to sixth links 14, 15, 16. The auxiliary tendon 21*d* is installed in a straight line parallel to the central axis in the first and second links 11, 12 and the fifth and sixth links 15, 16, and is installed in the "S" shape with a spiral in the "S" direction in the counterclockwise direction the third and fourth links 13, 14.

In this way, the structure in which a plurality of auxiliary tendons having the "S" shape of different lengths are installed at different positions may be decided based on the location and characteristics of the target site, the size and shape of the surgical tool, the operation method of the surgical tool, the type or characteristics of the procedure, an the like.

In other words, once a specific target region and procedure are determined and a surgical tool to be used is determined, using the above-described optimization technique, the number of auxiliary tendons optimizing the stiffness of the overtube to be used in the procedure and the path of the auxiliary tendon through the link of the overtube may be defined.

In this regard, the seventh embodiment of the modification or improvement relates to a method of optimizing the stiffness of the overtube of the rolling joint device differently depending on the target site, the type of operation and the surgical tool, and the path of the auxiliary tendon based thereon.

As an example, the above optimization technique is a technique for defining the path of the auxiliary tendon 19 for minimizing the sum of the position changes $|S_{d,\theta}|$ and $|S_{u,\theta}|$ caused by the downward force $F_d$ and the upward force $F_u$ illustrated in FIG. 6.

However, a modified optimization technique that can minimize values other than the sum of |Sd,θ| and |Su,θ| may be used depending on the target site, type of operation, and surgical tool.

The first example of the modified optimization technique is the case where the value of one of the position changes $|S_{d,\theta}|$ and $|S_{u,\theta}|$ caused by the downward force Fa and the upward force $F_{it}$ is significantly larger than the value of the other.

In this case, the path of the auxiliary tendon 19 may be defined by using the above-described optimization technique to minimize only one of $|S_{d,\theta}|$ and $|S_{u,\theta}|$.

In this case, one of the downward or upward force applied to the tip or overtube depending on the target area, the type of procedure, and the surgical tool may be slightly, and when the surgical tool is placed on the target area, it may be difficult to move upward or downward by the tissue of the target area.

A second example of a modified optimization technique is not to minimize the sum of the position changes $|S_{d,\theta}|$ and $|S_{u,\theta}|$ caused by the downward force Fa and the upward force $F_u$, but only one of the sum of $|S_{r,\theta}|$ and $|S_{f,\theta}|$, or $|S_{r,\theta}|$ and $|S_{f,\theta}|$, which are positional changes caused by force Fr applied right and force Fl applied left to the overtube or tip. Through this, it is possible to define the path of the auxiliary tendon 19 that can minimize the above-described left and right movement or rotation.

In this case, the downward or upward force applied to the tip or overtube is all slight depending on the target site, type of operation, and surgical tool, but when the surgical tool is positioned on the target, the surgical tool is Alternatively, there may be a case in which a tendency to move in the left direction occurs.

A third example of a modified optimization technique is not to minimize the sum of the position changes $|S_{d,\theta}|$ and $|S_{u,\theta}|$ caused by the downward force $F_d$ and the upward force $F_u$, but only to minimize the rotation by torque applied to the right side of the overtube or tip.

Therefore, by minimizing the sum of the position changes $|S_{c,\theta}|$ and $|S_{cc,\theta}|$ caused by the force $F_c$ to rotate the overtube or tip clockwise and the force $F_{cc}$ to rotate counterclockwise, or only one of $|S_{c,\theta}|$ and $|S_{cc,\theta}|$, the path of the auxiliary tendon 19 may be defined.

A fourth example of a modified optimization technique is a method of defining a path of an auxiliary tendon using an optimization technique capable of minimizing rotation or deflection of a pitch, a tip, or the like, or a yaw or roll shape by two or more forces such as $F_d$, $F_u$, $F_r$, $F_l$, $F_c$, $F_{cc}$, and the like.

As long as the overtube have sufficient flexibility and high stiffness, different embodiments, e.g., configurations, manufacturing methods, and usage methods for the surgical device or rolling joint device, link of the device, overtube, main tendon, main tendon holes, etc. may be compatible.

Therefore, specific embodiments or examples may [1] be applied to corresponding characteristics such as different embodiments and different examples, [2] be included in the corresponding characteristics, [3] replace the corresponding characteristics, [4] be replaced by the corresponding characteristics, or [5] be combined with the corresponding characteristics.

While this disclosure includes example embodiments, it will be apparent to one of ordinary skill in the art that various changes in form and details may be made in these example embodiments without departing from the spirit and scope of the claims and their equivalents. Therefore, the scope of the disclosure is defined not by the detailed description, but by the claims and their equivalents, and all variations within the scope of the claims and their equivalents are to be construed as being included in the disclosure.

What is claimed is:

1. A stiffness-reinforced surgical system, the system comprising:

a plurality of links provided rotatably with each other to form a joint device, the plurality of links including a first link body, a second link body, and a third link body, arranged consecutively, the first link body being formed with a first auxiliary tendon hole, the second link body being formed with a second auxiliary tendon hole, and the third link body being formed with a third auxiliary tendon hole;

a main tendon configured to form a traction force for driving the links;

an auxiliary tendon configured to form a traction force to resist rotation of the links, the auxiliary tendon being configured to pass through the first, second, and third auxiliary tendon holes; and a controller configured to control the traction forces of the main tendon and the auxiliary tendon, wherein the first auxiliary tendon hole is spaced apart from an auxiliary line perpendicular to a central axis of the plurality of links by a first distance, the second auxiliary tendon hole is spaced apart from the auxiliary line by a second distance, and the third auxiliary tendon hole is spaced apart from the auxiliary line by a third distance, with the first distance being greater than the second distance, and the auxiliary tendon holes are aligned along a continuously curved path defining a variable offset relative to the auxiliary line.

2. The system of claim 1, wherein the controller comprises:

a slider to which the main tendon is coupled, the slider being movably coupled to a rail;

a first driver configured to move the slider along the rail;

a first capstan on which the auxiliary tendon is wound; and a second driver configured to rotate the first capstan.

3. The system of claim 2, wherein the controller comprises:

a second capstan coupled to the same axis as the first capstan and on which a second wire is wound; and a second balance spring configured to pull the second wire so that the auxiliary tendon forms tension.

4. The system of claim 2, wherein the second driver comprises:

a motor; and an electronic clutch configured to selectively connect a shaft of the motor and a shaft of the first capstan.

5. The system of claim 2, wherein the controller comprises a first balance spring configured to pull a first wire connected to the slider so that the main tendon forms tension.

6. The system of claim 2, wherein the first driver comprises a linear actuator.

7. The system of claim 2, wherein the controller comprises:

a first body to which the rail is fixed and to which a shaft of the first capstan is rotatably coupled; and a second body to which the first driver and the second driver are coupled, the second body being detachably coupled to the first body, and when the first body and the second body are coupled, the slider and the first driver are coupled by a first coupler, and the shaft of the first capstan and a shaft of the second driver are coupled by a second coupler.

8. The system of claim 1, wherein the main tendon and the auxiliary tendon are configured to pass through the inside of the links, and a path of the auxiliary tendon inclines in an 'S' shape.

9. The system of claim 1, wherein the main tendon and the auxiliary tendon are configured to pass through the inside of the links, and some of paths of the auxiliary tendon incline.

10. The system of claim 9, wherein a plurality of the auxiliary tendons are provided, and a path of one of the auxiliary tendons and a path of another auxiliary tendons of the auxiliary tendons are symmetrical to each other with respect to a centerline of the links.

11. A control method of the stiffness-reinforced surgical system of claim 1, comprising:

pulling the main tendon to move the joint device to a lesion in a human body; and pulling the auxiliary tendon to increase stiffness of the joint device.

12. The control method of claim 11, wherein the auxiliary tendon comprises a first auxiliary tendon and a second auxiliary tendon, and the pulling of the auxiliary tendon comprises:

pulling the first auxiliary tendon to prevent deflection of the joint device; and pulling the second auxiliary tendon so as to prevent torsion of the joint device due to the pulling of the first auxiliary tendon.

13. The control method of claim 12, further comprising:

maintaining a traction force of the auxiliary tendon;

treating the lesion by driving a surgical robot provided in a lumen of the joint device;

releasing the traction force of the auxiliary tendon; and pulling the main tendon so that the joint device is retracted from the lesion.

14. The control method of claim 13, wherein the treating of the lesion comprises changing a traction force applied to the main tendon so that a position of the joint device is controlled in a state where a predetermined traction force is maintained on the auxiliary tendon.

15. The control method of claim 13, wherein the releasing of the traction force of the auxiliary tendon comprises:

releasing the traction force of the second auxiliary tendon; and releasing the traction force of the first auxiliary tendon.

* * * * *